(12) United States Patent
Jepsen et al.

(10) Patent No.: US 7,847,150 B2
(45) Date of Patent: Dec. 7, 2010

(54) **METHOD FOR BREEDING DOUBLE-TYPE *KALANCHOE* INTERSPECIFIC HYBRIDS**

(75) Inventors: Knud Jepsen, Hinnerup (DK); Ellen Christensen, Hinnerup (DK)

(73) Assignee: Knud Jepsen A/S, Hinnerup (DK)

( * ) Notice: Subject to any disclaimer, the term of this patent is extended or adjusted under 35 U.S.C. 154(b) by 190 days.

(21) Appl. No.: 12/286,064

(22) Filed: Sep. 26, 2008

(65) Prior Publication Data

US 2009/0044295 A1 Feb. 12, 2009

Related U.S. Application Data

(60) Division of application No. 11/302,139, filed on Dec. 14, 2005, now Pat. No. 7,453,032, which is a continuation-in-part of application No. 11/081,071, filed on Mar. 16, 2005, now abandoned, which is a continuation-in-part of application No. 11/011,618, filed on Dec. 15, 2004, now abandoned.

(51) Int. Cl.
*A01H 1/00* (2006.01)
*A01H 1/02* (2006.01)

(52) U.S. Cl. .................... 800/269; 800/260

(58) Field of Classification Search .......... 800/269, 800/260, 323; Plt./335, 336, 337, 338, 339, Plt./340, 341

See application file for complete search history.

(56) References Cited

PUBLICATIONS

Office Action issued on Mar. 31, 2009 in the counterpart, European patent application 05077885.1 (3 pages).

Kroon, G.H., "A Note on the Origin of *Kalanchoë x. vadensis* Boom & Zellinga (*Crassulaceae*)," *Euphytica*, 1994, vol. 125, p. 125.

*Primary Examiner*—Kent L Bell
(74) *Attorney, Agent, or Firm*—Foley & Lardner LLP

(57) ABSTRACT

New, distinct and stable cultivars of double-flowering *Kalanchoe* interspecific hybrids are disclosed. Double-flowering *Kalanchoe* interspecific hybrids produce one or more flowers with at least 5 full or partial petals per flower. Double-type *K. blossfeldiana*×*K. laciniata*, *K. blossfeldiana*×*K. rotundifolia*, *K. blossfeldiana*×*K. aromatica*, *K. blossfeldiana*×*K. pubescens*, *K. blossfeldiana*×*K. grandiflora*, *K. blossfeldiana*×*K. citrina*, *K. blossfeldiana*×*K. ambolensis*, *K. blossfeldiana*×*K. faustii*, *K. blossfeldiana*×*K. schumacherii*, *K. blossfeldiana*×*K. pritwitzii*, *K. blossfeldiana*×*K. flammea*, *K. blossfeldiana*×*K. figueredoi*, *K. blossfeldiana*×*K. rauhii*, *K. blossfeldiana*×*K. obtusa*, *K. blossfeldiana*×*K. pumila*, *K. blossfeldiana*×*K. marmorata*, *K. blossfeldiana*×*K. porphyrocalux*, *K. blossfeldiana*×*K. jongmansii*, *K. blossfeldiana*×*K. pinnata*, *K. blossfeldiana*×*K. diagremontiana*, *K. blossfeldiana*×*K. gracilipes*, *K. blossfeldiana*×*K. campanulata*, *K. blossfeldiana*×*K. latisepela*, *K. blossfeldiana*×*K. coccinea*, *K. blossfeldiana*×*K. fedtschenkoi*, *K. blossfeldiana*×*K. tubiflora*, *K. blossfeldiana*×*K. decumbens*, *K. blossfeldiana*×*K. manginii*, *K. blossfeldiana*×*K. orgyalis*, *K. blossfeldiana*×*K. crenata* and *K. blossfeldiana*×*K. tomentosa* are disclosed. The double-type flowering characteristic has been combined with many desirable *Kalanchoe* traits including different flower colors, growth characteristics and plant habit. Methods for the reliable breeding of the double-type characteristic into diverse *Kalanchoe* genetic backgrounds, as well as methods for increasing the number of petals per flower, are disclosed.

4 Claims, 30 Drawing Sheets
(30 of 30 Drawing Sheet(s) Filed in Color)

_US 7,847,150 B2_

METHOD FOR BREEDING DOUBLE-TYPE KALANCHOE INTERSPECIFIC HYBRIDS

CROSS-REFERENCE TO RELATED PATENT APPLICATIONS

This application is a divisional of U.S. application Ser. No. 11/302,139 filed Dec. 14, 2005, allowed, which is a continuation-in-part of U.S. application Ser. No. 11/081,071 filed Mar. 16, 2005, abandoned, which is a continuation-in-part of U.S. application Ser. No. 11/011,618 filed Dec. 15, 2004, abandoned.

FIELD OF INVENTION

The present invention relates to new, distinct, and stable cultivars of double-type *Kalanchoe* interspecific hybrids that produce one or more flowers with at least 5 full or partial petals per flower. The double-type *Kalanchoe* interspecific hybrids of the present invention include *Kalanchoe blossfeldiana*×*K. laciniata*, *K. blossfeldiana*×*K. rotundifolia*, *K. blossfeldiana*×*K. aromatica*, *K. blossfeldiana*×*K. pubescens*, *K. blossfeldiana*×*K. grandiflora*, *K. blossfeldiana*×*K. citrina*, *K. blossfeldiana*×*K. ambolensis*, *K. blossfeldiana*×*K. faustii*, *K. blossfeldiana*×*K. schumacherii*, *K. blossfeldiana*×*K. pritwitzii*, *K. blossfeldiana*×*K. flammea*, *K. blossfeldiana*×*K. figueredoi*, *K. blossfeldiana*×*K. rauhii*, *K. blossfeldiana*×*K. obtusa*, *K. blossfeldiana*×*K. pumila*, *K. blossfeldiana*×*K. marmorata*, *K. blossfeldiana*×*K. porphyrocalux*, *K. blossfeldiana*×*K. jongmansii*, *K. blossfeldiana*×*K. pinnata*, *K. blossfeldiana*×*K. diagremontiana*, *K. blossfeldiana*×*K. gracilipes*, *K. blossfeldiana*×*K. campanulata*, *K. blossfeldiana*×*K. latisepela*, *K. blossfeldiana*×*K. coccinea*, *K. blossfeldiana*×*K. fedtschenkoi*, *K. blossfeldiana*×*K. tubiflora*, *K. blossfeldiana*×*K. decumbens*, *K. blossfeldiana*×*K. manginii*, *K. blossfeldiana*×*K. orgyalis*, *K. blossfeldiana*×*K. crenata* and *K. blossfeldiana*×*K. tomentosa*. The double-type *Kalanchoe* interspecific hybrids of the present invention also include double-type plants produced from crosses between the above-identified interspecific hybrids (e.g. (*K. blossfeldiana*×*K. laciniata*)×(*K. blossfeldiana*×*K. pubescens*)), as well as, crosses between interspecific hybrids containing *K. blossfeldiana* and interspecific hybrids not containing *K. blossfeldiana* in the genetic background (e.g. (*K. blossfeldiana*×*K. laciniata*)×(*K. grandiflora* x *K. pritwitzii*)). The double-type interspecific hybrid plants produce one or more flowers having at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more than 40 petals per flower. The double-type characteristic has been successfully introgressed from double-type *K. blossfeldiana* into other single-type (4 petals per flower) *Kalanchoe* species. The double-type interspecific hybrid plants can be used as either male or female parents in crosses to the parents, other selections from the same species as the parents, or selections from other *Kalanchoe* species. The double-type interspecific hybrid plants can also be selfed. The double-type flowering characteristic from *K. blossfeldiana* has been combined with many desirable traits from other *Kalanchoe* species including different flower colors, superior growth characteristics and improved plant habit. Methods for the reliable breeding of the double-type characteristic from *K. blossfeldiana*, or *Kalanchoe* interspecific hybrid plants, into diverse single-type *Kalanchoe* genetic backgrounds, as well as methods for increasing the number of petals per flower, are disclosed.

BACKGROUND OF THE INVENTION

The present invention relates generally to the field of ornamental *Kalanchoe* plants. The genus of *Kalanchoe* belongs to the sedum family (Crassulaceae). There are more than 100 different species of *Kalanchoe* of which more than 60 are found in Madagascar. Many species are found in South Africa and a few in Asia and South America. *Kalanchoe* belongs to the succulent plant group, which are characterized by their turgid leaves. The leaves enable members of this genus to survive drought conditions. Consequently, *Kalanchoe* are useful ornamental plants because they can survive in less than optimal growing conditions.

Species of *Kalanchoe* are described in J. T. Baldwin, *Amer. J. Bot.* 25: 572-579 (1938). Each species of *Kalanchoe* has traits a breeder would like to incorporate into commercial cultivars. Other traits a breeder will try to avoid.

*K. blossfeldiana* is a valuable ornamental species because it can be readily grown from seed, or reproduced asexually from cuttings, and produces abundant flowers that remain fresh for several weeks. Generally, *K. blossfeldiana* plants are highly branched and under certain conditions the height of the branches may be up to 30-45 cm. *K. blossfeldiana* plants generally produce erect flowers, oblong or ovate-oblong leaves, with a corolla that is red.

*K. blossfeldiana* can be crossed with numerous other *Kalanchoe* species to combine advantageous characteristics into unique new cultivars. Among the numerous interspecific hybrids that may be created are *K. blossfeldiana*×*K. laciniata*, *K. blossfeldiana*×*K. rotundifolia*, *K. blossfeldiana*×*K. aromatica*, *K. blossfeldiana*×*K. pubescens*, *K. blossfeldiana*×*K. grandiflora*, *K. blossfeldiana*×*K. citrina*, *K. blossfeldiana*×*K. ambolensis*, *K. blossfeldiana*×*K. faustii*, *K. blossfeldiana*×*K. schumacherii*, *K. blossfeldiana*×*K. pritwitzii*, *K. blossfeldiana*×*K. flammea*, *K. blossfeldiana*×*K. figueredoi*, *K. blossfeldiana*×*K. rauhii*, *K. blossfeldiana*×*K. obtusa*, *K. blossfeldiana*×*K. pumila*, *K. blossfeldiana*×*K. marmorata*, *K. blossfeldiana*×*K. porphyrocalux*, *K. blossfeldiana*×*K. jongmansii*, *K. blossfeldiana*×*K. pinnata*, *K. blossfeldiana*×*K. diagremontiana*, *K. blossfeldiana*×*K. gracilipes*, *K. blossfeldiana*×*K. campanulata*, *K. blossfeldiana*×*K. latisepela*, *K. blossfeldiana*×*K. coccinea*, *K. blossfeldiana*×*K. fedtschenkoi*, *K. blossfeldiana*×*K. tubiflora*, *K. blossfeldiana*×*K. decumbens*, *K. blossfeldiana*×*K. manginii*, *K. blossfeldiana*×*K. orgyalis*, *K. blossfeldiana*×*K. crenata* and *K. blossfeldiana*×*K. tomentosa*.

The breeding of *Kalanchoe* interspecific hybrids with double-type, rose-like flowers, with more than 5 petals per flower, offers a unique flower form that can be combined with diverse *Kalanchoe* plant characteristics from different species, thereby expanding the range of phenotypic characteristics available in this popular horticultural plant.

SUMMARY OF THE INVENTION

An object of the present invention is to provide a *Kalanchoe* interspecific hybrid plant having one or more double-type flowers with at least 5 full or partial petals per flower.

Another object of the present invention is to provide double-type *Kalanchoe* interspecific hybrid plants including *K. blossfeldiana*×*K. laciniata*, *K. blossfeldiana*×*K. rotundifolia*, *K. blossfeldiana*×*K. aromatica*, *K. blossfeldiana*×*K. pubescens*, *K. blossfeldiana*×*K. grandiflora*, *K. blossfeldi-* ana×K. citrina, K. blossfeldiana×K. ambolensis, K. blossfeldiana×K. faustii, K. blossfeldiana×K. schumacherii, K. blossfeldiana×K. pritwitzii, K. blossfeldiana×K. flammea, K. blossfeldiana×K. figueredoi, K. blossfeldiana×K. rauhii, K. blossfeldiana×K. obtusa, K. blossfeldiana×K. pumila, K. blossfeldiana×K. marmorata, K. blossfeldiana×K. porphyrocalux, K. blossfeldiana×K. jongmansii, K. blossfeldiana×K. pinnata, K. blossfeldiana×K. diagremontiana, K. blossfeldiana×K. gracilipes, K. blossfeldiana×K. campanulata, K. blossfeldiana×K. latisepela, K. blossfeldiana×K. coccinea, K. blossfeldiana×K. fedtschenkoi, K. blossfeldiana×K. tubiflora, K. blossfeldiana×K. decumbens, K. blossfeldiana×K. manginii, K. blossfeldiana×K. orgyalis, K. blossfeldiana×K. crenata and K. blossfeldiana×K. tomentosa interspecific hybrids.

Yet another object of the present invention is to provide a Kalanchoe interspecific hybrid plant in which substantially all the flowers produced by the plant are double-type with at least 5 full or partial petal per flower.

Another object of the present invention is to provide a Kalanchoe interspecific hybrid plant wherein a double-type flower has at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more than 40 petals per flower.

An object of the present invention is to provide a method for breeding a double-type Kalanchoe interspecific hybrid plant that produces one or more flowers with at least 5 full or partial petals per flower comprising the steps of (a) crossing a double-type K. blossfeldiana double-type plant, either as the male or female parent, with a single-type Kalanchoe plant selected from the group consisting of K. laciniata, K. rotundifolia, K. aromatica K. pubescens, K. grandiflora, K. citrine, K. ambolensis, K. faustii, K. schumacherii, K. pritwitzii, K. flammea, K. figueredoi, K. rauhii, K. obtuse, K. pumila, K. marmorata, K. porphyrocalux, K. jongmansii, K. pinnata, K. diagremontiana, K. gracilipes, K. campanulata, K. latisepela, K. coccinea, K. fedtschenkoi, K. tubiflora, K. decumbens, K. manginii, K. orgyalis, K. crenata and K. tomentosa; and (b) selecting progeny that produce one or more flowers with at least 5 full or partial petals per flower.

Another object of the present invention is to provide a method for breeding a double-type Kalanchoe interspecific hybrid plant that produces one or more flowers with at least 5 full or partial petals per flower wherein the double-type interspecific progeny plant is back-crossed with one of the parents.

Another object of the present invention is provide a method for breeding a double-type Kalanchoe interspecific hybrid plant that produces one or more flowers with at least 5 full or partial petals per flower comprising the step of selfing a double-type Kalanchoe interspecific hybrid selected from the group consisting of K. blossfeldiana×K. laciniata, K. blossfeldiana×K. rotundifolia, K. blossfeldiana×K. aromatica, K. blossfeldiana×K. pubescens, K. blossfeldiana×K. grandiflora, K. blossfeldiana×K. citrina, K. blossfeldiana×K. ambolensis, K. blossfeldiana×K. faustii, K. blossfeldiana×K. schumacherii, K. blossfeldiana×K. pritwitzii, K. blossfeldiana×K. flammea, K. blossfeldiana×K. figueredoi, K. blossfeldiana×K. rauhii, K. blossfeldiana×K. obtusa, K. blossfeldiana×K. pumila, K. blossfeldiana×K. marmorata, K. blossfeldiana×K. porphyrocalux, K. blossfeldiana×K. jongmansii, K. blossfeldiana×K. pinnata, K. blossfeldiana×K. diagremontiana, K. blossfeldiana×K. gracilipes, K. blossfeldiana×K. campanulata, K. blossfeldiana×K. latisepela, K. blossfeldiana×K. coccinea, K. blossfeldiana×K. fedtschenkoi, K. blossfeldiana×K. tubiflora, K. blossfeldiana×K. decumbens, K. blossfeldiana×K. manginii, K. blossfeldiana× K. orgyalis, K. blossfeldiana×K. crenata and K. blossfeldiana×K. tomentosa.

Yet another object of the present invention is to provide a method for breeding a double-type Kalanchoe interspecific hybrid plant that produces one or more flowers with at least 5 full or partial petals per flower comprising the steps of (a) crossing a double-type Kalanchoe interspecific hybrid selected from the group consisting of K. blossfeldiana×K. laciniata, K. blossfeldiana×K. rotundifolia, K. blossfeldiana×K. aromatica, K. blossfeldiana×K. pubescens, K. blossfeldiana×K. grandiflora, K. blossfeldiana×K. citrina, K. blossfeldiana×K. ambolensis, K. blossfeldiana×K. faustii, K. blossfeldiana×K. schumacherii, K. blossfeldiana×K. pritwitzii, K. blossfeldiana×K. flammea, K. blossfeldiana×K. figueredoi, K. blossfeldiana×K. rauhii, K. blossfeldiana×K. obtusa, K. blossfeldiana×K. pumila, K. blossfeldiana×K. marmorata, K. blossfeldiana×K. porphyrocalux, K. blossfeldiana×K. jongmansii, K. blossfeldiana×K. pinnata, K. blossfeldiana×K. diagremontiana, K. blossfeldiana×K. gracilipes, K. blossfeldiana×K. campanulata, K. blossfeldiana×K. latisepela, K. blossfeldiana×K. coccinea, K. blossfeldiana× K. fedtschenkoi, K. blossfeldiana×K. tubiflora, K. blossfeldiana×K. decumbens, K. blossfeldiana×K. manginii, K. blossfeldiana×K. orgyalis, K. blossfeldiana×K. crenata and K. blossfeldiana×K. tomentosa, as the male or female parent, with single or double-type Kalanchoe plant of the same or different species; and (b) selecting a progeny plant that produces double-type flowers.

BRIEF DESCRIPTION OF THE DRAWINGS

The patent or application file contains at least one drawing executed in color. Copies of this patent or patent application publication with color drawings will be provided by the Office upon request and payment of the necessary fees.

Flower bud from the top; F. Inside a flower; G. Flower bud from the site; H. Petal; I. Sepal; J. Pistil; K. Mature leaf and L. Young leaf.

Figure 1:
FIG. 1. A top perspective view of a typical potted flowering plant of Kalanchoe cultivar 'KJ 2003 0761' 18 weeks after planting of cutting.
Figure 2:
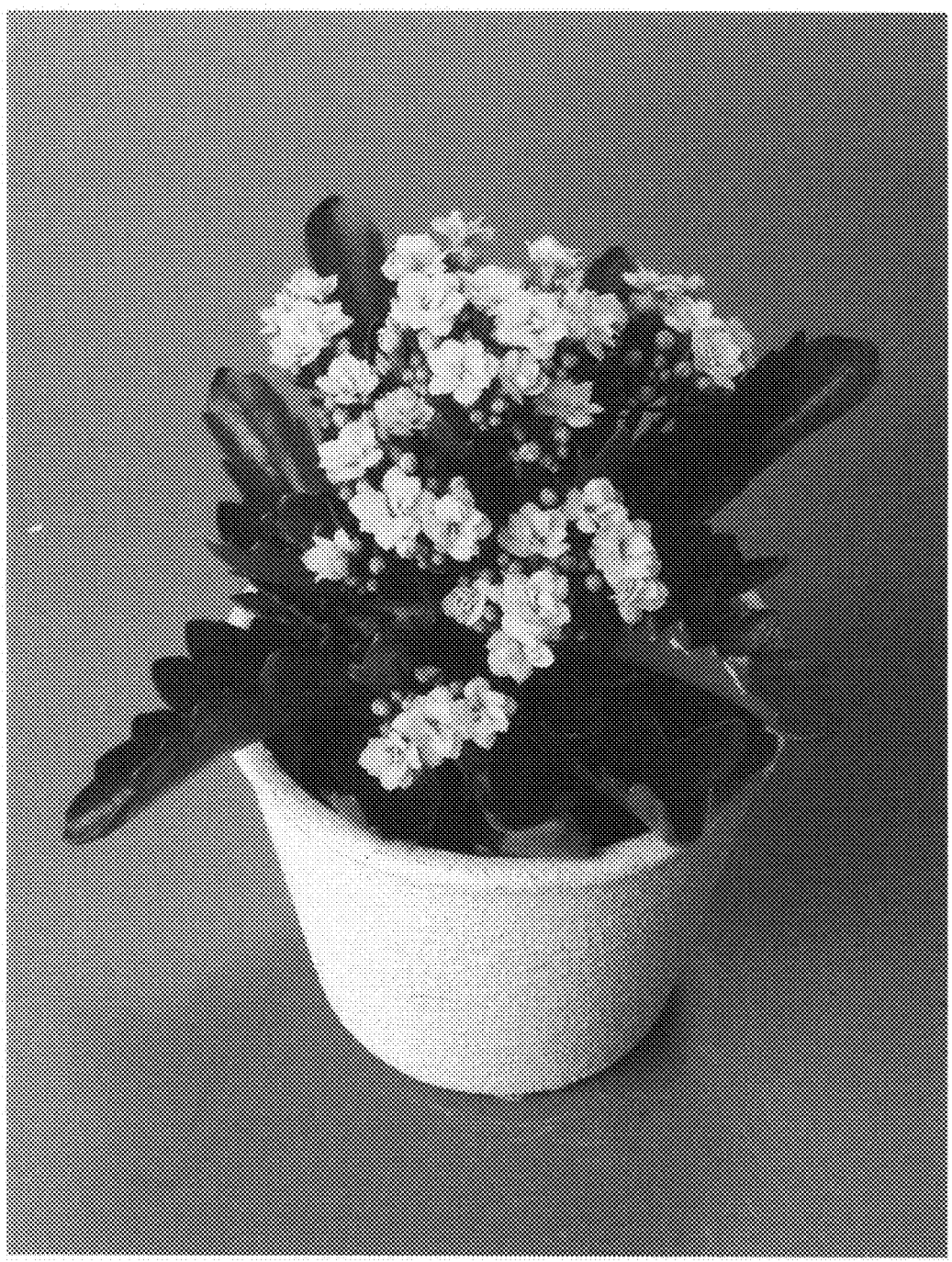
FIG. 2. A side perspective view of a typical potted flowering plant of Kalanchoe cultivar 'KJ 2003 0761' 18 weeks after planting of cutting.
Figure 3:
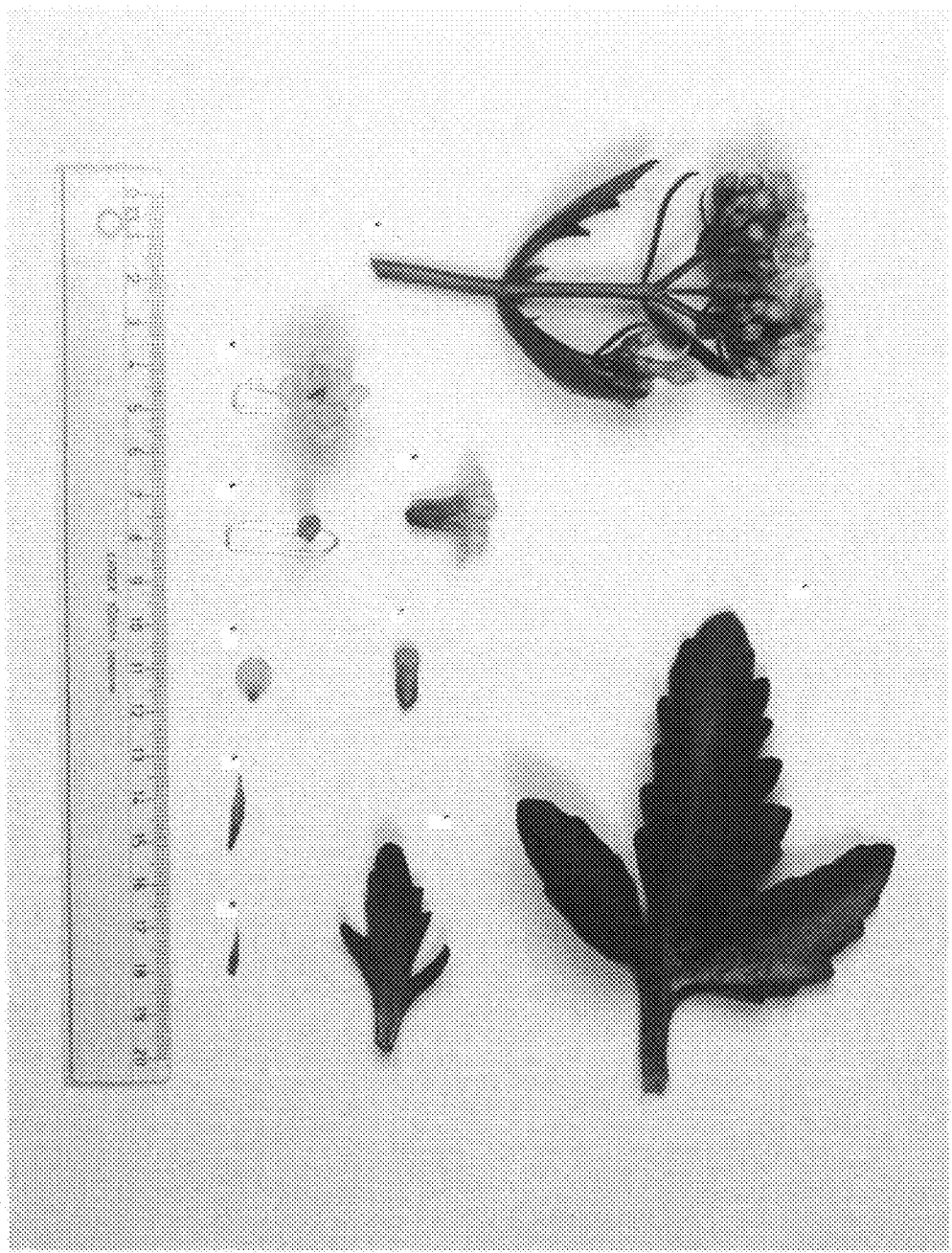
FIG. 3. Representative plant parts of Kalanchoe cultivar 'KJ 2003 0761': A. Inflorescence; B. Inside a flower; C. Flower bud, site; D. Flower; E. Flower bud, top; F. Petal; G. Pistil; H. Sepal; I. Mature leaf; J. Young leaf.
Figure 4:
FIG. 4. A top perspective view of a typical potted flowering plant of Kalanchoe cultivar 'KJ 2003 0638' 18 weeks after planting of cutting.
Figure 5:
FIG. 5. A side perspective view of a typical potted flowering plant of Kalanchoe cultivar 'KJ 2003 0638' 18 weeks after planting of cutting.
Figure 6:
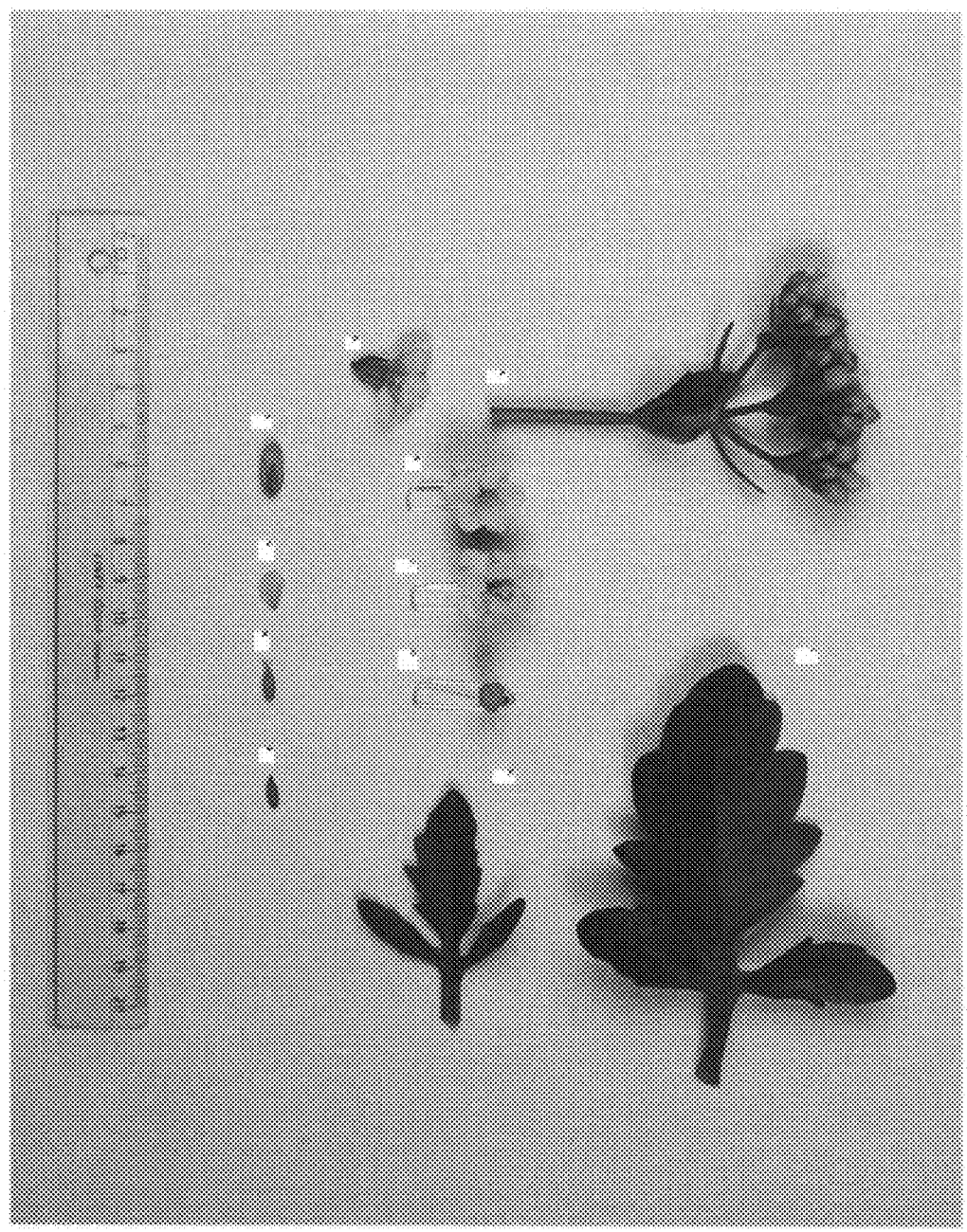
FIG. 6. Representative plant parts of Kalanchoe cultivar 'KJ 2003 0638': A Inflorescence; B. Flower, just opened; C. Flower opened one week, D. Flower bud, top; E. Inside a flower; F. Flower bud, site; G. Petal; H. Pistil; I. Sepal; J. Mature leaf; and K. Young leaf.
Figure 7:
FIG. 7. A top perspective view of a typical potted flowering plant of Kalanchoe cultivar 'KJ 2003 0747' 16 weeks after planting of cutting.
Figure 8:
FIG. 8. A side perspective view of a typical potted flowering plant of Kalanchoe cultivar 'KJ 2003 0747' 16 weeks after planting of cutting.
Figure 9:
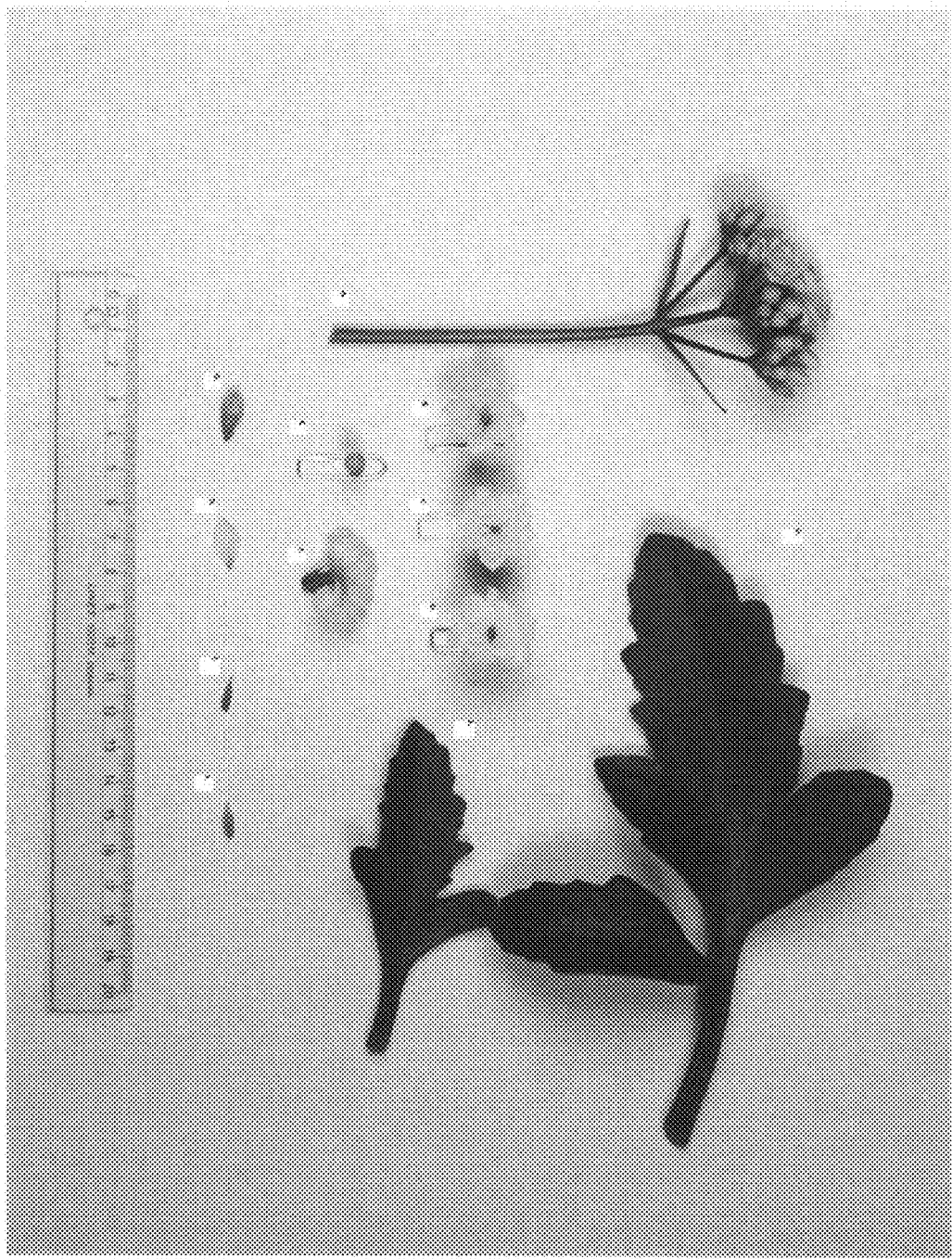
FIG. 9. Representative plant parts of Kalanchoe cultivar 'KJ 2003 0747': A. Inflorescence; B. Flower, just opened; C. Flower, opened one week; D. Color of a faded flower; E.
Figure 10:
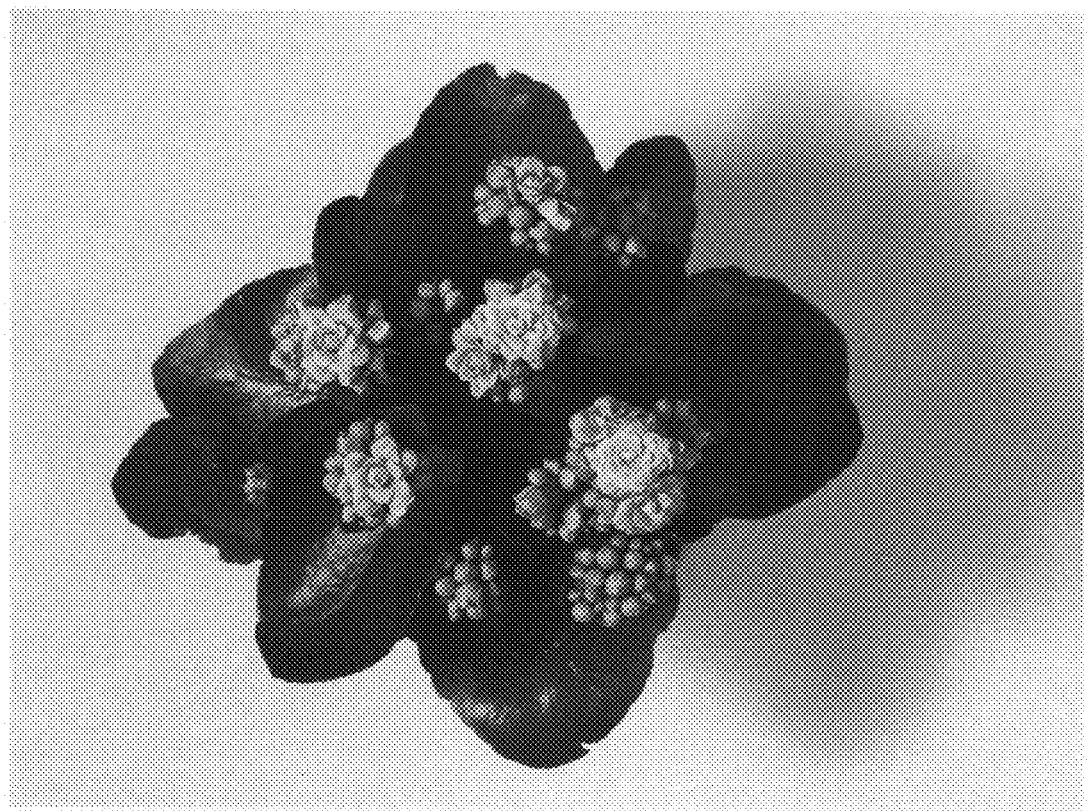

FIG. 10. A top perspective view of a typical potted flowering plant of *Kalanchoe* cultivar 'KJ 2003 0818' 19 weeks after planting of cutting.

Figure 11:

FIG. 11. A side perspective view of a typical potted flowering plant of *Kalanchoe* cultivar 'KJ 2003 0818' 18 weeks after planting of cutting.

Figure 12:
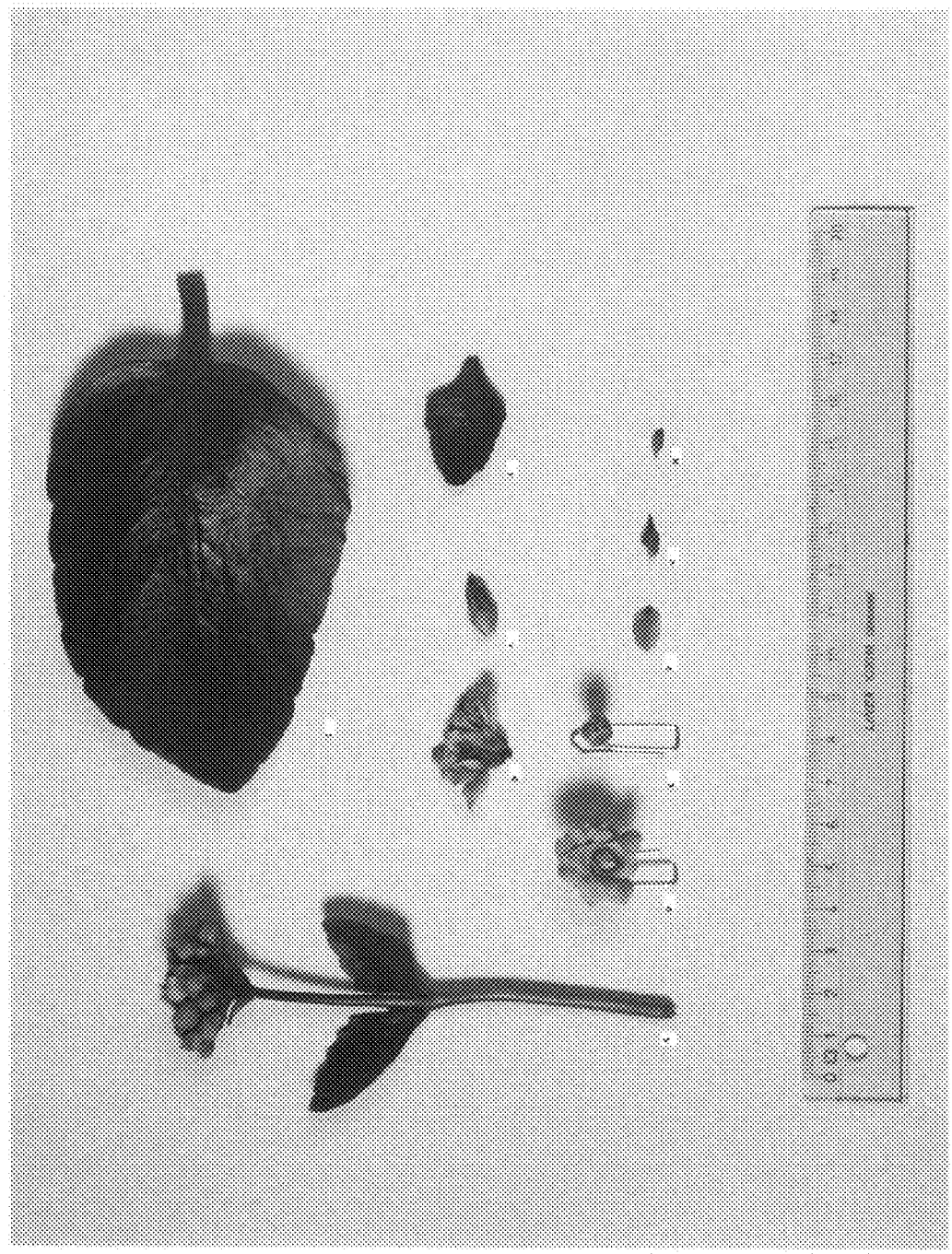

FIG. 12. Representative plant parts of *Kalanchoe* cultivar 'KJ 2003 0818': A. Inflorescence; B. Inside a flower; C. Flower bud, site; D. Flower; E. Flower bud, top; F. Petal; G. Pistil; H. Sepal; I. Mature leaf; J. Young leaf.

Figure 13:
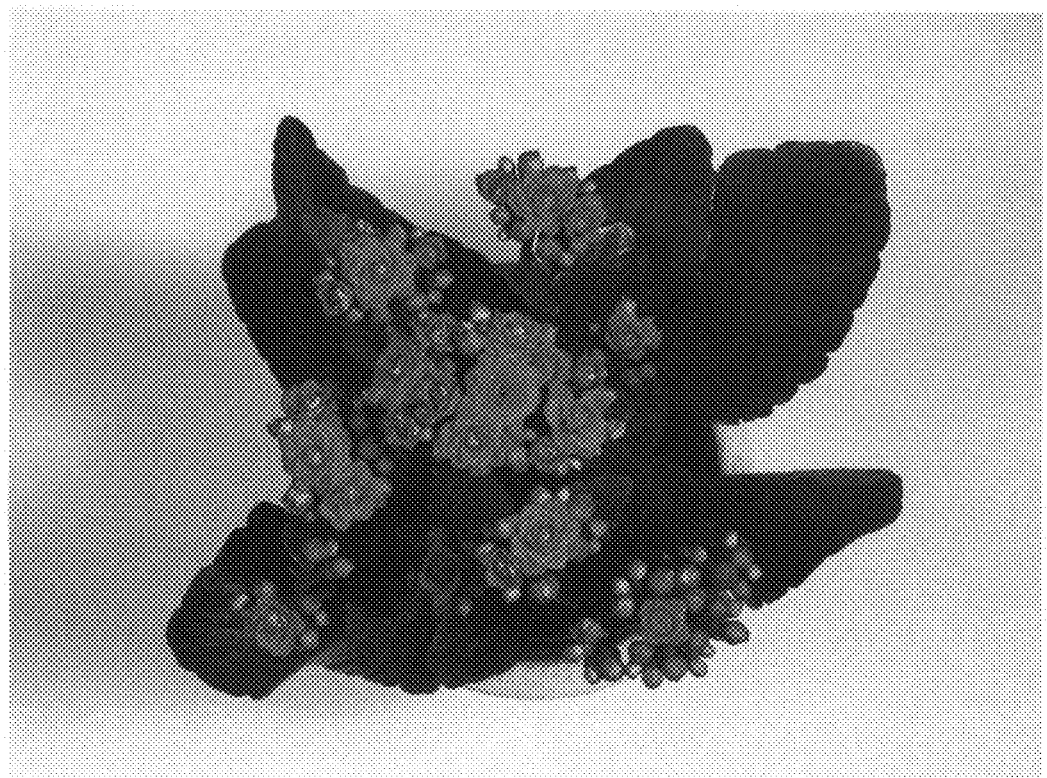

FIG. 13. A top perspective view of a typical potted flowering plant of *Kalanchoe* cultivar 'KJ 2003 00727' 19 weeks after planting of cutting.

Figure 14:

FIG. 14. A side perspective view of a typical potted flowering plant of *Kalanchoe* cultivar 'KJ 2003 0727' 19 weeks after planting of cutting.

Figure 15:
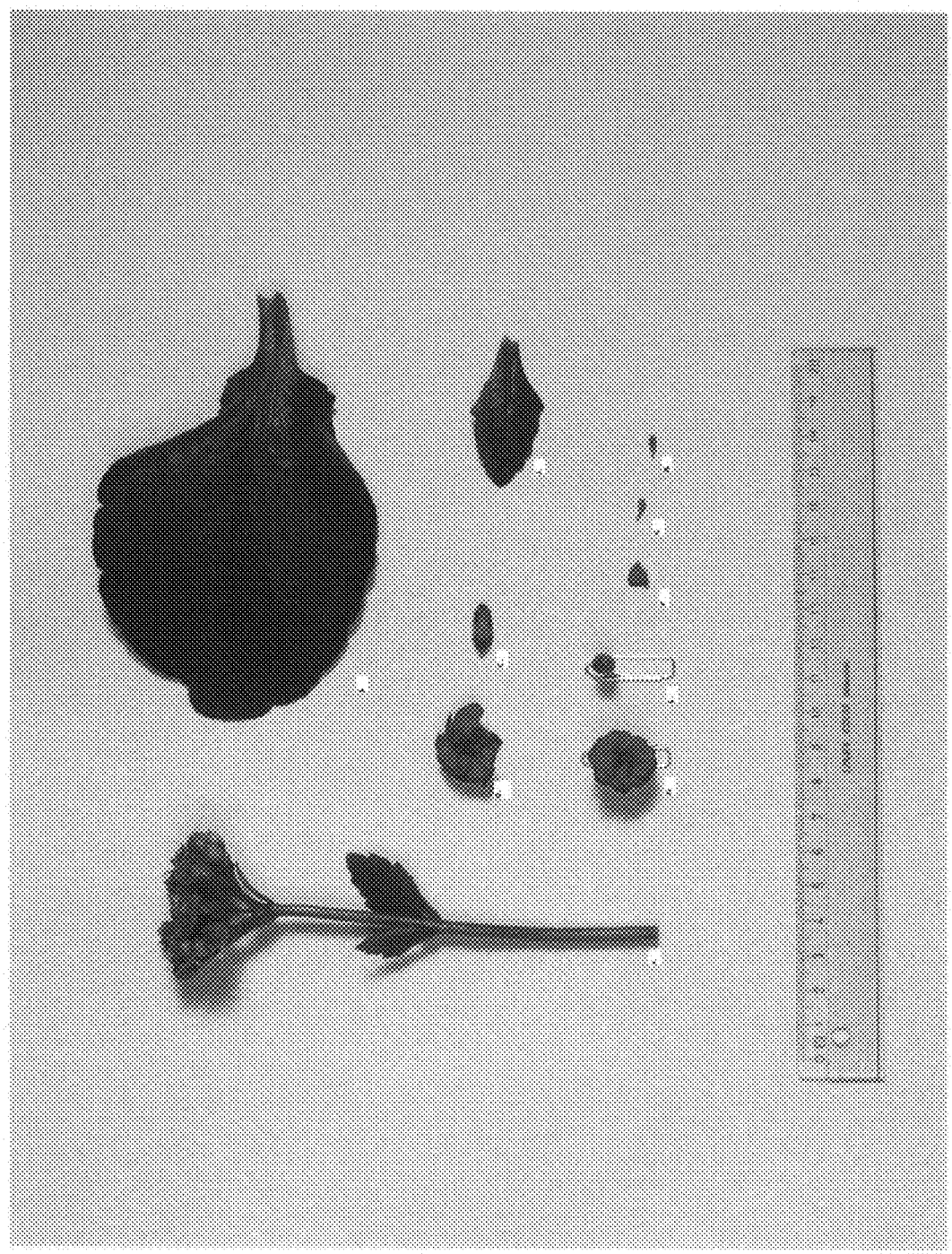

FIG. 15. Representative plant parts of *Kalanchoe* cultivar 'KJ 2003 0727': A. Inflorescence; B. Inside a flower; C. Flower bud, site; D. Flower; E. Flower bud, top; F. Petal; G. Pistil; H. Sepal; I. Mature leaf; J. Young leaf.

Figure 16:
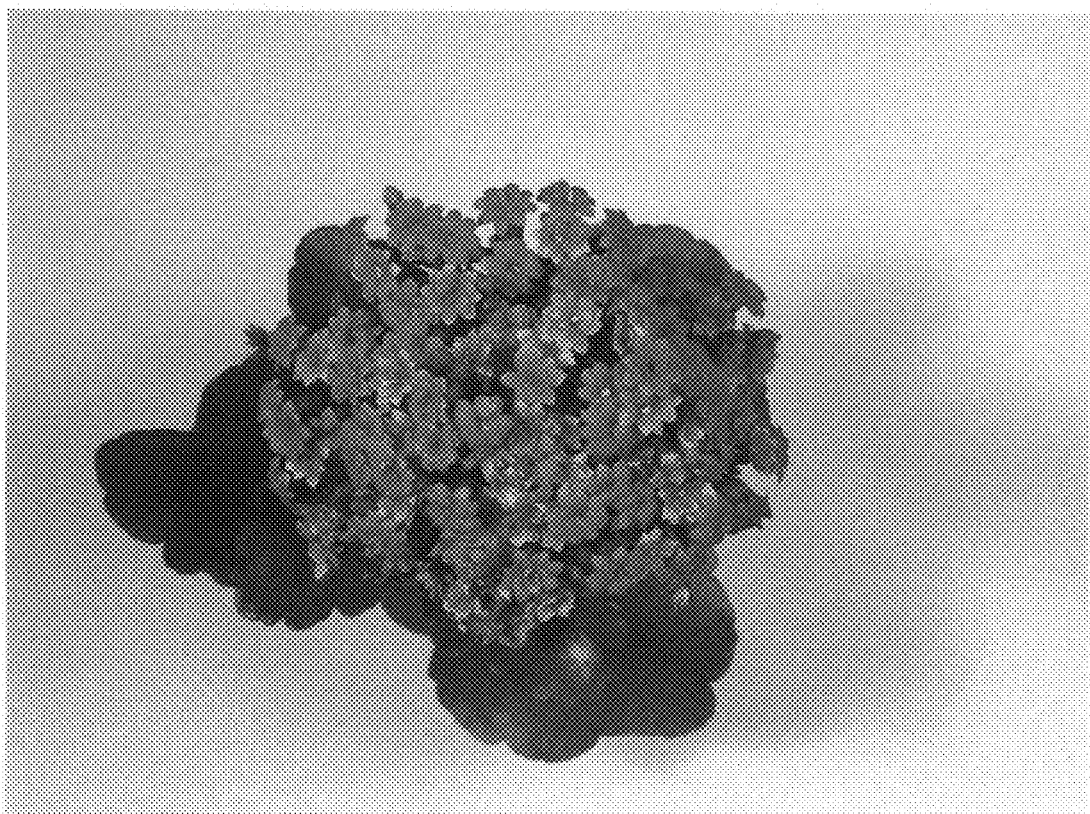

FIG. 16. A top perspective view of a typical potted flowering plant of *Kalanchoe* cultivar 'KJ 2004 0722' 16 weeks after planting of cutting.

Figure 17:

FIG. 17. A side perspective view of a typical potted flowering plant of *Kalanchoe* cultivar 'KJ 2004 0722' 16 weeks after planting of cutting.

Figure 18:
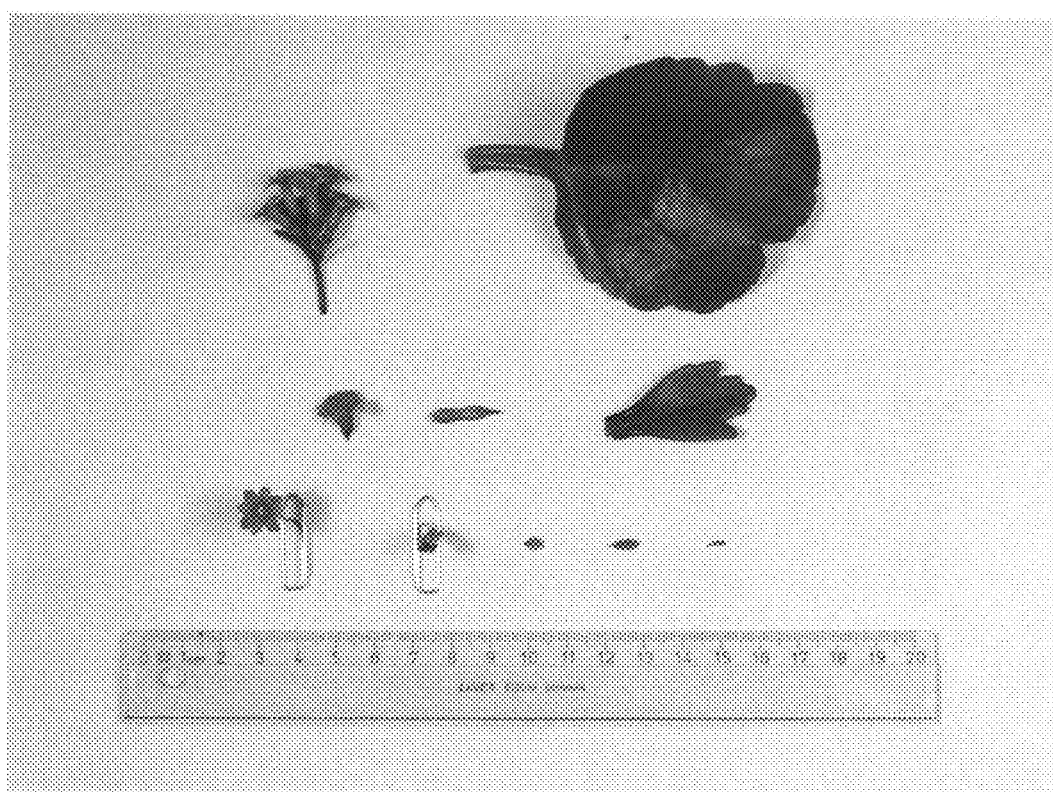

FIG. 18. Representative plant parts of *Kalanchoe* cultivar 'KJ 2004 0722': A. Inflorescence; B. Flower, just opened; C. Flower, opened one week; D. Color of a faded flower; E. Flower bud from the top; F. Inside a flower; G. Flower bud from the site; H. Petal; I. Sepal; J. Pistil; K. Mature leaf and L. Young leaf.

Figure 19:
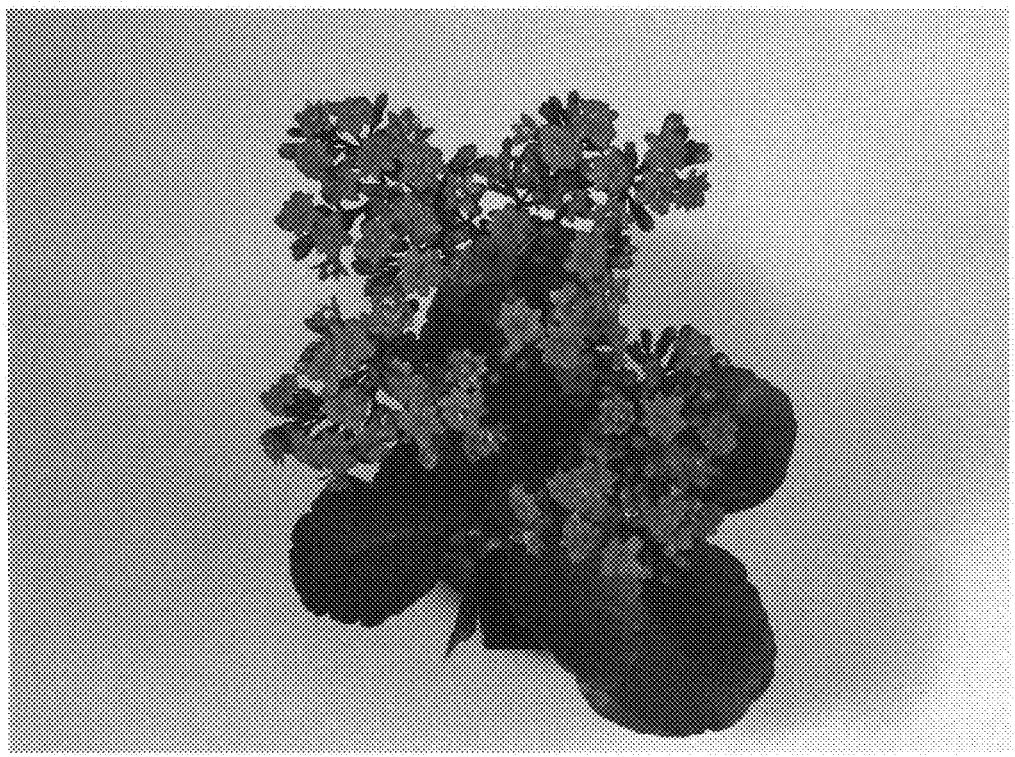

FIG. 19. A top perspective view of a typical potted flowering plant of *Kalanchoe* cultivar 'KJ 2004 0723' 16 weeks after planting of cutting.

Figure 20:

FIG. 20. A side perspective view of a typical potted flowering plant of *Kalanchoe* cultivar 'KJ 2004 0723' 16 weeks after planting of cutting.

Figure 21:
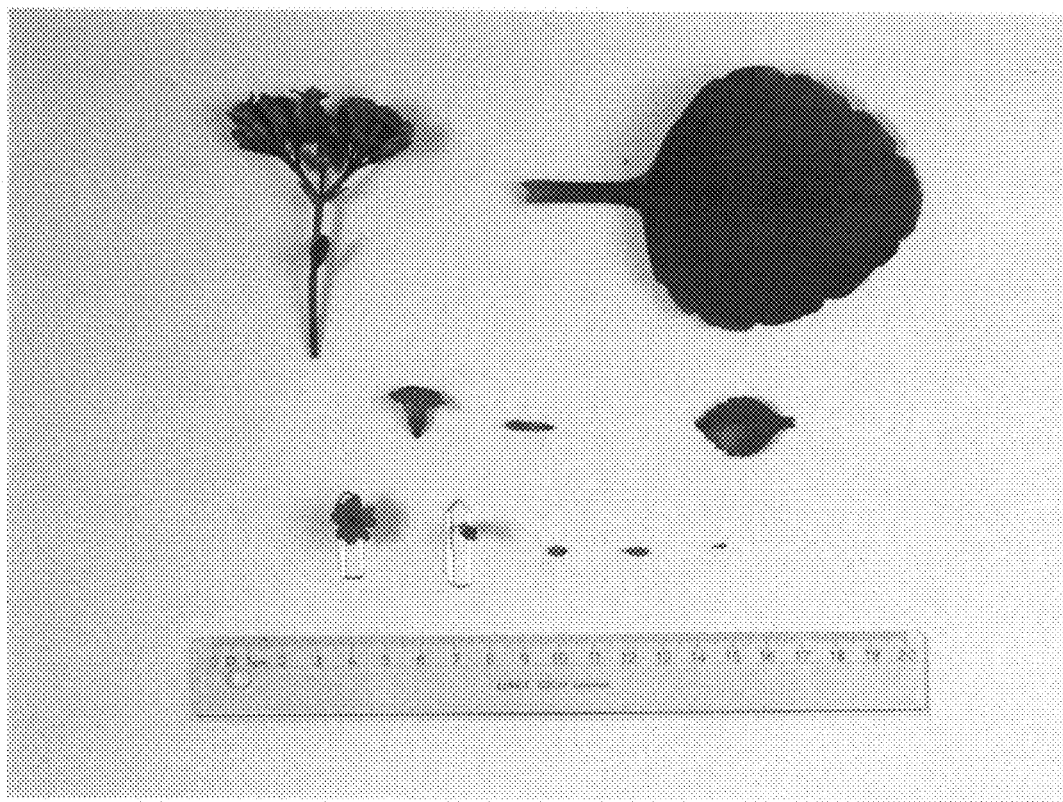

FIG. 21. Representative plant parts of *Kalanchoe* cultivar 'KJ 2004 0723': A. Inflorescence; B. Flower, just opened; C. Flower, opened one week; D. Color of a faded flower; E. Flower bud from the top; F. Inside a flower; G. Flower bud from the site; H. Petal; I. Sepal; J. Pistil; K. Mature leaf and L. Young leaf.

Figure 22:
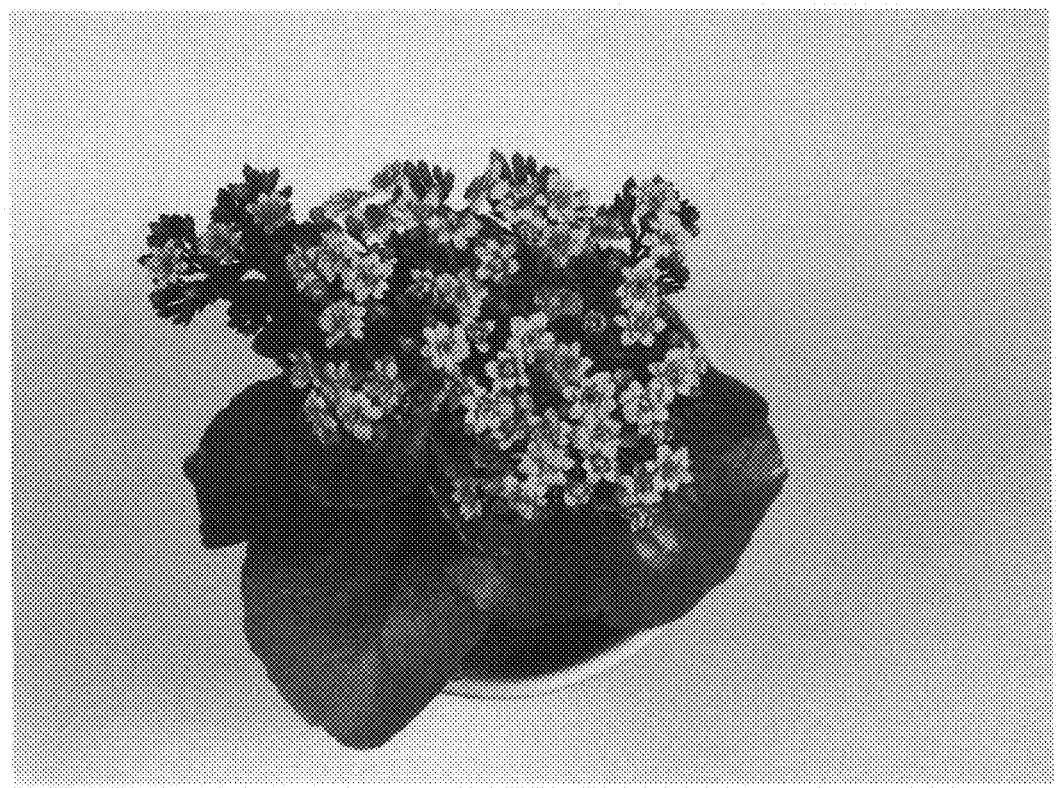

FIG. 22. A top perspective view of a typical potted flowering plant of *Kalanchoe* cultivar 'KJ 2004 0724' 16 weeks after planting of cutting.

Figure 23:
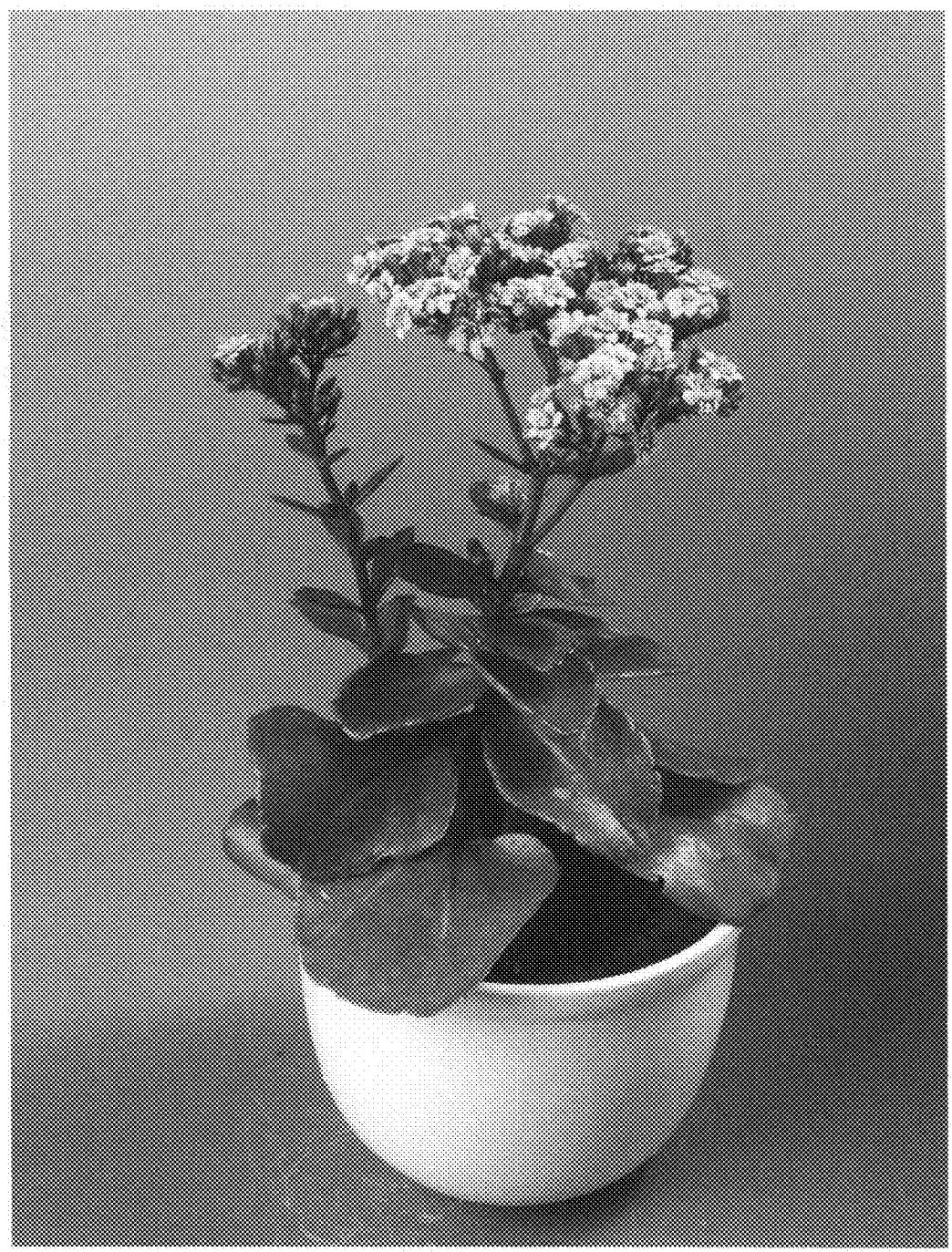

FIG. 23. A side perspective view of a typical potted flowering plant of *Kalanchoe* cultivar 'KJ 2004 0724' 16 weeks after planting of cutting.

Figure 24:
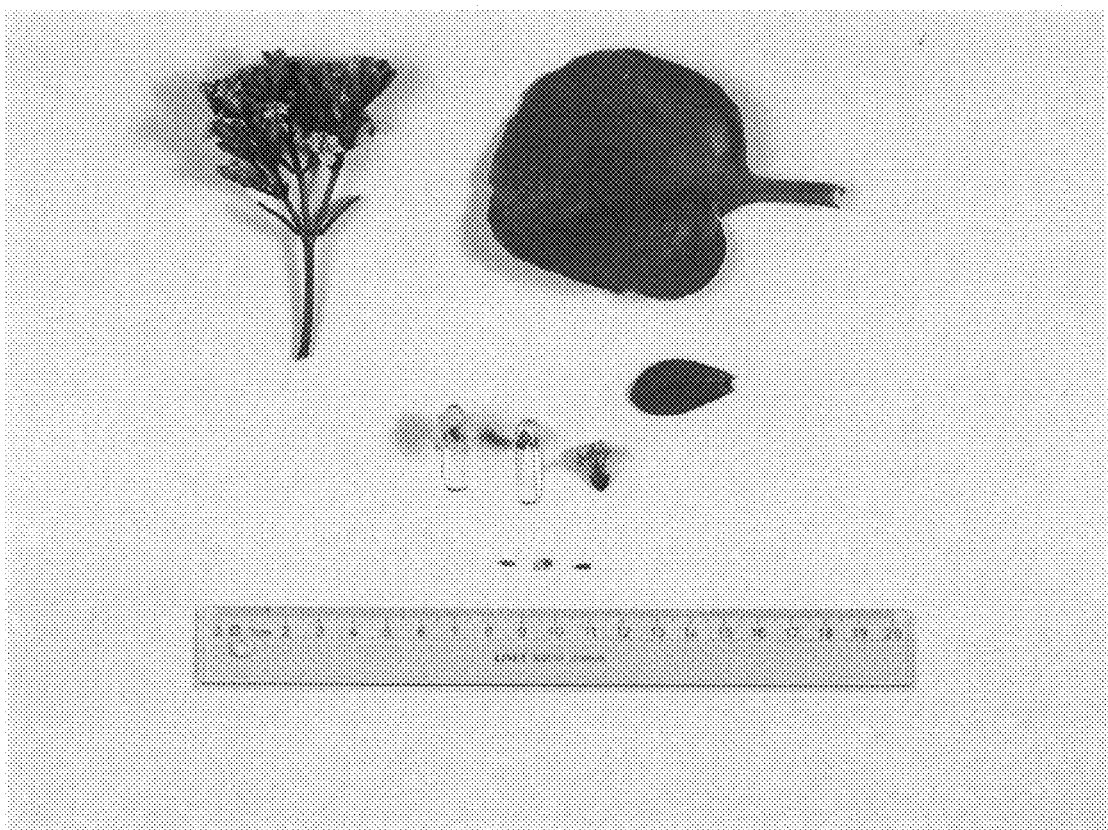

FIG. 24. Representative plant parts of *Kalanchoe* cultivar 'KJ 2004 0724': A. Inflorescence; B. Flower, just opened; C. Flower, opened one week; D. Color of a faded flower; E. Flower bud from the top; F. Inside a flower; G. Flower bud from the site; H. Petal; I. Sepal; J. Pistil; K. Mature leaf and L. Young leaf.

Figure 25:

FIG. 25. A top perspective view of a typical potted flowering plant of *Kalanchoe* cultivar 'KJ 2004 1122' 16 weeks after planting of cutting.

Figure 26:

FIG. 26. A side perspective view of a typical potted flowering plant of *Kalanchoe* cultivar 'KJ 2004 1122' 16 weeks after planting of cutting.

Figure 27:
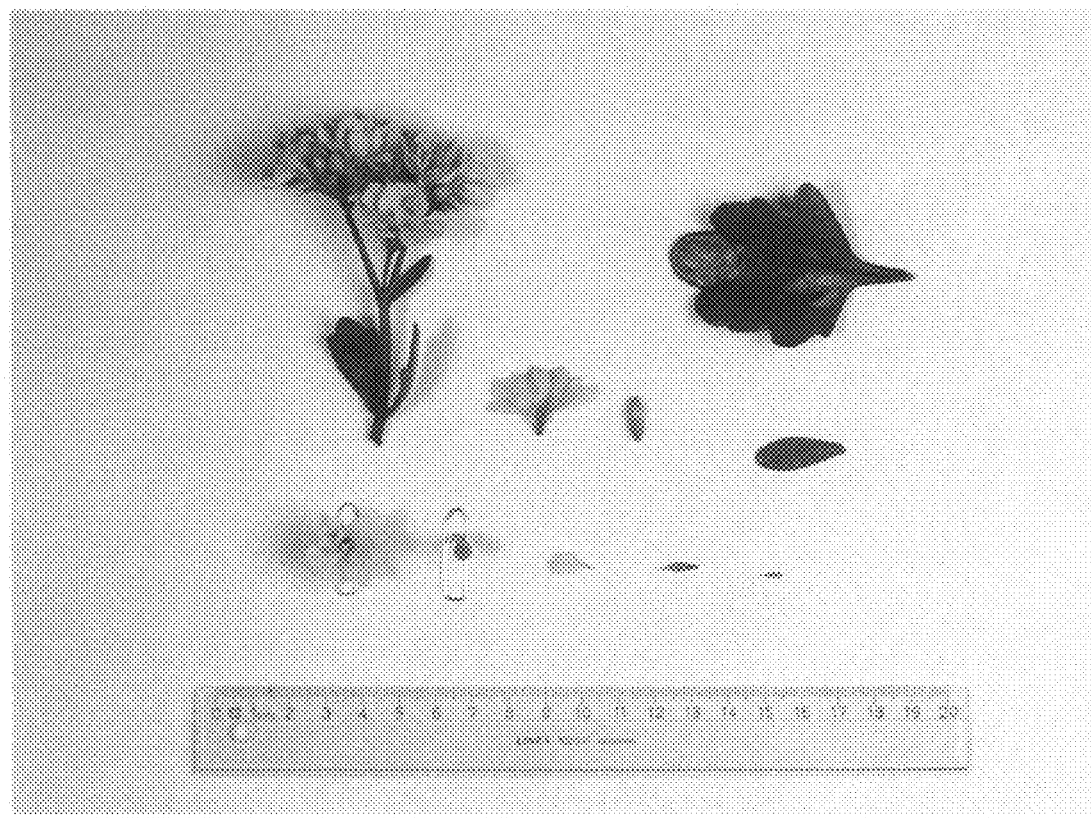

FIG. 27. Representative plant parts of *Kalanchoe* cultivar 'KJ 2004 1122': A. Inflorescence; B. Flower, just opened; C. Flower, opened one week; D. Color of a faded flower; E. Flower bud from the top; F. Inside a flower; G. Flower bud from the site; H. Petal; I. Sepal; J. Pistil; K. Mature leaf and L. Young leaf.

Figure 28:
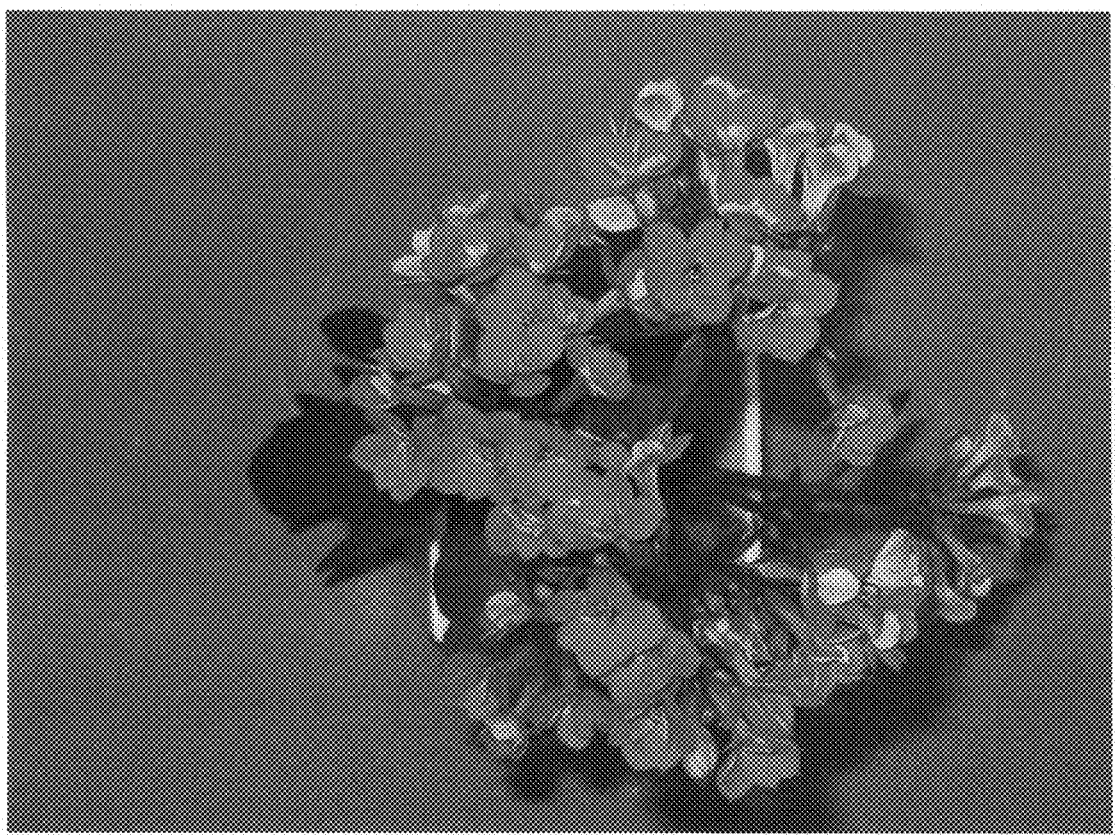

FIG. 28. A top perspective view of a typical potted flowering plant of *Kalanchoe* cultivar 'KJ 2005 0159' 16 weeks after planting of cutting.

Figure 29:

FIG. 29. A side perspective view of a typical potted flowering plant of *Kalanchoe* cultivar 'KJ 2005 0159' 16 weeks after planting of cutting.

Figure 30:
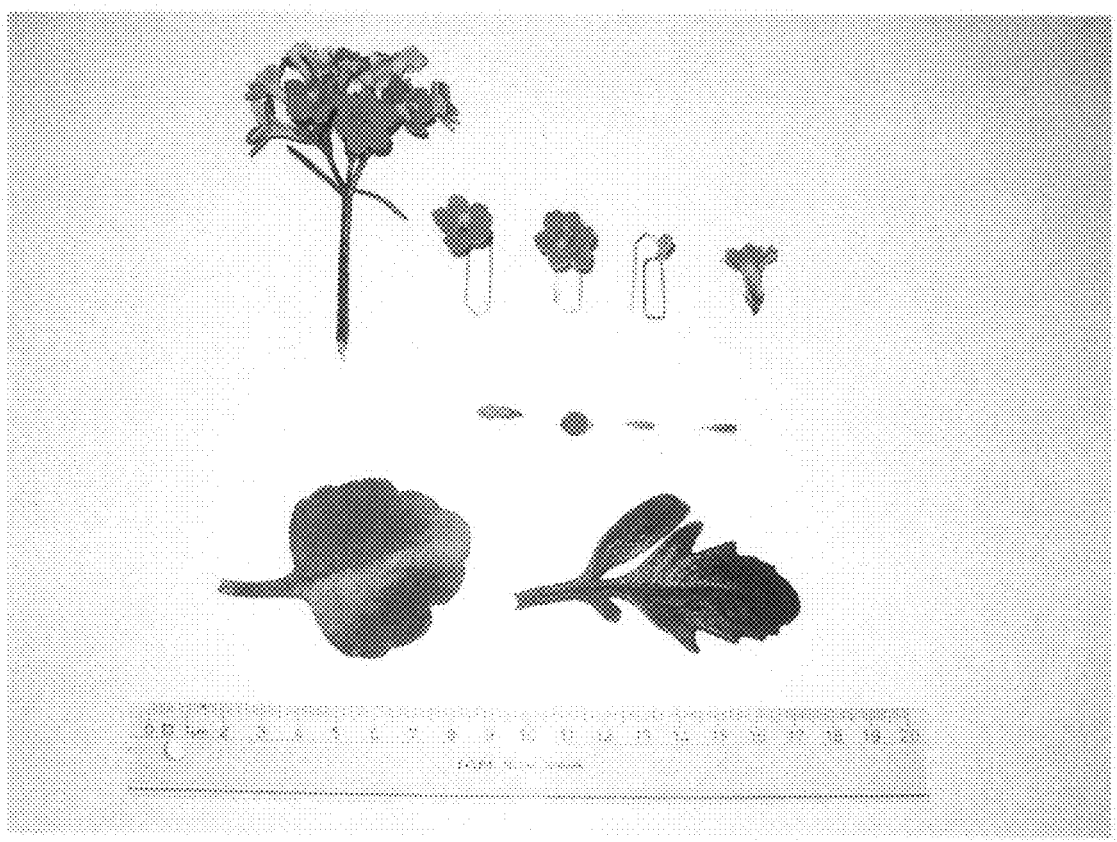

FIG. 30. Representative plant parts of *Kalanchoe* cultivar 'KJ 2005 0159': A. Inflorescence; B. Flower, just opened; C. Flower, opened one week; D. Flower bud from the top; E. Inside a flower; F. Flower bud from the site; G. Petal; H. Sepal; I. Pistil; J. Mature leaf and K. Young leaf.

DETAILED DESCRIPTION

As used herein, "single", or "single-flowering", or "single-type" are each defined as the typical *Kalanchoe* plant which produces flowers having 4 petals per flower.

As used herein, "double", "double-flowering", or "double-type" are each defined as a *Kalanchoe* interspecific hybrid plant which produces one or more flowers having at least 5 full or partial petals per flower. Preferably, the double-type Kalanchoe interspecific hybrid plant of the instant invention has substantially all double-type flowers. The double-type flowers of the instant invention have about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more than 40 petals per flower. A double-type *Kalanchoe* interspecific hybrid plant of the instant invention may produce flowers with a relatively uniform number of petals per flower and this characteristic is stable through asexual reproduction. Alternatively, a double-type *Kalanchoe* interspecific hybrid plant of the instant invention may produce flowers with a wide range in the number of petals per flower and this characteristic is also stable through asexual reproduction.

As used herein, the "degree of doubleness per flower" is defined as a measure of the number of extra full or partial petals per flower produced beyond the number 4 normally found on *Kalanchoe* single-type plant. The greater the degree of doubleness per flower, the greater the number of full or partial petals produced per flower.

As used herein "the degree of doubleness per plant" is defined as a measure of the number of flowers per plant, which have at least 5 petals per flower. The greater the degree of doubleness per plant, the higher is the percentage of total flowers produced by the plant which have at least 5 full or partial petals per flower.

As used herein, "interspecific hybrid" includes the progeny from the cross of two different species of *Kalanchoe*, as well as progeny resulting from subsequent backcrossing to one of the parents. This backcrossing to one of the parents may be conducted one or more times with the goal of stably combining the double-type trait with desired characteristics.

*K. blossfeldiana* can be crossed with numerous other *Kalanchoe* species to combine advantageous characteristics into unique new cultivars. Among the numerous interspecific hybrids that may be created are *K. blossfeldiana*×*K. laciniata, K. blossfeldiana*×*K. rotundifolia, K. blossfeldiana*×*K. aromatica, K. blossfeldiana*×*K. pubescens, K. blossfeldiana*×*K. grandiflora, K. blossfeldiana*×*K. citrina, K. blossfeldiana*×*K. ambolensis, K. blossfeldiana*×*K. faustii, K. blossfeldiana*×*K. schumacherii, K. blossfeldiana*×*K. pritwitzii, K. blossfeldiana*×*K. flammea, K. blossfeldiana*×*K. figueredoi, K. blossfeldiana*×*K. rauhii, K. blossfeldiana*×*K. obtusa, K. blossfeldi-*

*ana*×*K. pumila, K. blossfeldiana*×*K. marmorata, K. blossfeldiana*×*K. porphyrocalux, K. blossfeldiana*×*K. jongmansii, K. blossfeldiana*×*K. pinnata, K. blossfeldiana*×*K. diagremontiana, K. blossfeldiana*×*K. gracilipes, K. blossfeldiana*×*K. campanulata, K. blossfeldiana*×*K. latisepela, K. blossfeldiana*×*K. coccinea, K. blossfeldiana*×*K. fedtschenkoi, K. blossfeldiana*×*K. tubiflora, K. blossfeldiana*×*K. decumbens, K. blossfeldiana*×*K. manginii, K. blossfeldiana*×*K. orgyalis, K. blossfeldiana*×*K. crenata* and *K. blossfeldiana*×*K. tomentosa.*

Advantageous traits obtained from *K. aromatica* plants include: 1) excellent petal shape, 2) good foliage, 3) small size of foliage, 4) good branching habit, 5) fast growth habit, 6) good rooting habit, 7) numerous branched roots and 8) production of many cuttings. Traits from *K. aromatica* that a breeder generally attempts to avoid include: 1) small flower size, 2) petals bending back-wards 3) soft hanging stem, 4) hairy stem texture and 5) poor post-production longevity.

Advantageous traits obtained from *K. grandiflora* plants include: 1) yellow coloration of flower, 2) fragrance of flower, 3) rounded shape of leaf, 4) medium-sized leaf, 4) red coloration on the stem, 5) same red coloration on the margin of the leaves and 6) vigorous rooting habit. Traits from *K. grandiflora* that a breeder will attempt to avoid include: 1) too strongly built plant, 2) crispy leaf texture that breaks easily, 3) grayish leaf color, and 4) poor post-production longevity.

*K. pumila* plants may include such advantageous traits as: 1) pink-purple coloration of flower, 2) attractive petal shape; 3) small leaves, 4) pink coloration on the stem and 5) vigorous rooting habit. *K. pumila* plants may have traits that should be avoided in a breeding program include: 1) petals bending backward, 2) soft hanging stem, 3) grayish leaf color, 4) poor fixation of the leaf to the stem, 5) long petiole with a small diameter, 6) poor branching habit and 7) poor post-production longevity.

*K. marmorata* plants may include such advantageous traits as: 1) white coloration of flower, 2) large size of flower 3) good fixation of leaf to the stem, 4) strong upright growth and 5) vigorous rooting habit. *K. marmorata* plants may have traits that should be avoided in the breeding program include: 1) crispy leaf texture that breaks easily and 2) dreary green with yellow spots coloration of foliage.

Advantageous traits obtained from *K. porphyrocalux* plants include: 1) bell-shaped flower, 2) dark purple coloration of petal, 3) smooth texture of petal, 4) green leaf color, 5) small, harmonic, upright and compact growth habit, 6) good fixation of leaf to the stem and 7) production of many cuttings. Traits from *K. porphyrocalux* that should be avoided in breeding programs include: 1) poor branching habit and 2) weak growth habit.

Advantageous traits obtained from *K. jongmansii* plants include: 1) yellow coloration of flower, 2) upright, bell-shaped flower, 3) small size of foliage, 4) strong stem, 5) vigorous rooting habit and 6) production of many cuttings. Traits from *K. jongmansii* that should be avoided in breeding programs include: 1) open flower shape, 2) vigorous and delicate plant growth habit, 3) small size of foliage, 4) small creeping growth habit and 5) poor post-production longevity.

*K. pinnata* plants may have advantageous traits including: 1) large, bell-shaped flower, 2) ornamental shape of fused sepals, 3) red coloration of the stem, 4) same red coloration on the leaf margin and the middle vein, 5) very strong, upright growth habit and 6) vigorous rooting habit. *K. pinnata* that should be avoided in a breeding program: include 1) white spotting on the stems, 2) grayish leaf color, 3) poor branching habit, 4) poor production of cuttings and 5) poor post-production longevity.

Advantageous traits obtained from *K. laciniata* plants include: 1) intense yellow coloration of flower 2) entire, sinuate or parted leaf, 3) shinning texture of leaf 4) good fixation of the leaf to the stem, 5) production of many cuttings and 6) vigorous rooting habit. Traits from *K. laciniata* that should be avoided in a breeding program include 1) long length of stem, 2) fast and unstable growth habit and 3) poor post-production longevity.

*K. diagremontiana* plants may have advantageous traits including: 1) long, bell-shaped flowers 2) pink coloration of flower, 3) green color of leaf, 4) lanceolate shape of leaf, 5) red coloration of margin of leaf, 6) shinning texture of leaf and 7) strong, upright growth habit. *K. diagremontiana* traits that should be avoided in breeding program include: 1) pink coloration on only ⅓ of petal, 2) long length of stem which places inflorescence high above top of plant, 3) marbling of underside of leaf, 4) crispy leaf texture which breaks easily, 5) tall growth habit, and 6) poor post-production longevity.

*K. citrina* plants may include such advantageous traits as: 1) intense yellow coloration of flower, 2) small size of leaves, 3) short length of petiole, 4) green leaf color, 5) fine shape of inflorescence 6) sturdy fixation of leaf to the stem 7) good branching habit, and 8) vigorous rooting habit. *K. citrina* plants may have traits that should be avoided in a breeding program which include: 1) hairy leaf texture, 2) tall growth habit, 3) small flower size, and 4) poor post-production longevity.

Advantageous traits obtained from *K. faustii* plants include: 1) up-right bell-shaped flower, 2) yellow coloration of petal, 3) smooth texture of petal, 4) upright and strong growth habit 5) sturdy fixation of leaf to the stem, and 6) vigorous rooting habit. Traits from *K. faustii* that should be avoided in breeding programs include: 1) very poor branching habit, 2) large size of leaves, 3) small flower size, 4) grayish coloration of leaves, 5) very tall growth habit, and 6) poor post-production longevity.

Advantageous traits obtained from *K. pritwitzii* plants include: 1) up-right bell-shaped flower, 2) soft creamy white coloration of petal, 3) smooth texture of petal, 4) sturdy fixation of leaf to the stem, and 5) vigorous rooting habit. Traits from *K. pritwitzii* that should be avoided in breeding programs include: 1) very poor branching habit, 2) large size of leaves, 3) small flower size, 4) grayish coloration of leaf, 5) very tall growth habit, and 6) poor post-production longevity.

Advantageous traits obtained from *K. schumacherii* plants include: 1) large flower size, 2) dark yellow coloration of petal, 3) smooth texture of petal, 4) upright and strong growth habit 5) sturdy fixation of leaf to the stem, and 6) vigorous rooting habit. Traits from *K. schumacherii* that should be avoided in breeding programs include: 1) very poor branching habit, 2) large size of leaves, 3) grayish and matte coloration of leaves, 4) very tall growth habit, and 5) poor post-production longevity.

Advantageous traits obtained from *K. gracilipes* plants include: 1) large bell-shaped flower, 2) orange-red coloration of petal, 3) smooth texture of petal, 4) small size of leaves, 5) dark green, shinning coloration of leaf, 6) good branching habit, and 7) good production of cuttings. Traits from *K. gracilipes* that should be avoided in breeding programs include: 1) poor branching habit, 2) large size of leaves, 3) poor fixation of leaf to the stem, 4) soft hanging stem, and 5) poor post-production longevity.

Advantageous traits obtained from *K. flammea* plants include: 1) flower fragrance, 2) medium size of flower, 3) dark red coloration of petal, 4) upright and strong growth habit 5) sturdy fixation of leaf to the stem, and 6) vigorous rooting habit. Traits from *K. flammea* that should be avoided in breeding programs include: 1) very poor branching habit, 2) large size of leaves, 3) bowl-shape of leaf, 4) vigorous growth habit and, 5) poor post-production longevity.

*K. figueredoi* plants may include such advantageous traits as: 1) attractive leaf patter, 2) small size of leaves, 3) medium length of petiole, 4) sturdy fixation of leaf to the stem 5) compared to other species this has a very short flowering reaction time. *K. figueredoi* plants may have traits that should be avoided in a breeding program which include: 1) very small size of flower, and 2) tall growth habit.

Advantageous traits obtained from *K. coccinea* plants include: 1) medium size of flower, 2) red coloration of petal, 3) upright and strong growth habit, 4) sturdy fixation of leaf to the stem, 5) flowers and leaves are very similar to *K. blossfeldiana*, and 6) vigorous rooting habit. Traits from *K. coccinea* that should be avoided in breeding programs include: 1) very large size of leaves, 2) vigorous growth habit, and 3) poor post-production longevity.

*K. fedtschenkoi* plants may have advantageous traits including: 1) long, bell-shaped flowers 2) pink coloration of flower, 3) colorful red leaf margin, 4) matte texture of leaf, and 5) short growth habit. *K. fedtschenkoi* traits that should be avoided in breeding program include: 1) long length of stem which places inflorescence high above top of plant, 2) crisp, rigid leaf texture which breaks easily, 3) poor fixation of leaf to the stem, and 4) poor post-production longevity.

Advantageous traits obtained from *K. pubescens* and *K. campanulata* plants include: 1) large bell-shaped flower, 2) orange-red coloration of petal, 3) smooth texture of petal, 4) green leaf color, 5) harmonic, upright and strong growth habit, and 6) study fixation of leaf to the stem. Traits from *K. pubescens* and *K. campanulata* that should be avoided in breeding programs include: 1) poor branching habit, 2) large size of leaves and 3) poor post-production longevity.

Advantageous traits obtained from *K. rotundifolia* and *K. ambolensis* species include: 1) small size of foliage, 2) good branching habit, 4) vigorous growth habit, 5) good rooting habit, 6) numerous branched roots, 7) production of many cuttings, and 8) in relation to other *Kalanchoe* species, the reaction time is relatively short. Traits from *K. rotundifolia* species that a breeder generally attempts to avoid include: 1) very small flower size, 2) fleshy leaves, and 3) poor post-production longevity.

*K. decumbens, K. manginii, K. orgyalis, K. crenata, K. tomentosa, K. rauhii, K. obtusa, K. latisepela* and *K. tubiflora* are *Kalanchoe* species which can be crossed with any of the other *Kalanchoe* species disclosed in this specification to yield new Kalanchoe hybrids expressing new and unique phenotypes when compared to the Kalanchoe culture in general. For example, some of the new and unique phenotypes that may be expressed, include but are not limited to, larger flowers, bell-type flowers, unique flower color combination, smaller or larger leaves, change of leaf shape, and different growth habits, such as height, spread and vigor of Kalanchoe hybrid.

*K. blossfeldiana*×*K. laciniata* interspecific hybrids typically have leaves that are entire, sinuate or parted with erect and large flowers that are white, pink, purple, yellow, orange, and red. *K. blossfeldiana*×*K. laciniata* interspecific hybrids are highly branched, relatively compact and under certain conditions the height of the branches may be up to 30-45 cm.

*K. blossfeldiana*×*K. rotundifolia* interspecific hybrids typically have orbicular and elliptic leaves and relatively small flowers. *K. blossfeldiana*×*K. rotundifolia* interspecific hybrids are upright and have a uniform growth habit, and under certain conditions, the height of the branches may be up to 35 cm.

*K. blossfeldiana*×*K. aromatica* interspecific hybrids typically have medium sized flowers and orbicular shaped leaves, with a tendency of bending downwards. *K. blossfeldiana*×*K. aromatica* interspecific hybrids are upright and have a uniform growth habit, and under certain conditions, the height of the branches may be up to 18 cm.

(*K. blossfeldiana*×*K. laciniata*) x. (*K blossfeldiana*×*K. pubescens*) double type interspecific hybrids typically have ovate, as well as, hastate leaves. (*K. blossfeldiana*×*K. laciniata*)×. (*K. blossfeldiana*×*K. pubescens*) interspecific hybrids are upright and have s uniform growth habit, and under certain conditions, the height of the branches may be up to 26 cm.

Double-type *Kalanchoe* interspecific hybrid cultivars are genetically stable, as evidenced by the stability of the double-type trait through both asexual propagation and sexual crosses. The data from numerous crosses with *K. blossfeldiana* indicate that the double-type trait segregates as a single dominant gene. The double-type trait can be reproducibly and predictably introgressed into diverse Kalanchoe species and genetic backgrounds.

*K. blossfeldiana* seeds designated 'MP African' that produce plants carrying the double-type gene or trait, and which can be used as a male or female parent in crosses with Kalanchoe species to produce double-type *Kalanchoe* interspecific hybrid cultivars, were deposited on Dec. 9, 2004 at the American Type Culture Collection (ATCC), P.O. Box 1549, Manassas, Va. 20108, U.S.A., and accorded ATCC accession no. PTA-7896.

As a first step in making interspecific hybrids of the instant invention, a single or double-type *Kalanchoe* plant selection is crossed with a single-type Kalanchoe selection from another species. Progeny are screened for fertile selections. Large numbers of progeny may have to be screened to identify fertile selections. The fertile selections may be screened for those exhibiting the double-type flower trait if one of the parents was a double-type selection. Alternatively, the single-type fertile interspecific hybrid is crossed, either as the male or female parent, with a double-type Kalanchoe selection. A double-type hybrid progeny plant with desirable phenotypic characteristics is propagated asexually by conventional methods to determine if the phenotypic characteristics are stable.

For example, a *K. blossfeldiana* (tetraploid) x *K. laciniata* (diploid) interspecific hybrid is by nature triploid and thus sterile. *K. blossfeldiana*×*K. laciniata* interspecific hybrid progeny plants were screened and 'Yellow African', described in U.S. Plant Patent No. 12,299, was identified. This fertile *K. blossfeldiana*×*K. laciniata* interspecific hybrid has been used to breed a series of interspecific hybrid cultivars designated African Treasures™. One such cultivar was designated 'KJ 2000 0716' and is described in pending U.S. plant patent application Ser. No. 10/654,571, incorporated herein by reference.

'KJ 2000 0716' was identified in the progeny originating from a cross between 'Yellow African' and a single-type *K. blossfeldiana*. The three new double-flowered *Kalanchoe* interspecific hybrids described in Examples 2, 3 and 4 herein originated from crosses between 'KJ 2000 0716' as the female parent, and 'Monroe' as male double-type *K. blossfeldiana* parent. 'Monroe' is described in U.S. Plant Pat. No. 14,714.

Recurrent selection is used to increase the number of petals per flower found in the *Kalanchoe* interspecific hybrid plants of the instant invention. A double-type *Kalanchoe* interspecific hybrid plant is selfed, or crossed to another double-type *Kalanchoe* plant, and the progeny screened for plants with double-type flowers with an increased number of petals per flower compared to the double-type parents.

1. General Breeding Methods

The *Kalanchoe* plants of the instant invention were crossed as follows. When the pistil is fully developed and the anthers have not opened, the pistil is to some extent uncovered. During this time the stigma is susceptible to pollination. Pollen is harvested from the male using a pencil or small brush and transferred to the stigma. Once pollination is complete, the seeds develop within the ovary and the pistils are harvested when ripe. The seeds are dried before sowing in peat-based soil mix.

Breeding with double-type *K. blossfeldiana* requires careful uncovering of the pistil. It is very easy to wound the ovary and thereby hinder germination and development of seeds. In addition, if the female parent is water-stressed during pollination and subsequent seed development, the number of seeds obtained appear to increase.

2. Plant Growth Conditions

The *Kalanchoe* plants described herein were grown in a greenhouse at 64.4° F. during the day and 68° F. during the night. The plants were produced in pots with a diameter of 10.5 cm or 13 cm. Cuttings were grown under long-day conditions (16 hours light, 8 hours night) during the first 3-8 weeks following planting, depending on cultivar and pot size. Between 4-9 weeks after planting, the plants were transferred to short-day conditions (10 hour light and 14 hour dark). The flowering is induced by short-day conditions. Between 13-19 weeks after planting, depending on cultivar, pot size, and time of year, the plants were mature with flowers that were opening or about to open.

The plants were grown under natural light conditions supplemented with 70 μmol/m2/s SON-T light when the natural light was less than 100 μmol/m2/s. Plants were grown in a peat based soil mix and were watered with a solution containing 200 parts per million (ppm) nitrogen, 200 ppm potassium, 40 ppm phosphorous, 200 ppm calcium, 40 ppm magnesium, 60 ppm sulphate, 1 ppm iron, 0.6 ppm manganese, 0.1 ppm copper, 0.1 ppm zinc, 0.3 ppm borium, 0.03 ppm molybdenum.

The following examples are set forth as representative of the specific and preferred embodiments of the present invention. These examples are not to be construed as limiting the scope of the invention in any manner. It should be understood that many variations and modifications can be made while remaining within the spirit and scope of the invention.

EXAMPLE 1

The data from numerous crosses with *K. blossfeldiana* indicate that the double-type trait segregates as a single dominant gene. A total of 9,787 progeny from crosses of *K. blossfeldiana* double-type x *K. blossfeldiana* single-type have been analyzed. Among these 9,787 progeny, 2,956 exhibited the double-type trait. Seeds carrying the double-type trait germinate at a lower frequency than seeds carrying the single-type trait. This lower germination frequency has probably impacted the segregation pattern which is not the 1:1 ratio expected for a trait controlled by a single dominant gene. Regardless of what the genetic basis for control of the double-type trait in *Kalanchoe* might be, these data demonstrate the double-type trait can be reproducibly and predictably introgressed into diverse *Kalanchoe* genetic backgrounds.

EXAMPLE 2

Cultivar 'KJ 2003 0761'

The new *K. blossfeldiana*×*K. laciniata* interspecific hybrid 'KJ 2003 0761' was produced using a proprietary single-type selection of *K. blossfeldiana*×*K. laciniata* designated 'KJ 2000 0716', as the female parent. This female parent is described in pending U.S. plant patent application Ser. No. 10/654,571 and in European Union Community Variety Rights application serial No. 2003/0974, and is the second generation progeny of a fertile interspecific hybrid between *K. blossfeldiana* and *K. laciniata*. The male parent was a *K. blossfeldiana* double-type selection designated 'Monroe', and is described in U.S. Plant Patent No. PP 14,714. The new *Kalanchoe* cultivar 'KJ 2003 0761' was discovered and selected as a flowering plant within the progeny of the stated cross in a controlled environment in Hinnerup, Denmark.

Asexual reproduction of the new cultivar by vegetative terminal cuttings was first performed in February, 2004, in Hinnerup, Denmark, and has demonstrated that the combination of characteristics as herein disclosed for the new cultivar are firmly fixed and retained through successive generations of asexual reproduction. The new cultivar reproduces true-to-type through asexual reproduction.

The following traits have been repeatedly observed and are determined to be unique characteristics of the new *Kalanchoe* cultivar 'KJ 2003 0761' which in combination distinguish this Kalanchoe as a new and distinct cultivar:

1. large number of petals per flower resulting in a double-type trait;
2. the large size of petals resulting in a large flower;
3. the hastate, dissected leaves on young as well as mature leaves;
4. the intense sunny-yellow color of petals; and
5. the large number of flowers per plant.

The new *Kalanchoe* cultivar 'KJ 2003 0761' has not been observed under all possible environmental conditions. The phenotype of the new cultivar may vary significantly with variations in environment such as temperature, light intensity, and day length without any change in the genotype of the plant. The following observations, measurements and values describe the new *Kalanchoe* cultivar 'KJ 2003 0761' grown in Hinnerup, Denmark, under conditions which closely approximate those generally used in commercial practice.

Plants of 'KJ 2003 0761' differ from plants of the parental cultivars in the following characteristics:

| Trait | New Cultivar 'KJ 2003 0761' | Female Parent 'KJ 2000 0716' | Male Parent 'Monroe' |
|---|---|---|---|
| Height of cultivar | About 25 cm | About 38 cm | About 24 cm |
| Flower Type | Double-type | Single-type | Double-type |
| Flower Diameter | 18-22 mm | 20-25 mm | 16-19 mm |
| Flower number | 250-300 | 500 | 350-400 |
| Number of Corolla | Up to 16 full or partial | 4 | Up to 27 full or |

-continued

| Trait | New Cultivar 'KJ 2003 0761' | Female Parent 'KJ 2000 0716' | Male Parent 'Monroe' |
|---|---|---|---|
| Lobes | petals | | partial petals. |
| Corolla Coloration | From outer to center of flower: First circle Yellow, RHS 13D Next circle Yellow-orange, RHS 15D Center circle Yellow, RHS 13A Whole flower faints to light yellow-orange, RHS 21B | Red-orange, RHS 44B | Up to 27 full or partial petals |
| Shape of petal | The width of the petal is 7 mm. The length is 8 mm. The shape ovate with mucronate apex. | The width of the petal is 10 mm. The length is 13 mm. The shape is obovate with cuspidate tip. | The width of the petal is 4 mm. The length is 8 mm. The shape is ovate with cuspidate tip. |
| Leaf | Hastate, dissected leaves with a long petiole and long lamina. The leaf apex is obtuse and the base is cunate. | Hastate, dissected leaves with a long petiole and long lamina. The leaf apex is obtuse and the base is cunate. | Obovate leaves with obtuse leaf tips and truncate bases. The leaf margin is undulate. |
| Leaf texture | The foliage is glabrous and shinning both above and below. | The foliage is glabrous, and more shinning above than below. | The foliage is glabrous and shinning both above and below. |

Of the many commercial cultivars known to the present Inventors, the most similar in comparison to 'KJ 2003 0761' is parental cultivar 'KJ 2000 0716'. Comparing these two cultivars, the main distinction is the form and the color of the flower, as described in the preceding table.

In the following description, color references are made to the Royal Horticultural Society Colour Chart (RHS), published 1986, except where general colors of ordinary significance are used. Color values were taken under daylight conditions at approximately 12:00 p.m. in a greenhouse in Hinnerup, Denmark. The age of the plant described is 15 weeks (from the time the cutting was planted in growth medium to when the picture was taken).

Parentage:
Male or pollen parent: *K. blossfeldiana* cultivar 'Monroe' (disclosed in U.S. Plant Patent No. PP 14,714)
Female or seed parent: *K. blossfeldiana×K. laciniata* interspecific hybrid cultivar 'KJ 2000 0716' (disclosed in U.S. patent application Ser. No. 10/654,571)

Classification:
Botanical: *K. blossfeldiana×K. laciniata* interspecific hybrid cultivar 'KJ 2003 0761' (2nd generation after *K. blossfeldiana×K. laciniata* interspecific hybrid back-crossed with *K. blossfeldiana*).

PROPAGATION: Vegetative Terminal Cuttings.
Rooting Habit The cultivar has numerous, branched, fine and fibrous roots.
Time to initiate roots: It takes between one and two weeks to initiate roots.
Time to produce a rooted cutting: It will take three weeks to produce a well rooted cutting. In winter time, it can take on week more.

PLANT: If the plants are grown according to the description above, it will perform as described below. Variation from this description should be expected over the course of the year, and if the physical growing conditions varies from the description.

Growth habit: This cultivar is upright and uniform. The flowers are formed above the top of the leaf canopy, but the flowers will also appear between the leaves. The flowers are assembled in numerous compound inflorescences 'KJ 2003 0761' is freely flowering with numerous compound cymes.

Growth rate: Ready for sale after 16 weeks.

Branching habit and description: Freely branching; typically 8 to 12 lateral branches develop per plant. Pinching (removal of the terminal apex) is not mandatory, but will enhance lateral branching. When grown in 10 cm pots the cultivar is not pinched.

Height at flowering: The height of the cultivar is about 25 cm from the bottom of the pot to the top of the plant, depending on the growth conditions.

Spread/Diameter at flowering: The diameter of the cultivar at flowering is about 25 cm.

Stems:
Appearance: The cultivar has around 10 stems with none, one or numerous leaf pairs on the stem. The inflorescence on the top of the flower stem is branched giving an inverted triangle with a rounded crown. Each branch has between 30 and 70 flowers.
Aspect: The stem is strong.
Length: The length varies from 10 to 15 cm depending on growth conditions.
Texture: The texture of the stem is glabrous and shinning.
Color: The color of the stem is dark green, RHS 137 B.

Foliage:
Arrangement: The foliage is yellow-green with the same color of the immature as well as the mature leaf, RHS 147 A. The majority of the leaves are at the base of the plant, but immature leaves appear also on the flowering stem.
Overall Shape of Leaf: The leaves are defined as hastate, dissected leaves.
Apex: The form of the apex is obtuse.
Base: The form of the base is cunate.

Length: The length of the foliage varies from 6 cm for an immature leaf to 12 cm for a mature leaf.

Width: The width varies from 3 cm for an immature leaf to 9 cm for a mature leaf.

Margin: The foliage has a dentate margin.

Texture: The foliage is glabrous and shinning.

Color of Upper Surface:

Mature leaf: The color of the mature leaf is a dark yellow-green color, and is closely described with RHS 147 A, though it is a little greener.

Immature leaf: The immature leaf has the same color as the mature leaf, a dark yellow-green color, and is closely described with RHS 147 A, though it is a little greener.

Color of Lower Surface:

Mature leaf: The color of the lower surface is dark yellow-green and is closely describe with RHS 147 A.

Immature leaf: The immature leaf has the same color as the mature leaf and is defined with RHS 147 A.

Venation Color: There is no visual appearance of veins.

Upper surface: No difference between the color of venation and the rest of the leaf.

Lower surface: No difference between the color of venation and the rest of the leaf.

Petiole:

Length: The length of the petiole varies between an immature and mature leaf. The length of an immature leaf is about 0.75 cm. The length of a mature leaf is about 3 cm.

Diameter: The diameter of the petiole varies between an immature and mature leaf. The diameter of an immature leaf is 5 mm. The diameter of a mature leaf is 9 mm.

Color: Yellow-green, between RHS 147 A and 147 B.

Flower Description:

Flower type and habit: The flower is a double-type with up to 16 petals per flower. The average number of petals per flower is 12.

Natural flowering season: The flowering season is year round, when grown according to description above. When planting outside the flowering season will be in the summer (April to October), depending on local climatic conditions.

Time to flower: The time from start of short day treatment to 1st flower is about 66 days, approximately 1 week longer in winter time.

Flowering stem length: The length of the flowering stem is ranging from 13 to 14 cm depending on the growth conditions.

Post-production longevity: 'KJ 2003 0761' maintains good leaf and flower display for at least 6 weeks under interior environmental conditions.

Winter Hardiness/weather tolerance: 'KJ 2003 0761' withstands wind, rain and direct sunlight, and can cope with temperatures between 40 and 95 degrees F.

Fragrance: 'KJ 2003 0761' has no fragrance.

Flower size: The diameter of the flower range from 18 to 22 mm.

Overall shape: The shape is rose-like, defined by at least 5 petals per flower.

Quantity: The cultivar produces a large number of flower ranging from 250 to 300 flowers per plant.

Bud:

Rate of opening: From the bud is showing color the flower will open within 10 days.

Color: The color of the bud is yellow-green, RHS 145 B.

Shape: The shape of the bud is ellipsoidal with the smallest diameter toward the base.

Length: The length of the bud is about 1.3 cm.

Diameter: The diameter of the bud is about 3 mm at the base and about 5 mm at the top.

Petal:

Quantity: Typically 13-16 petals fused at the base.

Shape: The shape of petal is oval.

Length: The length is about 7 mm.

Width: The width is about 8 mm.

Apex: The shape of the apex is mucronate.

Margin: The shape of the margin can be described as entire.

Texture: The texture of the petals is soft, smooth and matte.

Color when opening:
  Upper surface: The upper surface of the petal is yellow-orange, RHS 17 C.
  Lower surface: The lower surface of the petal is yellow-orange, RHS 16A, with a twist of orange-red, RHS 30 D.

Color when fully open:
  Upper surface: The upper surface of the petal is yellow-orange, RHS 15 A.
  Lower surface: The lower surface the petal is yellow-orange, RHS 16 A, with a twist of orange-red, RHS 30 D.

Sepal:

Quantity: Typically 4 sepals fused at the base.

Shape: The shape of sepal is lineal lanceolate.

Length: The length is 11 mm.

Width: The width is 2 mm.

Apex: The shape of the apex is acute.

Margin: The shape of the margin is entire.

Texture: The texture of the sepals is glabrous and shinning.

Color when opening:
  Upper surface: The upper surface of the sepal is green, close to RHS 146 A, but a little greener.
  Lower surface: The lower surface of the sepal is green, close to RHS 146A, but a little greener.

Color when fully open:
  Upper surface: The upper surface of the sepal is green, close to RHS 146 A, but a little greener.
  Lower surface: The lower surface the sepal is green, close to RHS 146 A, but a little greener.

Peduncle description:

Length: Every flower has a peduncle with a length of 3 mm.

Color: The peduncle is dark green, RHS 137 B.

Texture: The peduncle is glabrous and shinning.

Reproductive Organs:

Stamen:

Number: The flower has between 8 and 12 ten stamens.

Color: The color of the stamens is greyed-orange, RHS 177B.

Anthers:

Number: The number of anthers is between 8 and 12.

Size: The size of 1 mm in length.

Color: The color of the anthers is yellow-brown, RHS 14B.

Filament Color: The color of the filament is yellow-green, RHS 145C.

Pollen Color The color of the pollen is yellow, RHS 17C.

Pollen Amount: A high amount of pollen with a high pollen fertility of 95%, depending on the time of year.

Pistil:

Number: The number of pistils is four.

Stigma:

Shape: The shape of stigma is round.

Color: The color of the stigma is yellow-green, RHS 145A.

Style:

Shape: The shape of the style is thin and cylindrical.

Color: The color of style is yellow-green, RHS 145 A.

Ovary:

Color: The color of ovary is yellow-green, best described between RHS 147A and 147B.

Seeds:
Number: Between 50 and 60 potential seeds per ovary.
Width: The width of the seeds is less than 0.5 mm.
Length: The length of the seeds is less than 1 mm.
Shape: The shape of the seeds is ellipsoidal.
Color: The color of the potential seeds is green, RHS 145 C.
Fruit (Ovary):
Shape: The shape of the fruit is cylindrical.
Width: The width of the fruit is 1 mm.
Length: The length of the fruit is 6 mm.
Color: The color of the fruit is yellow-green, RHS 145 A.
DISEASE/PEST RESISTANCE/SUSCEPTIBILITY: No information on disease or pest resistance or susceptibility is currently available.

EXAMPLE 3

Cultivar 'KJ 2003 0638'

The new *K. blossfeldiana*×*K. laciniata* interspecific hybrid 'KJ 2003 0638' was produced using a proprietary single-type selection of *K. blossfeldiana*×*K. laciniata* designated 'KJ 2000 0716', as the female parent. This female parent is described in pending U.S. plant patent application Ser. No. 10/654,571 and in European Union Community Variety Rights application serial No. 2003/0974, and is the second generation progeny of a fertile interspecific hybrid between *K. blossfeldiana* and *K. laciniata*. The male parent was a *K. blossfeldiana* double-type selection designated 'Monroe' and is described in U.S. Plant Patent No. PP14,714. The new Kalanchoe cultivar 'KJ 2003 0638' was discovered and selected as a flowering plant within the progeny of the stated cross in a controlled environment in Hinnerup, Denmark.

Asexual reproduction of the new cultivar by vegetative terminal cuttings was first performed in February, 2004, in Hinnerup, Denmark, and has demonstrated that the combination of characteristics as herein disclosed for the new cultivar are firmly fixed and retained through successive generations of asexual reproduction. The new cultivar reproduces true-to-type through asexual reproduction.

The following traits have been repeatedly observed and are determined to be unique characteristics of the new *Kalanchoe* cultivar 'KJ 2003 0638' which in combination distinguish this Kalanchoe as a new and distinct cultivar:

1. large number of petals per flower resulting in a double-type or multi-petalled trait;
2. large size of petals resulting in a large flower;
3. the hastate, dissected leaves on young as well as mature leaves;
4. the different soft-white and creamy colors of petals and
5. large number of flowers per plant.

The new *Kalanchoe* cultivar 'KJ 2003 0638' has not been observed under all possible environmental conditions. The phenotype of the new cultivar may vary significantly with variations in environment such as temperature, light intensity, and day length without any change in the genotype of the plant. The following observations, measurements and values describe the new *Kalanchoe* cultivar 'KJ 2003 0638' as grown in Hinnerup, Denmark, under conditions which closely approximate those generally used in commercial practice.

Plants of 'KJ 2003 0638' differ from plants of the parental cultivars in the following characteristics:

| Trait | New Cultivar 'KJ 2003 0638' | Female Parent 'KJ 2000 0716' | Male Parent 'Monroe' |
|---|---|---|---|
| Height of cultivar | About 31 cm | About 38 cm | About 24 cm |
| Flower Type | Double-type | Single-type | Double-type |
| Flower Diameter | 20-25 mm | 20-25 mm | 16-19 mm |
| Flower Number Per Plant | 250-300 | 500 | 350-400 |
| Number of Corolla Lobes | Up to 17 full or partial petals | 4 | Up to 27 full or partial petals |
| Corolla Coloration | From outer to center of flower: First circle Yellow-orange, RHS 20D Next circle Yellow-orange, RHS 19B Center circle Yellow-orange, RHS 20D with a twist of red, RHS 39C Whole flower faints to light orange RHS 27C | Red-orange, RHS 44B | White, RHS 155 D |
| Shape of petal | The width of the petal is 9 mm. The length is 6 mm. The shape is ovate with mucronate apex. | The width of the petal is 10 mm. The length is 13 mm. The shape is obovate with cuspidate tip. | The width of the petal is 4 mm. The length is 8 mm. The shape is ovate with cuspidate tip. |
| Leaf | Hastate, dissected leaves with a long petiole and long lamina. The leaf apex is obtuse and the base is cunate. | Hastate, dissected leaves with a long petiole and long lamina. The leaf apex is obtuse and the base is cunate. | Obovate leaves with obtuse leaf tips and truncate bases. The leaf margin is undulate. |

-continued

| Trait | New Cultivar 'KJ 2003 0638' | Female Parent 'KJ 2000 0716' | Male Parent 'Monroe' |
|---|---|---|---|
| Leaf texture | The foliage is glabrous and shinning both above and below. | The foliage is glabrous and more shinning above than below. | The foliage is glabrous and shinning both above and below. |

Of the many commercial cultivars known to the present Inventors, the most similar in comparison to 'KJ 2003 0638' is parental cultivar 'KJ 2000 0716'. Comparing these two cultivars, the main distinction is the form and the color of the flower, as described in the preceding table.

'KJ 2003 0638' has not been observed under all possible environmental conditions. The phenotype of the new cultivar may vary significantly with variations in environment such as temperature, light intensity, and day length without any change in the genotype of the plant.

The aforementioned photographs, together with the following observations, measurements and values describe the new *Kalanchoe* cultivar as grown in a greenhouse in Hinnerup, Denmark, under conditions which closely approximate those generally used in commercial practice.

In following description, color references are made to the Royal Horticultural Society Colour Chart (RHS), published 1986, except where general colors of ordinary significance are used. Color values were taken under daylight conditions at approximately 12:00 p.m. in a greenhouse in Hinnerup, Denmark. The age of the plant described is 15 weeks (from the time the cutting was planted in growth medium to when the picture was taken).

Parentage:
  Male or pollen parent: *K. blossfeldiana* cultivar 'Monroe' (disclosed in U.S. Plant Patent No. PP14,714)
  Female or seed parent: *K. blossfeldiana*×*K. laciniata* interspecific hybrid cultivar 'KJ 2000 0716' (disclosed in U.S. patent application Ser. No. 10/654,571)

Classification:
  Botanical: *K. blossfeldiana*×*K. laciniata* interspecific hybrid cultivar 'KJ 2003 0638' (2nd generation after *K. blossfeldiana*×*K. laciniata* interspecific hybrid back-crossed with *K. blossfeldiana*).

PROPAGATION: Vegetative Terminal Cuttings
  Rooting Habit: The cultivar has numerous, branched, fine and fibrous roots.
  Time to initiate roots: It takes between one and two weeks to initiate roots.
  Time to produce a rooted cutting: It will take three weeks to produce a well rooted cutting. In winter time, it can take one week more.

PLANT: If the plants are grown according to the description above, it will perform as described below. Variation from this description should be expected over the course of the year, and if the physical growing conditions varies from the description.

Growth Habit: This cultivar is upright and uniform. The flowers are formed above the top of the leaf canopy, but flowers will also appear between the leaves. The flowers are assembled in numerous compound inflorescences.
  Growth rate: Ready for sale after 16 weeks.
  Branching habit and description: Freely branching; typically 4 to 8 lateral branches develop per plant. Pinching (removal of the terminal apex) is not mandatory, but will enhance lateral branching. When grown in 10 cm pots the cultivar is not pinched.
  Height at flowering: The height of the cultivar is about 31 cm, from the bottom of the pot to the top of the plant, depending on growth conditions.
  Spread/Diameter at flowering: The diameter at flowering is about 30 cm.
  Stems:
    Appearance: The cultivar has around 8 stems with none, one or numerous leaf pairs on the stem. The inflorescence on the top of the flower stem is branched, giving an inverted triangle with a rounded crown. Each branch has between 40 and 60 flowers.
    Aspect: The stem is strong.
    Length: The length of the stem is about 14 cm depending on growth conditions.
    Texture: The texture of the stem is glabrous and shinning.
    Color: The color of the stem is yellow-green, RHS 146 A.
  Foliage:
    Arrangement: The foliage is yellow-green with the same colors of the immature as well as the mature leaf, RHS 146 A and RHS 147 A. The majority of the leaves are at the base of the plant, but immature leaves appear also on the flowering stem.
    Overall Shape of Leaf: The leaves are defined as hastate, dissected leaves.
    Apex: The form of the apex is obtuse.
    Base: The form of the base is cunate.
    Length: The length of the foliage varies from about 3 cm for an immature leaf to about 14 cm for a mature leaf.
    Width: The width varies from about 2 cm for an immature leaf to about 13 cm for a mature leaf.
    Margin: The foliage has a dentate margin.
    Texture: The foliage is glabrous and shinning both above and below.
    Color of Upper Surface:
      Mature leaf: The color of the mature leaf is dark yellow-green and is closely described with RHS 147 A.
      Immature leaf: The immature leaf has the same color as the mature leaf, dark yellow-green, described with RHS 147 A.
    Color of Lower Surface:
      Mature leaf: The color of the lower surface is different from the upper surface, and is closely described with a dark yellow-green color between RHS 146 A and RHS 147 A.
      Immature leaf: The immature leaf has the same color as the mature leaf, dark yellow-green, and is closely described with a dark yellow-green color between RHS 146 A and RHS 147 A.
    Venation Color: There is no visual appearance of veins.
      Upper surface: There is no difference between the color of venation and the rest of the leaf.
      Lower surface: There is no difference between the color of venation and the rest of the leaf.

Petiole:
Length: The length of the petiole varies between an immature and mature leaf. The length of an immature leaf varies between 0.5 and 1 cm. The length of a mature leaf varies between 3 and 3.5 cm.
Diameter: The diameter of petiole varies between an immature and mature leaf. The diameter of an immature leaf is 4 mm. The diameter of a mature leaf is 5 mm.
Color: There is no difference between the color of petiole and the rest of the leaf.

Flower Description:
Flower type and habit: The flower type is a double-type with 16 to 19 petals per flower. The average number of petals per flower is 17.

Natural flowering season: The flowering season is year round, when grown according to description above. When planting outside the flowering season will be in the summer (April to October), depending on local climatic conditions.

Time to flower: The time from start of short day treatment to 1$^{st}$ flower is about 74 days, approximately 1 week longer in winter time.

Flowering stem length: The length of the flowering stem is ranging from 13 to 14 cm depending on the growth conditions.

Post-production longevity: 'KJ 2003 0638' maintains good leaf and flower display for at least 6 weeks under interior environmental conditions.

Winter Hardiness/weather tolerance: 'KJ 2003 0638' withstands wind, rain and direct sunlight, and can cope with temperatures between 40 and 95 degrees F. Fragrance: 'KJ 2003 0638' has no fragrance.

Flower size: The diameter of the flower range from is 2.5 to 3 cm.

Overall shape: The shape is rose-like, defined by at least 5 petals per flower.

Quantity: The cultivar produces a large number of flower ranging from 200 to 250 flowers per plant.

Bud:
Rate of opening: From the bud is showing color the flower will open within 10 days.
Color: At the tip the bud is yellow-green, RHS 145 B, with a twist of orange 24 A. At the base the bud has the same yellow-green color, RHS 145B.
Shape: The shape of the bud is ellipsoidal with the smallest diameter towards the base.
Length: The length of the bud is about 1.5 cm.
Diameter: The diameter of the bud is about 8 mm at the tip and about 4 mm at the base.

Petal:
Quantity: Typically 16-17 fused at the base.
Shape: The shape of petal is oval.
Length: The length is about 9 mm.
Width: The width is about 6 mm.
Apex: The shape of apex is mucronate.
Margin: The shape of the margin can be described as entire.
Texture: The texture of the petals is soft, smooth and matte.
Color when opening:
  Upper surface: The color of the upper surface of the petals can be described as follows: Going from the outer circle to the inner circle of petals, the first circle of petals is yellow-orange, RHS 20 D, the next is yellow-orange, RHS 19 B, and the middle is yellow-orange, RHS 20 B, with a touch of red, RHS 39 C.
  Lower surface: The color of the lower surface of the petals is yellow-orange, RHS 23 D, with a touch of red, RHS 38 A.

Color when fully open:
  Upper surface: At maturity the upper surface of the whole flower fades to orange RHS 27 C.
  Lower surface: At maturity the lower surface of the whole flower fades to orange RHS 27 C.

Sepal:
Quantity: Typically 4 sepals fused at the base.
Shape: The shape of sepal is lanceolate.
Length: The length is 10 mm.
Width: The width is 3 mm.
Apex: The shape of the apex is acute.
Margin: The shape of the margin is entire.
Texture: The texture of the sepals is glabrous and shinning.
Color when opening:
  Upper surface: The upper surface of the sepal is green, RHS 137 B.
  Lower surface: The lower surface of the sepal is green, RHS 137 B.
Color when fully open:
  Upper surface: The upper surface of the sepal is green, RHS 137 B.
  Lower surface: The lower surface the sepal is green, RHS 137 B.

Peduncle:
Length: Every flower has a peduncle with a length of 5 mm.
Color: The peduncle is yellow-green; RHS 146 A.
Texture: The peduncle is glabrous and shinning.

Reproductive Organs:
Stamen:
Number: The flower has between 7 and 9 stamens.
Color: The color of the stamens is greyed-orange, RHS 177 B.
Anthers:
Number: The number of anthers is 7 and 9.
Size: The anthers are less than 1 mm in length.
Color: The color of the anthers is yellow-brownish, RHS 14 B.
Filament Color: The color of the filament is yellow-green, RHS 145 C.
Pollen Color: The color of the pollen is yellow, RHS 17 C.
Pollen Amount: A medium amount of pollen with very good pollen fertility of 100% depending on time of year.
Pistil:
Number: The number of pistils is four.
Stigma:
Shape: The shape of the stigma is round.
Color: The color of the stigma is yellow-green, RHS 145 A.
Style:
Shape: The shape of the style is thin and cylindrical.
Color: The color of the style is yellow-green, RHS 145 A.
Ovary:
Color: The color of ovary is green, RHS 144 B.
Seeds:
Number: Between 50 and 60 potential seeds per ovary.
Width: The width of the seeds is less than 0.5 mm.
Length: The length of the seeds is less than 1 mm.
Shape: The shape of the seeds is ellipsoidal.
Color: The color of the potential seeds is green, RHS 145 C.
Fruit (Ovary):
Shape: The shape of the fruit is cylindrical.
Width: The width of the fruit is 1 mm.
Length: The length of the fruit is 6 mm.
Color: The color of the fruit is yellow green, RHS 145 A.

DISEASE/PEST RESISTANCE/SUSCEPTIBILITY: No information on disease or pest resistance or susceptibility is currently available.

EXAMPLE 4

Cultivar 'KJ 2003 0747'

The new *K. blossfeldiana×K. laciniata* interspecific hybrid 'KJ 2003 0747' was produced using a proprietary single-type selection of *K. blossfeldiana×K. laciniata* designated 'KJ 2000 0716', as the female parent. This female parent is described in pending U.S. plant patent application Ser. No. 10/654,571 and in European Union Community Variety Rights application serial No. 2003/0974, and is the second generation progeny of a fertile interspecific hybrid between *K. blossfeldiana* and *K. laciniata*. The male parent was a *K. blossfeldiana* double-type selection designated 'Monroe' and is described in U.S. Plant Patent No. PP14,714. The new Kalanchoe cultivar 'KJ 2003 0747' was discovered and selected as a flowering plant within the progeny of the stated cross in a controlled environment in Hinnerup, Denmark.

Asexual reproduction of the new cultivar by vegetative terminal cuttings was first performed in February, 2004, in Hinnerup, Denmark, and has demonstrated that the combination of characteristics as herein disclosed for the new cultivar are firmly fixed and retained through successive generations of asexual reproduction. The new cultivar reproduces true-to-type through asexual reproduction.

The following traits have been repeatedly observed and are determined to be unique characteristics of the new *Kalanchoe* cultivar 'KJ 2003 0747' which in combination distinguish this Kalanchoe as a new and distinct cultivar:

1. large number of petals per flower resulting in a double-type or multi-petalled trait;
2. large size of petals resulting in a large flower;
3. hastate, dissected leaves on young as well as mature leaves;
4. the different yellow and soft-white colors of petals and
5. large number of flowers per plant.

The new *Kalanchoe* cultivar 'KJ 2003 0747' has not been observed under all possible environmental conditions. The phenotype of the new cultivar may vary significantly with variations in environment such as temperature, light intensity, and day length without any change in the genotype of the plant. The following observations, measurements and values describe the new *Kalanchoe* cultivar 'KJ 2003 0747' as grown in Hinnerup, Denmark under conditions which closely approximate those generally used in commercial practice.

Plants of 'KJ 2003 0747' differ from plants of the parental cultivars in the following characteristics:

| Trait | New Cultivar 'KJ 2003 0747' | Female Parent 'KJ 2000 0716' | Male Parent 'Monroe' |
| --- | --- | --- | --- |
| Height of Cultivar | About 31 cm | About 38 cm | About 24 cm |
| Flower Type | Double-type | Single-type | Double-type |
| Flower Diameter | 20-25 mm | 20-25 mm | 16-19 mm |
| Flower Number Per Plant | 250-300 | 500 | 350-400 |
| Number of Corolla Lobes | Up to 25 full or partial petals | 4 | Up to 27 full or partial petals |
| Corolla Coloration | From outer petals to center of flower: First circle Yellow, RHS 13D Next circle Yellow-orange, RHS 15D Center circle Yellow, RHS 13A with a touch of RHS 24C Whole flower fades to light yellow (RHS 15D) as matures | Red-orange, RHS 44B | White, RHS 155 D |
| Shape of Petal | The width of the petal is 8 mm. The length is 10 mm. The shape ovate with mucronate apex. | The width of the petal is 10 mm. The length is 13 mm. The shape is obovate with cuspidate tip. | The width of the petal is 4 mm. The length is 8 mm. The shape is ovate with cuspidate tip. |
| Leaf | Hastate, dissected leaves with a long petiole and long lamina. The leaf apex is obtuse and the base is cunate. | Hastate, dissected leaves with a long petiole and long lamina. The leaf apex is obtuse and the base is cunate. | Obovate leaves with obtuse leaf tips and truncate bases. The leaf margin is undulate |
| Leaf Texture | The foliage is glabrous and shinning both above and below. | The foliage is glabrous, and more shinning above than below. | The foliage is glabrous and shinning both above and below. |

Of the many commercial cultivars known to the present Inventors, the most similar in comparison to 'KJ 2003 0747' is parental cultivar 'KJ 2000 0716'.

Comparing these two cultivars, the main distinctions are the form and the color of the flower, as described in the preceding table.

The new *Kalanchoe* cultivar 'KJ 2003 0747' has not been observed under all possible environmental conditions. The phenotype of the new cultivar may vary significantly with variations in environment such as temperature, light intensity, and day length without any change in the genotype of the plant.

The aforementioned photographs, together with the following observations, measurements and values describe the new *Kalanchoe* cultivar as grown in a greenhouse in Hinnerup, Denmark, under conditions which closely approximate those generally used in commercial practice.

In the following description, color references are made to the Royal Horticultural Society Colour Chart (RHS), published 1986, except where general colors of ordinary significance are used. Color values were taken under daylight conditions at approximately 12:00 p.m. in a greenhouse in Hinnerup, Denmark. The age of the plant described is 15 weeks (from the time the cutting was planted in growth medium to when the picture was taken).

Parentage:
  Male or pollen parent: *K. blossfeldiana* cultivar 'Monroe' (disclosed in U.S. Plant Patent No. PP14,714)
  Female or seed parent: *K. blossfeldiana*×*K. laciniata* interspecific hybrid cultivar 'KJ 2000 0716' (disclosed in U.S. patent application Ser. No. 10/654,571)
Classification:
  Botanical: *K. blossfeldiana*×*K. laciniata* interspecific hybrid cultivar 'KJ 2003 0747' (2nd generation after *K. blossfeldiana*×*K. laciniata* interspecific hybrid back-crossed with *K. blossfeldiana*).
PROPAGATION: Vegetative Terminal Cuttings
Rooting Habit: The cultivar has numerous, branched, fine and fibrous roots.
Time to initiate roots: It takes between one and two weeks to initiate roots.
Time to produce a rooted cutting: It will take three weeks to produce a well rooted cutting. In winter time, it can take one week more.
PLANT: If the plants are grown according to the description above, it will perform as described below. Variation from this description should be expected over the course of the year, and if the physical growing conditions varies from the description.
  Growth Habit: This cultivar is upright and uniform. The flowers are formed above the leaf canopy, but flowers will also appear between the leaves. The flowers are assembled in numerous compound inflorescences.
  Growth rate: Ready for sale after 14 weeks.
  Branching habit and description: Freely branching; typically 4 to 8 lateral branches develop per plant. Pinching (removal of the terminal apex) is not mandatory, but will enhance lateral branching. When grown in 10 cm pots the cultivar is not pinched. 'KJ 2003 0747' grown in 13 cm pot is pinched over 4 leaf pair. The enhancement of lateral branching in relation to the season varies.
  Height at flowering: The height of the cultivar is about 40 cm, from the bottom of the pot to the top of the plant, depending on growth conditions.
  Spread/Diameter at flowering: The diameter at flowering is about 25 cm.
  Stems:
    Appearance: The cultivar has around 8 stems with none, one or numerous leaf pairs on the stem. The inflorescence on top of the flower stem is branched, giving an inverted triangle with a rounded crown. Each inflorescence has between 40 and 60 flowers.
    Aspect: The stem is strong.
    Length: The length of the stem is between 15 and 20 cm depending on growth conditions
    Texture: The texture of the stem is glabrous and shinning.
    Color: The color of the stem is yellow-green, RHS 146 A.
  Foliage:
    Arrangement: The foliage is yellow-green with the same colors of the immature as well as the mature leaf, RHS 146 A and RHS 147 A. The majority of the leaves are at the base of the plant, but immature leaves appear also on the flowering stem.
    Overall Shape of Leaf: The leaves are defined as hastate, dissected leaves.
    Apex: The form of the apex is obtuse.
    Base: The form of the base is cunate.
    Length: The length of the foliage varies from about 6 cm for an immature leaf to about 22 cm for a mature leaf.
    Width: The width varies from about 3 cm for an immature leaf to about 13 cm for a mature leaf.
    Margin: The foliage has a dentate margin.
    Texture: The foliage is glabrous and shinning both above and below.
    Color of Upper Surface:
      Mature leaf: The color of the mature leaf is dark yellow-green, and is closely described with RHS 147 A.
      Immature leaf: The immature leaf has the same color as the mature leaf, dark yellow-green color, described with RHS 147 A.
    Color of Lower Surface:
      Mature leaf: The color of the lower surface is different from the upper surface, dark yellow-green color, and is closely described with RHS 146 A.
      Immature leaf: The immature leaf has the same color as the mature leaf, and is defined with dark yellow-green color, RHS 146 A.
    Venation Color: There is no visual appearance of veins.
      Upper surface: There is no difference between the color of venation and the rest of the leaf.
      Lower surface: There is no difference between the color of venation and the rest of the leaf.
  Petiole:
    Length: The length of petiole varies between an immature and mature leaf. The length of an immature leaf varies between 1.5 and 2 cm. The length of a mature leaf varies between 5 and 8 cm.
    Diameter: The diameter of petiole varies between an immature and mature leaf. The diameter of an immature leaf is 5 mm. The diameter of a mature leaf is 8 mm.
    Color: There is no difference between the color of petiole and the rest of the leaf.
  Flower Description:
    Flower type and habit: The flower type is a double-type with 16 to 25 petals per flower. The average number of petals per flower is 19.
    Natural flowering season: The flowering season is year round, when grown according to description above. When planting outside the flowering season will be in the summer (April to October), depending on local climatic conditions.
    Time to flower: The time from start of short day treatment to 1st flower is about 67 days, approximately 1 week longer in the winter time.
    Flowering stem length: The length of the flowering stem is between 14 and 20 cm depending of the growth conditions.
    Post-production longevity: 'KJ 2003 0747' maintains good leaf and flower display for at least 5 weeks under interior environmental conditions
    Winter Hardiness/weather tolerance: 'KJ 2003 0747' withstands wind, rain and direct sunlight, and can cope with temperatures between 40 and 95 degree F.

Fragrance: 'KJ 2003 0747' has no fragrance.

Flower size: The diameter of the flower ranges from 1.8 to 3.0 cm.

Overall shape: The shape is rose-like defined by at least 5 petals per flower.

Quantity: The cultivar produces a large number of flowers ranging from 250 to 300 flowers per plant.

Bud:

Rate of opening: From the bud is showing color the flower will open within 10 days.

Color: At the tip the bud is yellow, RHS 12 A, with a twist of yellow-orange, RHS 23 B, at the edge. At the base the bud is yellow-green and can closely be describe with RHS 144 B.

Shape: The shape of the bud is ellipsoidal with the smallest diameter toward the base.

Length: The length of the bud is about 1.7 cm

Diameter: The diameter of the bud is about 8 mm at the top and about 4 mm at the base.

Petal:

Quantity: Typically 16-20 petals fused at the base.

Shape: The shape of petal is oval.

Length: The length is 1 cm.

Width: The width is 7 mm.

Apex: The shape of apex is mucronate.

Margin: The shape of the margin can be described as entire.

Texture: The texture of the petals is soft, smooth and matte.

Color when opening:

Upper surface: The upper surface of the petal has different yellow colors changing from soft yellow to warm yellow, going from the outer circle to the center circle of the petals. The first petals are yellow, RHS 13 D, the next are yellow-orange, RHS 15 D, and the middle are yellow, RHS 13 A with a touch of 24C.

Lower surface: As for the lower surface the soft light yellow colors of the petals also changes going from the outer circle to the center circle of the petals. The first petals are yellow, RHS 6 D with a touch of RHS 29 D, the next are yellow, RHS 10 D and the center is yellow, RHS 4 D.

Color when fully open:

Upper surface: At maturity the whole flower fades to orange, RHS 27 D, with a touch of RHS 29 D in the center of the flower.

Lower surface: At maturity the lower surface fades to orange RHS 27 D, with a touch of RHS 29 D at the base of the petals.

Sepal:

Quantity: Typically 4 sepals fused at the base (stem).

Shape: The shape of sepal is lineal lanceolate.

Length: The length is about 9 mm.

Width: The width is about 2 mm.

Apex: The shape of the apex is acute.

Margin: The shape of the margin is entire.

Texture: The texture of the sepals is glabrous and shinning.

Color when opening:

Upper surface: The upper surface of the sepal is yellow-RHS 144 A.

Lower surface: The lower surface of the sepal is yellow-green, RHS 144 A.

Color when fully open:

Upper surface: The upper surface of the sepal is yellow-green, RHS 144 A.

Lower surface: The lower surface the sepal is yellow-green, RHS 144 A.

Peduncle:

Length: Every flower has a peduncle with a length of 4 mm.

Color: The peduncle is yellow-green, RHS 146 A.

Texture: The peduncle is glabrous and shinning.

Reproductive Organs:

Stamen:

Number: The flower has between 4 and 7 stamens.

Color: The color of the stamens is greyed-orange, RHS 177B.

Anthers:

Number: The number of anthers is between 4 and 7.

Size: The anthers are less than 1 mm in length.

Color: The color of the anthers are yellow-orange, RHS 14 B.

Filament Color The color of the filament is yellow-green, RHS 145 C.

Pollen Color The color of the pollen is yellow-orange, RHS 17 C.

Pollen Amount: A medium amount of pollen with a medium pollen fertility of about 60% depending on time of year.

Pistil:

Number: The number of pistils is four.

Stigma:

Shape: The shape of stigma is round.

Color: The color of the stigma is yellow-green, RHS 145 A.

Style:

Shape: The shape of the style is thin and cylindrical.

Color: The color of style is yellow-green, RHS 144 A.

Ovary:

Color: The color of ovary is yellow-green, RHS 144 B.

Seeds:

Number: Between 50 and 60 potential seeds per ovary.

Width: The width of the seeds is less than 0.5 mm.

Length: The length of the seeds is less than 1 mm.

Shape: The shape of seeds is ellipsoidal.

Color: The color of the potential seeds is yellow-green, RHS 145 C.

Fruit (Ovary):

Shape: The shape of the fruit is cylindrical.

Width: The width of the fruit is about 1 mm.

Length: The length of the fruit is about 6 mm.

Color: The color of the fruit is yellow-green, RHS 145 A.

DISEASE/PEST RESISTANCE/SUSCEPTIBILITY: No information on disease or pest resistance or susceptibility is currently available.

EXAMPLE 5

Cultivar 'KJ 2003 0818'

The new *K. blossfeldiana*×. *K. laciniata* interspecific hybrid 'KJ 2003 0818' was produced using 1) a *K. blossfeldiana* double-type selection designated 'Leonardo', as the female parent, and is described in pending United States Plant Patent Number PP13,365, and 2) a proprietary single-type selection of *K. blossfeldiana*×*K. laciniata* interspecific hybrid 'KJ 1998-469', unpatented. The new *Kalanchoe* cultivar 'KJ 2003 0818' was discovered and selected as a flowering plant within the progeny of the stated cross in a controlled environment in Hinnerup, Denmark.

Asexual reproduction of the new cultivar by vegetative terminal cuttings was first performed in April, 2004, in Hinnerup, Denmark, and has demonstrated that the combination of characteristics as herein disclosed for the new cultivar are firmly fixed and retained through successive generations of asexual reproduction. The new cultivar reproduces true-to-type through asexual reproduction.

The following traits have been repeatedly observed and are determined to be unique characteristics of the new *Kalanchoe* cultivar 'KJ 2003 0818' which in combination distinguish this *Kalanchoe* as a new and distinct cultivar:

1. a large number of petals per flower resulting in a double-type or multi-petalled trait;
2. the large size of petals resulting in a large flower;
3. a unique soft pink color with a touch of yellow; and
4. a large number of flowers per plant.

The new *Kalanchoe* cultivar 'KJ 2003 0818' has not been observed under all possible environmental conditions. The phenotype of the new cultivar may vary significantly with variations in environment such as temperature, light intensity, and day length without any change in the genotype of the plant. The following observations, measurements and values describe the new *Kalanchoe* cultivar 'KJ 2003 01818' as grown in Hinnerup, Denmark under conditions which closely approximate those generally used in commercial practice.

Plants of 'KJ 2003 0818' differ from plants of the parental cultivars in the following characteristics:

In the following description, color references are made to the Royal Horticultural Society Colour Chart (RHS), published 2001, except where general colors of ordinary significance are used. Color values were taken under daylight conditions at approximately 12:00 p.m. in a greenhouse in Hinnerup, Denmark. The age of the plant described is 19 weeks (from the time the cutting was planted in growth medium to when the picture was taken).

Parentage:
   Male or pollen parent: *K. blossfeldiana*×*K. laciniata* interspecific hybrid 'KJ 1998 469'.
   Female or seed parent: *K. blossfeldiana* cultivar 'Leonardo' (disclosed in United States Plant Patent Number PP13,365).
Classification:
   Botanical: *K. blossfeldiana*×*K. laciniata* interspecific hybrid cultivar 'KJ 2003 0818'
   PROPAGATION: Vegetative terminal cuttings.
   Rooting Habit: The cultivar has numerous, branched, fine and fibrous roots.
   Time to initiate roots: It takes between 1 and 2 weeks to initiate roots.

| Trait | New Cultivar 'KJ 2003 0818' | Female Parent 'Leonardo' (patented, PP13,365) | Male Parent 'KJ 1998-469' (unpatented) |
|---|---|---|---|
| Height of cultivar | Is about 25 cm | Is about 30 cm | Is about 33 cm |
| Flower Type | Double-type | Double-type | Single-type |
| Flower Diameter | 20-24 mm | 15-17 mm | 20-25 mm |
| Flower number | 250-350 | 250-300 | 350-400 |
| Number of Corolla Lobes | Up to 43 full or partial petals | Between 18-25 full or partial petals | 4 petals |
| Corolla Coloration | Red-purple. Summer coloration: Center of the flower corolla is 65 A. Border of the corolla is 65 D. Fine thin longitudinal line from apex to base (1 mm) with 64 D. Winter coloration: Center of the corolla is 62A. The border of the corolla is 65 C. Fine thin longitudinal line from apex to base (1 mm) with 64 C. | Red-purple. RHS N74 A with one very thin longitudinal line from apex to base (1 mm) RHS 71 B. | Red-purple. RHS 68 B with many fine longitudinal lines RHS 62 D. The border of the corolla is 62 D. |
| Shape of petal | Broadly elliptic petals. The width of the petal is 6 mm and the length is 9 mm. The shape of the apex is cuspidate with entire margin. | Elliptic petals. The width of the petal is 4 mm and the length is 7 mm. The shape of the apex is cuspidate with entire margin. | Broadly elliptic petals. The width of the petal is 8 mm and the length is 12 mm. The shape of the apex is cuspidate with entire margin. |
| Leaf | Ovate leaves with medium petiole. The apex is obtuse and the base is obtuse. | Ovate leaves with medium petiole. The apex is obtuse and the base is rounded. | Elliptic leaves with long petiole. The apex is rounded and the base is obtuse. |
| Leaf texture | The texture of the leaf is glabrous and shinning. | The texture of the leaf is glabrous and shinning. | The texture of the leaf is glabrous and shinning. |

Of the many commercial cultivars known to the present Inventors, the most similar in comparison to 'KJ 2003 0818' is *Kalanchoe* cultivar 'KJ 2002 0504'. Comparing these two cultivars, besides the petal color being a different pink shade, the main distinction is that plants of 'KJ 2003 0818' have large sized petals resulting in large flowers which have a very harmonic symmetry.

Time to produce a rooted cutting: It will take 3 weeks to produce a well rooted cutting. In winter time, it can take on week more.

PLANT: If the plants are grown according to the description above, it will perform as described below. Variation from this description should be expected over the course of the year, and if the physical growing conditions varies from the description.

Growth habit: This cultivar is upright and uniform. The flowers are formed above the top of the leaf canopy, but the flowers will also appear between the leaves. The flowers are assembled in numerous compound inflorescences. 'KJ 2003 0818' is freely flowering with numerous compound cymes.

Growth rate: Ready for sale after 18 weeks.

Branching habit and description: Freely branching; typically 8 to 10 lateral branches develop per plant.

Height at flowering: The height of the cultivar is about 25 cm from the bottom of the pot to the top of the plant, depending on the growth conditions.

Spread/Diameter at flowering: The diameter of the cultivar at flowering is from leaf tip to leaf tip about 25 cm.

Stems:
  Appearance: The cultivar has between 8 to 10 stems with none, one or numerous leaf pairs on the stem. The inflorescence on the top of the flower stem is branched giving an inverted triangle with a rounded crown. Each branch has between 25 and 43 flowers.
  Aspect: The stem is strong.
  Length: The length varies from 12 to 16 cm depending on growth conditions.
  Texture: The texture of the stem is glabrous and shinning.
  Color: The color of the stem is yellow green, RHS 137 A.

Foliage:
  Arrangement: The foliage is yellow-green with the same color of the immature as well as the mature leaf, RHS 139 A. The majority of the leaves are at the base of the plant, but immature leaves appear also on the flowering stem.
  Overall Shape of Leaf: The leaves are defined as ovate leaves.
  Apex: The form of the apex is acute.
  Base: The form of the base is obtuse.
  Length: The length of the foliage varies from 5 cm for an immature leaf to 10.5 cm for a mature leaf.
  Width: The width varies from 3 cm for an immature leaf to 8 cm for a mature leaf.
  Margin: The foliage has a crenate margin.
  Texture: The foliage is glabrous and shinning.
  Color of Upper Surface:
    Mature leaf: The color of the mature leaf is a dark green color, and is closely described with RHS 139A. The margin has a brighter green color and is closely described with RHS 144A.
    Immature leaf: The immature leaf is a dark green color, and is closely described with RHS 139A. The margin has a brighter green color, and is closely described with RHS 144A.
  Color of Lower Surface:
    Mature leaf: The color of the lower surface is grayish green color, and is closely described with RHS 138A.
    Immature leaf: The immature leaf is a grayish green color, and is closely described with RHS 138A.
  Venation Color:
    Upper surface: No difference between the color of venation and the rest of the leaf.
    Lower surface: No difference between the color of venation and the rest of the leaf.

Petiole:
  Length: The length of the petiole varies between an immature and mature leaf. The length of an immature leaf is about 1 cm. The length of a mature leaf is about 3.5 cm.
  Diameter: The diameter of the petiole varies between an immature and mature leaf. The diameter of an immature leaf is 5 mm. The diameter of a mature leaf is 7 mm.
  Color: Dark green, RHS 139A.

Flower Description:
  Flower type and habit: The flower is a double-type with up to 43 petals per flower. The average number of petals per flower is 35.
  Natural flowering season: The flowering season is year round, when grown according to description above. When planting outside the flowering season will be in the summer (April to October), depending on local climatic conditions.
  Time to flower: The time from start of short day treatment to 1st flower is about 74 days, approximately 1 week longer in winter time.
  Flowering stem length: The length of the flowering stem is ranging from 15 to 18 cm depending on the growth conditions.
  Post production longevity: 'KJ 2003 0818' maintain good leaf and flower substance for at least 6 weeks under interior environmental conditions.
  Winter Hardiness/weather tolerance: 'KJ 2003 0818' withstands wind, rain and direct sunlight, and can cope with temperatures between 40 and 95 degrees F.
  Fragrance: 'KJ 2003 0818' has no fragrance.
  Flower size: The diameter of the flower range from 20 to 24 mm.
  Overall shape: The shape is rose-like shape, defined by at least 5 petals per flower.
  Quantity: 'KJ 2003 0818' produces a large number of flower ranging from 250 to 350 flowers per plant.

Bud:
  Rate of opening: From the time when the bud is showing color, the flower will open within 10 days.
  Color: The color of the bud is yellow green, RHS 144B with a touch of red-purple, RHS 65A.
  Shape: The shape of the bud is ellipsoidal with the smallest diameter toward the apex/base.
  Length: The length of the bud is about 1.5 cm.
  Diameter: The diameter of the bud is about 4 mm at the base and about 7 mm at the top.

Petal:
  Quantity: Typically 30-35 petals fused at the base.
  Shape: The shape of petal is broadly elliptic.
  Length: The length is about 9 mm.
  Width: The width is about 6 mm.
  Apex: The shape of the apex is cuspidate.
  Margin: The shape of the margin can be described as entire.
  Texture: The texture of the petals is soft, smooth and matte.
  Color (when opening & fully opened): The coloration of the upper surface of 'KJ 2003 0818' changes over the year. During summertime the colors are more intense, whereas the winter colors are more dusty.
    Summer time:
      Upper surface: The center of the upper surface of the petal has an intense warm red-purple color RHS 65 A. The border of the corolla has a bright red-purple color, RHS 65 D. A fine this longitudinal line from apex to base (wide is 1 mm) with a darker red-purple color, RHS 64 D.
      Lower surface: The lower surface of the petal is bright red-purple RHS 62 D, with a touch of a darker red-purple, RHS 62 B.
    Winter time:
      Upper surface: The center of the upper surface of the petal has a dusty warm red-purple color, RHS 62 A. The border of the petal is 65 C. Fine thin longitudinal line from apex to base (1 mm) with a darker red-purple color, RHS 64 C.

Lower surface: The lower surface of the petals is bright red-purple RHS 62 D with a touch of a darker red-purple RHS 62 B.
Sepal:
Quantity: Typically 4, fused or non-fused at based.
Shape: The shape of sepal is lanceolate.
Length: The length is 8 mm.
Width: The width is 3 mm.
Apex: The shape of the apex is acute.
Margin: The shape of the margin is entire.
Texture: The texture of the sepals is glabrous and shinning.
Color when opening:
　Upper surface: The upper surface of the sepal is yellow green, RHS 143A.
　Lower surface: The lower surface of the sepal is yellow green, RHS 143A.
Color when fully open:
　Upper surface: The upper surface of the sepal is yellow green, RHS 143A.
　Lower surface: The lower surface the sepal is yellow green, RHS 143A.
Peduncle description:
Length: Every flower has a peduncle with a length of 4 mm.
Color: The peduncle is green, RHS 144A.
Texture: The peduncle is glabrous and shinning.
Reproductive Organs:
Stamen:
Number: The flower has between 4 and 6 stamens.
Color: The color of the stamens is yellow-orange, RHS 19A.
Anthers:
Number: The number of anthers is between 4 and 6.
Size: The size is 1 mm in length.
Color: The color of the anthers is yellow-orange, RHS 20B.
Filament Color: The color of the filament is yellow-orange, RHS 19C.
Pollen Color: The color of the pollen is yellow-green, RHS 15C.
Pollen Amount: A very small amount of pollen with pour pollen fertility of 2%, depending on the time of year.
Gynoecium: Regarding the pistil, stigma, style and ovary abnormality of can occur, and a part of the female reproduction organs will not fully develop.
Pistil:
Number: The number of pistils is 3-4.
Stigma:
Shape: The shape of stigma is round.
Color: The color of the stigma is green, RHS 145 C.
Style:
Shape: The shape of the style is thin and cylindrical.
Color: The color of style is green, RHS 145 C.
Ovary:
Color: The color of ovary is green, RHS 144 C.
Seeds:
Number: Between 20 and 30 potential seeds per ovary.
Width: The width of the seeds is mm.
Length: The length of the seeds is mm.
Shape: The shape of the seeds is ellipsoidal.
Color: The color of the potential seeds is yellow-green, RHS 145 B.
Fruit (Ovary):
Shape: The shape of the fruit is cylindrical.
Width: The width of the fruit is 1.5 mm.
Length: The length of the fruit is 3 mm.
Color: The color of the fruit is green, RHS 144 C.
DISEASE RESISTANCE/SUSCEPTIBILITY: No information on disease resistance or susceptibility is currently available.
PEST RESISTANCE/SUSCEPTIBILITY: No information on disease resistance or susceptibility is currently available.

EXAMPLE 6

Cultivar 'KJ 2003 0727'

The new *K. blossfeldiana*×. *K. laciniata* interspecific hybrid 'KJ 2003 0727' was produced using 1) a *K. blossfeldiana* double-type selection designated 'Leonardo', as the female parent, and is described in pending United States Plant Patent Number PP13,365, and 2) a proprietary single-type selection of *K. blossfeldiana*×*K. laciniata* interspecific hybrid 'KJ 1998-469', unpatented. The new *Kalanchoe* cultivar 'KJ 2003 0727' was discovered and selected as a flowering plant within the progeny of the stated cross in a controlled environment in Hinnerup, Denmark.

Asexual reproduction of the new cultivar by vegetative terminal cuttings was first performed in March, 2004, in Hinnerup, Denmark, and has demonstrated that the combination of characteristics as herein disclosed for the new cultivar are firmly fixed and retained through successive generations of asexual reproduction. The new cultivar reproduces true-to-type through asexual reproduction.

The following traits have been repeatedly observed and are determined to be unique characteristics of the new *Kalanchoe* cultivar 'KJ 2003 0727' which in combination distinguish this *Kalanchoe* as a new and distinct cultivar:

1. a large number of petals per flower resulting in a double-type or multi-petalled trait;
2. the large size of petals resulting in a large flower;
3. a unique soft pink color with a touch of yellow; and
4. a large number of flowers per plant.

The new *Kalanchoe* cultivar 'KJ 2003 0727' has not been observed under all possible environmental conditions. The phenotype of the new cultivar may vary significantly with variations in environment such as temperature, light intensity, and day length without any change in the genotype of the plant. The following observations, measurements and values describe the new *Kalanchoe* cultivar 'KJ 2003 0727' as grown in Hinnerup, Denmark, under conditions which closely approximate those generally used in commercial practice.

Plants of 'KJ 2003 0727' differ from plants of the parental cultivars in the following characteristics:

| Trait | New Cultivar 'KJ 2003 0727' | Female Parent 'Leonardo' (patented, PP13,365) | Male Parent 'KJ 1998 469' (unpatented) |
| --- | --- | --- | --- |
| Height of cultivar | Is about 27 cm | Is about 30 cm | Is about 33 cm |
| Flower Type | Double-type | Double-type | Single-type |
| Flower Diameter | 22-25 mm | 15-17 mm | 20-25 mm |
| Flower number | 300-350 | 250-300 | 350-400 |

-continued

| Trait | New Cultivar 'KJ 2003 0727' | Female Parent 'Leonardo' (patented, PP13,365) | Male Parent 'KJ 1998 469' (unpatented) |
|---|---|---|---|
| Number of Corolla Lobes | Between 30-38 full or partial petals. | Between 18-25 full or partial petals | 4 petals |
| Corolla Coloration | Red-purple. Summer coloration: RHS 61 B and turn to 67 C after some days. Winter coloration: RHS N66 A. | Red-purple. RHS N74 A with one very thin longitudinal line from apex to base (1 mm) RHS 71 B. | Red-purple. RHS 68 B with many fine longitudinal lines RHS 62 D. The border of the corolla is 62 D. |
| Shape of petal | Broadly elliptic petals. The width of the petal is 7 mm and the length is 9 mm. The shape of the apex is cuspidate with entire margin. | Elliptic petals. The width of the petal is 4 mm and the length is 7 mm. The shape of the apex is cuspidate with entire margin. | Broadly elliptic petals. The width of the petal is 8 mm and the length is 12 mm. The shape of the apex is cuspidate with entire margin. |
| Leaf | Ovate leaves with medium petiole. The apex is rounded and the base is rounded. | Ovate leaves with medium petiole. The apex is obtuse and the base is rounded | Elliptic leaves with long petiole. The apex is rounded and the base is obtuse. |
| Leaf texture | The texture of the leaf is glabrous and shinning. | The texture of the leaf is glabrous and shinning. | The texture of the leaf is glabrous and shinning. |

Of the many commercial cultivars known to the present Inventors, the most similar in comparison to 'KJ 2003 0727' is *Kalanchoe* cultivar 'KJ 2002 0504'. Comparing these two cultivars, besides the petal color being a different pink shade, the main distinction is that plants of 'KJ 2003 0727' have large sized petals resulting in large flowers which have a very harmonic symmetry.

In the following description, color references are made to the Royal Horticultural Society Colour Chart (RHS), published 2001, except where general colors of ordinary significance are used. Color values were taken under daylight conditions at approximately 12:00 p.m. in a greenhouse in Hinnerup, Denmark. The age of the plant described is 19 weeks (from the time the cutting was planted in growth medium to when the picture was taken).

Parentage:
Male or pollen parent: *K. blossfeldiana×K. laciniata* interspecific hybrid 'KJ 1998 469'.
Female or seed parent: *K. blossfeldiana* cultivar 'Leonardo' (disclosed in United States Plant Patent Number PP13,365).

Classification:
Botanical: *K. blossfeldiana×K. laciniata* interspecific hybrid cultivar 'KJ 2003 0727'
PROPAGATION: Vegetative terminal cuttings.
Rooting Habit: The cultivar has numerous, branched, fine and fibrous roots.
Time to initiate roots: It takes between 1 and 2 weeks to initiate roots.
Time to produce a rooted cutting: It will take 3 weeks to produce a well rooted cutting. In winter time, it can take on week more.
PLANT: If the plants are grown according to the description above, it will perform as described below. Variation from this description should be expected over the course of the year, and if the physical growing conditions varies from the description.
Growth habit: This cultivar is upright and uniform. The flowers are formed above the top of the leaf canopy, but the flowers will also appear between the leaves. The flowers are assembled in numerous compound inflorescences. 'KJ 2003 0727' is freely flowering with numerous compound cymes.
Growth rate: Ready for sale after 18 weeks.
Branching habit and description: Freely branching; typically 8 to 10 lateral branches develop per plant. Pinching (removal of the terminal apex) is not mandatory, but will enhance lateral branching. When grown in 10.5 cm pots the cultivar is normally not pinched.
Height at flowering: The height of the cultivar is about 27 cm from the bottom of the pot to the top of the plant, depending on the growth conditions.
Spread/Diameter at flowering: The diameter of the cultivar at flowering is from leaf tip to leaf tip about 31 cm.
Stems:
Appearance: The cultivar has around 8 stems with none, one or numerous leaf pairs on the stem. The inflorescence on the top of the flower stem is branched giving an inverted triangle with a rounded crown. Each branch has between 20 and 40 flowers.
Aspect: The stem is strong.
Length: The length varies from 10 to 16 cm depending on growth conditions.
Texture: The texture of the stem is glabrous and shinning.
Color: The color of the stem is yellow-green, RHS 146 A.
Foliage:
Arrangement: The foliage is yellow-green with the same color of the immature as well as the mature leaf, RHS 147 A. The majority of the leaves are at the base of the plant, but immature leaves appear also on the flowering stem.
Overall Shape of Leaf: The leaves are defined as ovate with medium petiole.
Apex: The form of the apex is rounded.
Base: The form of the base is rounded.
Length: The length of the foliage varies from 3.5 cm for an immature leaf to 11 cm for a mature leaf.
Width: The width varies from 2 cm for an immature leaf to 6.5 cm for a mature leaf.
Margin: The foliage has a crenate margin.
Texture: The foliage is glabrous and shinning.
Color of Upper Surface:

Mature leaf: The color of the mature leaf is a yellow-green color, and is closely described with RHS 147 A.

Immature leaf: The immature leaf is a yellow-green color, and is closely described with RHS 147 A.

Color of Lower Surface:

Mature leaf: The color of the lower surface is yellow-green color, and is closely described with RHS 147 B.

Immature leaf: The immature leaf is a yellow-green color, and is closely described with RHS 147 B.

Venation Color:

Upper surface: No difference between the color of venation and the rest of the leaf.

Lower surface: No difference between the color of venation and the rest of the leaf.

Petiole:

Length: The length of the petiole varies between an immature and mature leaf. The length of an immature leaf is about 0.5 cm. The length of a mature leaf is about 2.5 cm.

Diameter: The diameter of the petiole varies between an immature and mature leaf. The diameter of an immature leaf is 4 mm. The diameter of a mature leaf is 7 mm.

Color: Yellow-green, RHS 147 B.

Flower Description:

Flower type and habit: The flower is a double-type with up to 38 petals per flower. The average number of petals per flower is 30.

Natural flowering season: The flowering season is year round, when grown according to description above. When planting outside the flowering season will be in the summer (April to October), depending on local climatic conditions.

Time to flower: The time from start of short day treatment to 1st flower is about 68 days, approximately 1 week longer in winter time.

Flowering stem length: The length of the flowering stem is ranging from 11 to 15 cm depending on the growth conditions.

Post production longevity: 'KJ 2003 0727' maintain good leaf and flower substance for at least 6 weeks under interior environmental conditions.

Winter Hardiness/weather tolerance: 'KJ 2003 0727' withstands wind, rain and direct sunlight, and can cope with temperatures between 40 and 95 degrees F.

Fragrance: 'KJ 2003 0727' has no fragrance.

Flower size: The diameter of the flower range from 22 to 25 mm.

Overall shape: The shape is rose-like shape, defined by at least 5 petals per flower.

Quantity: 'KJ 2003 0727' produces a large number of flower ranging from 300 to 350 flowers per plant.

Bud:

Rate of opening: From the time when the bud is showing color, the flower will open within 10 days.

Color: The color of the bud is yellow-green, RHS 144 B, with a touch of red-purple, RHS 58 A.

Shape: The shape of the bud is ellipsoidal with the smallest diameter toward the base.

Length: The length of the bud is about 1.2 cm.

Diameter: The diameter of the bud is about 5 mm at the base and about 8 mm at the top.

Petal:

Quantity: Typically 30-38 petals fused at the base.

Shape: The shape of petal is broadly elliptic.

Length: The length is about 9 mm.

Width: The width is about 7 mm.

Apex: The shape of the apex is cuspidate.

Margin: The shape of the margin can be described as entire.

Texture: The texture of the petals is soft, smooth and matte.

Color when opening: The coloration of the upper surface of 'KJ 2003 0727' changes over the year. During summer time the colors are more intense and warm, whereas the winter colors are dustier.

Summer time:

Upper surface: The upper surface of the petal has a deep, warm red-purple color, RHS 61 B, and turn after some days to RHS 67 C.

Lower surface: The lower surface of the petal is red-purple, RHS 65 C with a touch of RHS 167 C.

Winter time:

Upper surface: The upper surface of the petal is deep, warm red-purple, RHS N66 A.

Lower surface: The lower surface of the petal is red-purple, RHS 65 C with a touch of RHS 167 C.

Color when fully open:

Upper surface: The upper surface of the petal is red-purple, RHS N66 A.

Lower surface: The lower surface the petal is red-purple, RHS 65 C with a touch of RHS 67 C.

Sepal:

Quantity: Typically 4 fused or non-fused at based.

Shape: The shape of sepal is lanceolate.

Length: The length is 6 mm.

Width: The width is 2 mm.

Apex: The shape of the apex is acute.

Margin: The shape of the margin is entire.

Texture: The texture of the sepals is shinning and glabrous.

Color when opening:

Upper surface: The upper surface of the sepal is green, RHS 143 B.

Lower surface: The lower surface of the sepal is green, RHS 143 B.

Color when fully open:

Upper surface: The upper surface of the sepal is green, RHS 143 B.

Lower surface: The lower surface the sepal is green, RHS 143 B.

Peduncle description:

Length: Every flower has a peduncle with a length of 5 mm.

Color: The peduncle is yellow-green, RHS 147 B.

Texture: The peduncle is glabrous and shinning.

Reproductive Organs:

Stamen:

Number: The flower has between 3 and 8 stamens.

Color: The color of the stamens is greyed-orange, RHS 177 B.

Anthers:

Number: The number of anthers is between 3 and 8.

Size: The size is 1 mm in length.

Color: The color of the anthers is yellow-orange, RHS 16 B.

Filament Color: The color of the filament is yellow-green, RHS 145 C.

Pollen Color: The color of the pollen is yellow-green, RHS 15 C.

Pollen Amount: A small amount of pollen with a medium pollen fertility of 50%, depending on the time of year.

Pistil:

Number: The number of pistils is 4.

Stigma:

Shape: The shape of stigma is round.

Color: The color of the stigma is yellow-green, RHS 145 A.

Style:

Shape: The shape of the style is thin and cylindrical.

Color: The color of style is green, RHS 138 A.

Ovary:
Color: The color of ovary is green, RHS 137 C.
Seeds:
Number: Between 20 and 25 potential seeds per ovary.
Width: The width of the seeds is less than 0.5 mm.
Length: The length of the seeds is less than 1 mm.
Shape: The shape of the seeds is ellipsoidal.
Color: The color of the potential seeds is yellow-green, RHS 145 B.
Fruit (Ovary):
Shape: The shape of the fruit is cylindrical.
Width: The width of the fruit is 3 mm.
Length: The length of the fruit is 5 mm.
Color: The color of the fruit is yellow-green, RHS 145 A.
DISEASE RESISTANCE/SUSCEPTIBILITY: No information on disease resistance or susceptibility is currently available.
PEST RESISTANCE/SUSCEPTIBILITY: No information on disease resistance or susceptibility is currently available.

EXAMPLE 7

Cultivar 'KJ 2004 0722'

The new *K. blossfeldiana*×*K. rotundifolia* interspecific hybrid 'KJ 2004 0722' was produced using a proprietary double-type selection of *K. blossfeldiana* designated 'KJ 2002 0502' (unpatented) as the female parent. The male parent was an unnamed, unpatented single-type selection of *K. rotundifolia*. The new *Kalanchoe* cultivar 'KJ 2004 0722' was discovered and selected as a single flowering plant within the progeny of the stated cross in a controlled environment in Hinnerup, Denmark.

The new interspecific hybrid is herein described by a flowering seedling of 'KJ 2004 0722'.

Asexual reproduction of the new cultivar by vegetative terminal cuttings was first performed in July of 2005 in Hinnerup, Denmark, and has demonstrated that the combination of characteristics as herein disclosed for the new cultivar are firmly fixed and retained through successive generations of asexual reproduction. The new cultivar reproduces true-to-type through asexual reproduction.

The following traits have been observed and are determined to be unique characteristics of the new *Kalanchoe* cultivar 'KJ 2004 0722' which in combination distinguish this *Kalanchoe* as a new and distinct cultivar:

1. a large number of petals per flower resulting in a double-type or multi-petalled trait;
2. the small size of its petals resulting in a unique flower shape;
3. small, dissected leaves on young, as well as, mature leaves;
4. a unique combination of purple and pink colored petals; and
5. a large number of flowers per plant.

The new *Kalanchoe* cultivar 'KJ 2004 0722' has not been observed under all possible environmental conditions. The phenotype of the new cultivar may vary with variations in environment such as temperature, light intensity, and day length without any change in the genotype of the plant. The following observations, measurements and values describe the new *Kalanchoe* cultivar 'KJ 2004 0722' as grown in Hinnerup, Denmark, under conditions which closely approximate those generally used in commercial practice.

Plants of 'KJ 2004 0722' differ from plants of the parental cultivars in the following characteristics:

| Trait | New Cultivar 'KJ 2004 0722' | Female Parent 'KJ 2002 0502' (unpatented) | Male Parent Unnamed, unpatented *K. rotundifolia* cultivar |
| --- | --- | --- | --- |
| Height of Cultivar | About 31 cm | About 25 cm | About 45 cm |
| Flower Type | Double-type | Double-type | Single-type |
| Flower Diameter | 15 mm | 17 mm | 4 mm |
| Flower Number Per Plant | About 300 | About 300 | About 400 |
| Number of Corolla Lobes | Between 14 and 18 petals per flower | Between 14 and 22 petals per flower | 4 petals per flower |
| Corolla Coloration | From outer petals to center of flower: First circle Yellow, RHS 13 D Next circle Yellow-orange, RHS 15 D Center circle Yellow, RHS 13 A with a touch of orange, RHS 24 C Whole flower fades to light yellow (RHS 15 D) as matures | The color of the corolla lobes is best described as red-purple defined as RHS 74 A | The color of the corolla lobes is best described as orange-red, defined between RHS 31 A and RHS 31 B |
| Shape of Petal | The width of the petal is 8 mm. The length is 10 mm. The shape is ovate with mucronate apex. | The width of the petal is 5 mm. The length is 8 mm. The shape is ovate with mucronate apex. | The width of the petal is 2 mm. The length is 5 mm. The shape is oblong lanceolate with acute apex. |

-continued

| Trait | New Cultivar 'KJ 2004 0722' | Female Parent 'KJ 2002 0502' (unpatented) | Male Parent Unnamed, unpatented K. rotundifolia cultivar |
|---|---|---|---|
| Leaf | Hastate, dissected leaves with a long petiole and long lamina. The leaf apex is obtuse and the base is cunate. | Medium size of elliptic leaves with medium length of petiole. The leaf apex as well as the base is rounded. | Spatulate leaves with a long petiole and long lamina. The leaf apex is round and the base is obtuse. |
| Leaf Texture | The foliage is glabrous and shinning both above and below. | The foliage is glabrous both above and below. | The foliage is matte both above and below. |

Of the many commercial cultivars known to the present Inventors, the most similar in comparison to 'KJ 2004 0722' is parental cultivar 'KJ 2002 0502'. Comparing these two cultivars, the main distinctions are the form and the color of the flower, as described in the preceding table.

In the following description, color references are made to the Royal Horticultural Society Colour Chart (RHS), published 2001, except where general colors of ordinary significance are used. Color values were taken under daylight conditions at approximately 12:00 p.m. in a greenhouse in Hinnerup, Denmark.

The aforementioned photographs, together with the following observations, measurements and values describe the new *Kalanchoe* cultivar 'KJ 2004 0722' as grown in a greenhouse in Hinnerup, Denmark, under conditions which closely approximate those generally used in commercial practice. The age of the plant described is 15 weeks (from the time the cutting was planted in growth medium to when the picture was taken).

Parentage:
Male or pollen parent: Unnamed, unpatented *K. rotundifolia* cultivar
Female or seed parent: *K. blossfeldiana* cultivar 'KJ 2002 0502'(unpatented)
Classification:
Botanical: *K. blossfeldiana*×*K. rotundifolia* interspecific hybrid cultivar 'KJ 2004 0722'.
PROPAGATION: Vegetative terminal cuttings
Rooting Habit: The cultivar has numerous, branched, fine and fibrous roots.
Time to initiate roots: It takes between 1 and 2 weeks to see the initiation of roots.
Time to produce a rooted cutting: It will take 3 weeks to produce a well rooted cutting. In winter time, it can take one more week.
PLANT: If the plants are grown according to the description above, it will perform as described below. Variation from this description should be expected over the course of the year, and if the physical growing conditions varies from the description.
Growth Habit: This cultivar is upright and uniform. The flowers are formed above the leaf canopy, but flowers will also appear between the leaves. The flowers are assembled in numerous compound inflorescences.
Growth rate: Ready for sale after 10 weeks.
Branching habit and description: Freely branching. The seedling has 3 lateral branches develop.
Height at flowering: The height of the seedling is about 35 cm, from the bottom of the pot to the top of the plant, depending on growth conditions.
Spread/Diameter at flowering: The diameter at flowering is about 13 cm.

Stems:
Appearance: The seedling has around 3 stems with one or numerous leaf pairs on the stem. The inflorescence on the top of the flower stem is branched, giving an inverted triangle with a rounded crown. Each inflorescence has between 35 and 100 flowers.
Aspect: The stem is strong.
Length: The length of the stem is about 20 cm.
Texture: The texture of the stem is glabrous and shinning.
Color: The color of the part of the stem closest to the inflorescence is yellow-green, RHS 146 A. Going from the top of the stem to the part of the stem closest to the root, the color of the stem changes to a grey-orange color, RHS 166 A.
Foliage:
Arrangement: The color of the foliage within this seedling varies. In, general, the foliage is yellow-green in color, RHS 146 B, but with a grayed-orange color along the margin, RHS 166 A, for both the immature and mature leaves. The majority of the leaves are at the base of the plant, but immature leaves appear also on the flowering stem.
Overall Shape of Leaf: The leaves are defined as orbicular and elliptic.
Apex: The form of the apex is round.
Base: The form of the base is round.
Length: The length of the foliage varies from about 2 cm for an immature leaf to about 7 cm for a mature leaf.
Width: The width varies from about 2 cm for an immature leaf to about 7 cm for a mature leaf.
Margin: The foliage has a dentate margin.
Texture: The foliage is glabrous and shinning
Color of Upper Surface:
  Mature leaf: The color of the mature leaf is dark yellow-green, RHS 146 B, with grayed-orange, RHS 166 A, along the margin of the leaf.
  Immature leaf: The immature leaf has the same color as the mature leaf.
Color of Lower Surface:
Mature leaf: Same as upper surface.
Immature leaf: Same as upper surface.
Venation Color: There is no visual appearance of veins.
Petiole:
Length: The length of petiole varies between an immature and mature leaf. The length of an immature leaf varies between 0.5 and 0.7 cm. The length of a mature leaf varies between 2 and 2.5 cm.
Diameter: The diameter of petiole varies between an immature and mature leaf. The diameter of an immature leaf is 3 mm. The diameter of a mature leaf is 7 mm.
Color: The color of the petiole has the same variation as the color of rest of the leaf, and is primarily yellow-green in color, RHS 146 B.

Flower Description:

Flower type and habit: The flower type is a double-type with about 14 to 18 petals per flower. The average number of petals per flower is 16.

Natural flowering season: The flowering season is year round, when grown according to the description above. When planting outside the flowering season will be in the summer (April to October), depending on local climatic conditions.

Time to flower: The time from start of short day treatment to 1$^{st}$ flower is about 70 days, approximately 1 week longer in the winter time.

Flowering stem length: The length of the flowering stem of the seedling is about 24 cm.

Post-production longevity: 'KJ 2004 0722' maintain good leaf and flower substance for at least 3 weeks under interior environmental conditions.

Winter Hardiness/weather tolerance: 'KJ 2004 0722' withstands wind, rain and direct sunlight, and can cope with temperatures between 40 and 95 degrees F.

Fragrance: 'KJ 2004 0722' has no fragrance.

Flower size: The diameter of the flower is about 1.5 cm.

Overall shape: The shape is rose-like defined by at least 5 petals per flower.

Quantity: The flowering seedling has about 300 flowers.

Bud: From the time when the bud is showing color, the flower will open within 10 days.
  Color: At the tip, the bud is red-purple, RHS 63 B, with a twist of red-purple, RHS 62 D, at the edge.
  Shape: The shape of the bud is ellipsoidal with the smallest diameter toward the base.
  Length: The length of the bud is about 1.7 cm
  Diameter: The diameter of the bud is about 6 mm at the top and about 4 mm at the base.

Petal:
Quantity: Typically 14-18 petals fused at the base.
Shape: The shape of petal is oval.
Length: The length is 6 mm.
Width: The width is 3.5 mm.
Apex: The shape of apex is mucronate.
Margin: The shape of the margin can be described as entire.
Texture: The texture of the petals is soft, smooth and matte.
Color when opening:
  Upper surface: The upper surface of the petal has a unique red-purple color, RHS 63A, with a little brighter red-purple color, RHS 63 B, at the apex of each petal.
  Lower surface: Red-purple color, RHS 63 D, with a twist of RHS 63 A, at the apex of each petal.
Color when fully open:
  Upper surface: At maturity the whole flower fades to a red-purple color, RHS 63 C.
  Lower surface: Very bright red-purple color, RHS 63 D.

Sepal:
Quantity: Typically 4 sepals fused at the base (stem).
Shape: The shape of sepal is lineal lanceolate.
Length: The length is about 5 mm.
Width: The width is about 2 mm.
Apex: The shape of the apex is acute.
Margin: The shape of the margin is entire.
Texture: The texture of the sepals is glabrous and shinning.
Color when opening:
  Upper and lower surfaces: Yellow-green, RHS 144 A.
Color when fully open:
  Upper and lower surfaces: Yellow-green, RHS 144 A.

Peduncle:
Length: Every flower has a peduncle with a length of 4 mm.
Color: The peduncle is yellow-green, RHS 146 A.
Texture: The peduncle is glabrous and shinning.

Reproductive Organs:
Stamen:
Number: The flower has between 4 and 10 stamens.
Color: The color of the stamens is grayed-yellow, RHS 163 C.
Anthers:
Number: The number of anthers is between 4 and 10.
Size: The anthers are less than 1 mm in length.
Color: The color of the anthers are yellow-orange, RHS 14 B.
Filament Color The color of the filament is yellow-green, RHS 145 C.
Pollen Color: The color of the pollen is yellow-orange, RHS 17 C.
Pollen Amount: A scarce amount of pollen with a pollen fertility of 0%.

Pistil:
Number: The number of pistils is four.
Stigma:
Shape: The shape of stigma is round.
Color: The color of the stigma is yellow-green, RHS 145 A.
Style:
Shape: The shape of the style is thin and cylindrical.
Color: The color of style is yellow-green, RHS 144 A.
Ovary:
Color: The color of ovary is yellow-green, RHS 144 B.
Seeds:
Number: Between 50 and 60 potential seeds per ovary.
Width: The width of the seeds is less than 0.5 mm.
Length: The length of the seeds is less than 1 mm.
Shape: The shape of seeds is ellipsoidal.
Color: The color of the potential seeds is yellow-green, RHS 145 C.
Fruit (Ovary):
Shape: The shape of the fruit is cylindrical.
Width: The width of the fruit is about 1 mm.
Length: The length of the fruit is about 6 mm.
Color: The color of the fruit is yellow-green, RHS 145 A.

DISEASE/PEST RESISTANCE/SUSCEPTIBILITY: No information on disease or pest resistance or susceptibility is currently available.

EXAMPLE 8

Cultivar 'KJ 2004 0723'

The new *K. blossfeldiana×K. rotundifolia* interspecific hybrid 'KJ 2004 0723' was produced using a proprietary double-type selection of *K. blossfeldiana* designated 'KJ 2002 0502' (unpatented) as the female parent. The male parent was an unnamed, unpatented single-type selection of *K. rotundifolia*. The new *Kalanchoe* cultivar 'KJ 2004 0723' was discovered and selected as a single flowering plant within the progeny of the stated cross in a controlled environment in Hinnerup, Denmark.

The new interspecific hybrid is herein described by a flowering seedling of 'KJ 2004 0723'.

Asexual reproduction of the new cultivar by vegetative terminal cuttings was first performed in July of 2005, in Hinnerup, Denmark, and has demonstrated that the combination of characteristics as herein disclosed for the new cultivar are firmly fixed and retained through successive generations of asexual reproduction. The new cultivar reproduces true-to-type through asexual reproduction.

The following traits have been observed and are determined to be unique characteristics of the new *Kalanchoe* cultivar 'KJ 2004 0723' which in combination distinguish this *Kalanchoe* as a new and distinct cultivar:
1. a large number of petals per flower resulting in a double-type or multi-petalled trait;
2. the small size of its petals resulting in a unique flower shape;
3. small, dissected leaves on young, as well as, mature leaves;
4. a unique combination of purple and pink colored petals; and
5. a large number of flowers per plant.

The new *Kalanchoe* cultivar 'KJ 2004 0723' has not been observed under all possible environmental conditions. The phenotype of the new cultivar may vary with variations in environment such as temperature, light intensity, and day length without any change in the genotype of the plant. The following observations, measurements and values describe the new *Kalanchoe* cultivar 'KJ 2004 0723' as a flowering seedling grown in Hinnerup, Denmark.

Plants of 'KJ 2004 0723' differ from plants of the parental cultivars in the following characteristics:

lished 2001, except where general colors of ordinary significance are used. Color values were taken under daylight conditions at approximately 12:00 p.m. in a greenhouse in Hinnerup, Denmark.

The aforementioned photographs, together with the following observations, measurements and values describe the new *Kalanchoe* cultivar as grown in a greenhouse in Hinnerup, Denmark, under conditions which closely approximate those generally used in commercial practice. The age of the plant described is 15 weeks (from the time the cutting was planted in growth medium to when the picture was taken).

Parentage:
Male or pollen parent: Unnamed, unpatented *K. rotundifolia* cultivar
Female or seed parent: *K. blossfeldiana* cultivar 'KJ 2002 0502' (unpatented)
Classification:
Botanical: *K. blossfeldiana*×*K. rotundifolia* interspecific hybrid cultivar 'KJ 2004 0723'.
Propagation: Vegetative Terminal Cuttings

| Trait | New Cultivar 'KJ 2004 0723' | Female Parent 'KJ 2002 0502' (unpatented) | Male Parent Unnamed, unpatented *K. rotundifolia* cultivar |
|---|---|---|---|
| Height of Cultivar | About 31 cm | About 25 cm | About 45 cm |
| Flower Type | Double-type | Double-type | Single-type |
| Flower Diameter | 15 mm | 17 mm | 4 mm |
| Flower Number Per Plant | About 300 | About 300 | About 400 |
| Number of Corolla Lobes | Between 14 and 18 petals per flower | Between 14 and 22 petals per flower | 4 petals per flower |
| Corolla Coloration | From outer petals to center of flower: First circle Yellow, RHS 13 D Next circle Yellow-orange, RHS 15 D Center circle Yellow, RHS 13 A with a touch of orange, RHS 24 C Whole flower fades to light yellow (RHS 15 D) as it matures | The color of the corolla lobes is best described as red-purple defined as RHS 74 A | The color of the corolla lobes is best described as orange-red, defined between RHS 31 A and RHS 31 B |
| Shape of Petal | The width of the petal is 8 mm. The length is 10 mm. The shape ovate with mucronate apex. | The width of the petal is 5 mm. The length is 8 mm. The shape is ovate with mucronate apex. | The width of the petal is 2 mm. The length is 5 mm. The shape is oblong lanceolate with acute apex. |
| Leaf | Hastate, dissected leaves with a long petiole and long lamina. The leaf apex is obtuse and the base is cunate. | Medium size of elliptic leaves with medium length of petiole. The leaf apex as well as the base is rounded. | Spatulate leaves with a long petiole and long lamina. The leaf apex is round and the base is obtuse. |
| Leaf Texture | The foliage is glabrous and shinning both above and below. | The foliage is glabrous both above and below. | The foliage is mat both above and below. |

Of the many commercial cultivars known to the present Inventors, the most similar in comparison to 'KJ 2004 0723' is parental cultivar 'KJ 2002 0502'. Comparing these two cultivars, the main distinctions are the form and the color of the flower, as described in the preceding table.

In the following description, color references are made to the Royal Horticultural Society Colour Chart (RHS), pub- Rooting Habit: The cultivar has numerous, branched, fine and fibrous roots.

Time to initiate roots: It takes between 1 and 2 weeks to initiate roots.

Time to produce a rooted cutting: It will take 3 weeks to produce a well rooted cutting. In winter time, it can take one more week.

PLANT: If the plants are grown according to the description above, it will perform as described below. Variation from this description should be expected over the course of the year, and if the physical growing conditions varies from the description.

Growth Habit: This cultivar is upright and uniform. The flowers are formed above the leaf canopy, but flowers will also appear between the leaves. The flowers are assembled in numerous compound inflorescences.

Growth rate: Ready for sale after 11 weeks.

Branching habit and description: Freely branching. The seedling has 4 lateral branches develop.

Height at flowering: The height of the seedling is about 33 cm, from the bottom of the pot to the top of the plant, depending on growth conditions.

Spread/Diameter at flowering: The diameter at flowering is about 21 cm.

Stems:

Appearance: The seedling has around 4 stems with one or numerous leaf pairs on the stem. The inflorescence on the top of the flower stem is branched, giving an inverted triangle with a rounded crown. Each inflorescence has between 35 and 100 flowers.

Aspect: The stem is strong.

Length: The length of the stem is about 30 cm.

Texture: The texture of the stem is glabrous and shinning.

Color: The color of the part of the stem closest to the inflorescence is yellow-green, RHS 146 B. Going from the top of the stem to the part of the stem closest to the root, the color of the stem changes to a grey-orange color, RHS 166A.

Foliage:

Arrangement: The color of the foliage within this seedling varies. In general, the leaf foliage is yellow-green in color, RHS 146 B, but with a grayed-orange color along the margin, RHS 166 A, for both the immature and mature leaves. The majority of the leaves are at the base of the plant, but immature leaves appear also on the flowering stem.

Overall Shape of Leaf: The leaves are defined as orbicular and elliptic leaves.

Apex: The form of the apex is round.

Base: The form of the base is round.

Length: The length of the foliage varies from about 2 cm for an immature leaf to about 7 cm for a mature leaf.

Width: The width varies from about 2 cm for an immature leaf to about 8 cm for a mature leaf.

Margin: The foliage has a dentate margin.

Texture: The foliage is glabrous and shinning on both upper and lower surfaces.

Color of Upper Surface:

Mature leaf: The color of the mature leaf is dark yellow-green, RHS 146 B, with grayed-orange, RHS 166 A, areas, along the margin of the leaf.

Immature leaf: The immature leaf has the same color as the mature leaf.

Color of Lower Surface:

Mature leaf: Same as upper surface.

Immature leaf: Same as upper surface.

Venation Color: There is no visual appearance of veins.

Petiole:

Length: The length of petiole varies between an immature and mature leaf. The length of an immature leaf varies between 0.5 and 0.7 cm. The length of a mature leaf varies between 2 and 2.5 cm.

Diameter: The diameter of petiole varies between an immature and mature leaf. The diameter of an immature leaf is 3 mm. The diameter of a mature leaf is 7 mm.

Color: The color of the petiole has the same variation as the color of rest of the leaf, and is primarily yellow-green, RHS 146 B.

Flower Description:

Flower type and habit: The flower type is a double-type with about 14 to 18 petals per flower. The average number of petals per flower is 16.

Natural flowering season: The flowering season is year round, when grown according to the description above. When planting outside the flowering season will be in the summer (April to October), depending on local climatic conditions.

Time to flower: The time from start of short day treatment to $1^{st}$ flower is about 77 days, approximately 11 week(s) longer in the winter time.

Flowering stem length: The length of the flowering stem of the seedling is about 24 cm.

Post-production longevity: 'KJ 2004 0723' maintain good leaf and flower substance for at least 3 weeks under interior environmental conditions.

Winter Hardiness/weather tolerance: 'KJ 2004 0723' withstands wind, rain and direct sunlight, and can cope with temperatures between 40 and 95 degrees F.

Fragrance: 'KJ 2004 0723' has no fragrance.

Flower size: The diameter of the flower is about 1.3 cm.

Overall shape: The shape is rose-like defined by at least 5 petals per flower.

Quantity: The flowering seedling has around 300 flowers.

Bud:

Rate of opening: From the time when the bud is showing color, the flower will open within 7 days.

Color: At the tip the bud is red-purple, RHS 64 A, with a twist of red-purple, RHS 62 C, at the edge.

Shape: The shape of the bud is ellipsoidal with the smallest diameter toward the base.

Length: The length of the bud is about 1.4 cm

Diameter: The diameter of the bud is about 6 mm at the top and about 4 mm at the base.

Petal:

Quantity: Typically 28-35 petals fused at the base.

Shape: The shape of petal is oval.

Length: The length is 7 mm.

Width: The width is 3.5 mm.

Apex: The shape of apex is mucronate.

Margin: The shape of the margin can be described as entire.

Texture: The texture of the petals is soft, smooth and matte.

Color when opening:

Upper surface: The upper surface of the petal has a unique red-purple color, RHS N66 A, with a little brighter red-purple color, RHS 63 B, at the apex of each petal.

Lower surface: Red-purple color, RHS 63 D, with a twist of RHS 63 A, at the apex of each petal.

Color when fully open:

Upper surface: At maturity the whole flower fades to a red-purple color, RHS 67 B.

Lower surface: Very bright red-purple color, RHS 63 D.

Sepal:

Quantity: Typically 4 sepals fused at the base (stem).

Shape: The shape of sepal is lineal lanceolate.

Length: The length is about 5 mm.

Width: The width is about 2 mm.

Apex: The shape of the apex is acute.

Margin: The shape of the margin is entire.
Texture: The texture of the sepals is glabrous and shinning.
Color when opening:
  Upper and lower surfaces: Yellow-green, RHS 144 A.
Color when fully open:
  Upper and lower surfaces: Yellow-green, RHS 144 A.
Peduncle:
Length: Every flower has a peduncle with a length of 4 mm.
Color: The peduncle is yellow-green, RHS 146 A.
Texture: The peduncle is glabrous and shinning.
Reproductive Organs:
Stamen:
Number: The flower has between 4 and 8 stamens.
Color: The color of the stamens is grayed-yellow, RHS 163 C.
Anthers:
Number: The number of anthers is between 4 and 10.
Size: The anthers are less than 1 mm in length.
Color: The color of the anthers are yellow-orange, RHS 14 B.
Filament Color The color of the filament is yellow-green, RHS 145 C.
Pollen Color The color of the pollen is yellow-orange, RHS 17 C.
Pollen Amount: A scarce amount of pollen with a pollen fertility of 0%.
Pistil:
Number: The number of pistils is four.
Stigma:
Shape: The shape of stigma is round.
Color: The color of the stigma is yellow-green, RHS 145 A.
Style:
Shape: The shape of the style is thin and cylindrical.
Color: The color of style is yellow-green, RHS 144 A.
Ovary:
Color: The color of ovary is yellow-green, RHS 144 B.
Seeds:
Number: Between 50 and 60 potential seeds per ovary.
Width: The width of the seeds is less than 0.5 mm.
Length: The length of the seeds is less than 1 mm.
Shape: The shape of seeds is ellipsoidal.
Color: The color of the potential seeds is yellow-green, RHS 145 C.
Fruit (Ovary):
Shape: The shape of the fruit is cylindrical.
Width: The width of the fruit is about 1 mm.
Length: The length of the fruit is about 6 mm.
Color: The color of the fruit is yellow-green, RHS 145 A.

DISEASE/PEST RESISTANCE/SUSCEPTIBILITY: No information on disease or pest resistance or susceptibility is currently available.

EXAMPLE 9

Cultivar 'KJ 2004 0724'

The new *K. blossfeldiana*×*K. rotundifolia* interspecific hybrid 'KJ 2004 0724' was produced using a proprietary double-type selection of *K. blossfeldiana* designated 'KJ 2002 0502' (unpatented) as the female parent. The male parent was an unnamed, unpatented single-type *K. rotundifolia* cultivar. The new *Kalanchoe* cultivar 'KJ 2004 0724' was discovered and selected as a single flowering plant within the progeny of the stated cross in a controlled environment in Hinnerup, Denmark.

The new interspecific hybrid is here described by a flowering seedling of 'KJ 2004 0724'.

Asexual reproduction of the new cultivar by vegetative terminal cuttings was first performed in July of 2005 in Hinnerup, Denmark, and has demonstrated that the combination of characteristics as herein disclosed for the new cultivar are firmly fixed and retained through successive generations of asexual reproduction. The new cultivar reproduces true-to-type through asexual reproduction.

The following traits have been observed and are determined to be unique characteristics of the new *Kalanchoe* cultivar 'KJ 2004 0724' which in combination distinguish this *Kalanchoe* as a new and distinct cultivar:

1. a large number of petals per flower resulting in a double-type or multi-petalled trait;
2. the small size of its petals resulting in a unique flower shape;
3. small, dissected leaves on young, as well as, mature leaves;
4. a unique combination of purple and pink colored petals and
5. a large number of flowers per plant.

The new *Kalanchoe* cultivar 'KJ 2004 0724' has not been observed under all possible environmental conditions. The phenotype of the new cultivar may vary significantly with variations in environment such as temperature, light intensity, and day length without any change in the genotype of the plant. The following observations, measurements and values describe the new *Kalanchoe* cultivar 'KJ 2004 0724' as a flowering seedling grown in Hinnerup, Denmark.

Plants of 'KJ 2004 0724' differ from plants of the parental cultivars in the following characteristics:

| Trait | New Cultivar 'KJ 2004 0724' | Female Parent 'KJ 2002 0502' (unpatented) | Male Parent Unnamed, unpatented *K. rotundifolia* cultivar |
|---|---|---|---|
| Height of Cultivar | About 31 cm | 25 cm | About 45 cm |
| Flower Type | Double-type | Double-type | Single-type |
| Flower Diameter | 15 mm | 17 mm | 4 mm |
| Flower Number Per Plant | About 300 | About 300 | About 400 |
| Number of Corolla Lobes | Between 14 and 18 petals per flower | Between 14 and 22 petals per flower | 4 petals per flower |
| Corolla Coloration | From outer petals to center of flower: | The color of the corolla lobes is best described | The color of the corolla lobes is best described as |

| Trait | New Cultivar 'KJ 2004 0724' | Female Parent 'KJ 2002 0502' (unpatented) | Male Parent Unnamed, unpatented K. rotundifolia cultivar |
|---|---|---|---|
| | First circle Yellow, RHS 13 D Next circle Yellow-orange, RHS 15 D Center circle Yellow, RHS 13 A with a touch of RHS 24 C Whole flower fades to light yellow (RHS 15 D) as matures | as red-purple defined as RHS 74 A | orange-red, defined between RHS 31 A and RHS 31 B |
| Shape of Petal | The width of the petal is 8 mm. The length is 10 mm. The shape ovate with mucronate apex. | The width of the petal is 5 mm. The length is 8 mm. The shape is ovate with mucronate apex. | The width of the petal is 2 mm. The length is 5 mm. The shape is oblong lanceolate with acute apex. |
| Leaf | Hastate, dissected leaves with a long petiole and long lamina. The leaf apex is obtuse and the base is cunate. | Medium size of elliptic leaves with medium length of petiole. The leaf apex as well as the base is rounded. | Spatulate leaves with a long petiole and long lamina. The leaf apex is round and the base is obtuse. |
| Leaf Texture | The foliage is glabrous and shinning both above and below. | The foliage is glabrous both above and below. | The foliage is mat both above and below. |

Of the many commercial cultivars known to the present Inventors, the most similar in comparison to 'KJ 2004 0724' is parental cultivar 'KJ 2002 0502'. Comparing these two cultivars, the main distinctions are the form and the color of the flower, as described in the preceding table.

In the following description, color references are made to the Royal Horticultural Society Colour Chart (RHS), published 2001, except where general colors of ordinary significance are used. Color values were taken under daylight conditions at approximately 12:00 p.m. in a greenhouse in Hinnerup, Denmark.

The aforementioned photographs, together with the following observations, measurements and values describe the new *Kalanchoe* cultivar as grown in a greenhouse in Hinnerup, Denmark, under conditions which closely approximate those generally used in commercial practice. The age of the plant described is 15 weeks (from the time the cutting was planted in growth medium to when the picture was taken).

Parentage:
Male or pollen parent: Unnamed, unpatented *K. rotundifolia* cultivar
Female or seed parent: *K. blossfeldiana* cultivar 'KJ 2002 0502' (unpatented)
Classification:
Botanical: *K. blossfeldiana*×*K. rotundifolia* interspecific hybridcultivar 'KJ 2004 0724'.
PROPAGATION: Vegetative Terminal Cuttings
Rooting Habit: The cultivar has numerous, branched, fine and fibrous roots.
Time to initiate roots: It takes between 1 and 2 weeks to initiate roots.
Time to produce a rooted cutting: It will take 3 weeks to produce a well rooted cutting. In winter time, it can take one more week.
PLANT: If the plants are grown according to the description above, it will perform as described below. Variation from this description should be expected over the course of the year, and if the physical growing conditions varies from the description.

Growth Habit: This cultivar is upright and uniform. The flowers are formed above the leaf canopy, but flowers will also appear between the leaves. The flowers are assembled in numerous compound inflorescences.
Growth rate: Read for sale after 11 weeks.
Branching habit and description: Freely branching. The seedling has 4 lateral branches develop.
Height at flowering: The height of the seedling is about 21 cm, from the bottom of the pot to the top of the plant, depending on growth conditions.
Spread/Diameter at flowering: The diameter at flowering is about 18 cm.
Stems:
Appearance: The seedling has around 4 stems with one or numerous leaf pairs on the stem. The inflorescence on the top of the flower stem is branched, giving an
inverted triangle with a rounded crown. Each inflorescence has between 35 and 100 flowers.
Aspect: The stem is strong.
Length: The length of the stem is about 14 cm.
Texture: The texture of the stem is glabrous and shinning.
Color: The color of the part of the stem closest to the inflorescence is yellow-green, RHS 139 A. Going from the top of the stem to the part of the stem closest to the root, the color of the stem changes to a grey-orange color, RHS 166 A.
Foliage:
Arrangement: The color of the foliage within this seedling has varies. In general, the foliage is green in color, RHS 139 A or dark yellow-green, RHS 147 A, but with a grayed-orange color along the margin, RHS 166 A, for both immature and mature leaves. The majority of the leaves are at the base of the plant, but immature leaves appear also on the flowering stem.
Overall Shape of Leaf: The leaves are defined as orbicular and elliptic leaves.
Apex: The form of the apex is round.
Base: The form of the base is round.
Length: The length of the foliage varies from about 2 cm for an immature leaf to about 8 cm for a mature leaf.
Width: The width varies from about 2 cm for an immature leaf to about 8 cm for a mature leaf.

Margin: The foliage has a dentate margin.
Texture: The foliage is glabrous and shinning on both the upper and lower surfaces.
Color of Upper Surface:
Mature leaf: The color of the mature leaf is dark yellow-green, and is best described with RHS 147 A, with grayed-orange, RHS 166 A, along the margin.
Immature leaf: The immature leaf has the same color as the mature leaf.
Color of Lower Surface:
Mature leaf: Same as upper surface.
Immature leaf: Same as upper surface.
Venation Color: There is no visual appearance of veins.
Petiole:
Length: The length of petiole varies between an immature and mature leaf. The immature leaves have no petiole. The length of the petiole of a mature leaf varies between 1.5 and 2.5 cm.
Diameter: The diameter of petiole varies between an immature and mature leaf. The diameter of an immature leaf is 3 mm. The diameter of a mature leaf is 7 mm.
Color: The color of the petiole has the same variation as the color of rest of the leaf, and is primarily dark yellow-green, RHS 147 A.
Flower Description:
Flower type and habit: The flower type is a double-type with about 14 to 25 petals per flower. The average number of petals per flower is 18.
Natural flowering season: The flowering season is year round, when grown according to the description above. When planting outside the flowering season will be in the summer (April to October), depending on local climatic conditions.
Time to flower: The time from start of short day treatment to $1^{st}$ flower is about 77 days, approximately 11 week(s) longer in the winter time.
Flowering stem length: The length of the flowering stem of the seedling is between 4 and 5 cm.
Post-production longevity: 'KJ 2004 0724' maintain good leaf and flower substance for at least 3 weeks under interior environmental conditions.
Winter Hardiness/weather tolerance: 'KJ 2004 0724' withstands wind, rain and direct sunlight, and can cope with temperatures between 40 and 95 degrees F.
Fragrance: 'KJ 2004 0724' has no fragrance.
Flower size: The diameter of the flower is about 1.1 cm.
Overall shape: The shape is rose-like defined by at least 5 petals per flower.
Quantity: The flowering seedling has around 300 flowers.
Bud:
Rate of opening: From the time when the bud is showing color, the flower will open within 7 days.
Color: At the tip the bud is red-purple, RHS 64 A, with a twist of red-purple, RHS 62 C, at the edge.
Shape: The shape of the bud is ellipsoidal with the smallest diameter toward the base.
Length: The length of the bud is about 1.1 cm
Diameter: The diameter of the bud is about 6 mm at the top and about 4 mm at the base.
Petal:
Quantity: Typically 14-25 petals fused at the base.
Shape: The shape of petal is oval.
Length: The length is 7 mm.
Width: The width is 3.5 mm.
Apex: The shape of apex is mucronate.
Margin: The shape of the margin can be described as entire.
Texture: The texture of the petals is soft, smooth and matte.
Color when opening:
Upper surface: The upper surface of the petal has a distinct red-purple color, RHS 65 C, with a darker red-purple color, RHS 67 C, at the apex, and RHS 67 A, at the base of each petal.
Lower surface: Red-purple color, RHS 68 C.
Color when fully open:
Upper surface: There is no difference between color of opening and fully opened petals.
Lower surface: There is no differences between color of opening and fully opened petals.
Sepal:
Quantity: Typically 4 sepals fused at the base (stem).
Shape: The shape of sepal is lineal lanceolate.
Length: The length is about 5 mm.
Width: The width is about 2 mm.
Apex: The shape of the apex is acute.
Margin: The shape of the margin is entire.
Texture: The texture of the sepals is glabrous and shinning.
Color when opening:
Upper and lower surfaces: Yellow-green, RHS 146 A.
Color when fully open:
Upper and lower surfaces: Yellow-green, RHS 146 A.
Peduncle:
Length: Every flower has a peduncle with a length of 5 mm.
Color: The peduncle is yellow-green, RHS 146 A.
Texture: The peduncle is glabrous and shinning.
Reproductive Organs:
Stamen:
Number: The flower has between 4 and 8 stamens.
Color: The color of the stamens is grayed-yellow, RHS 163 C.
Anthers:
Number: The number of anthers is between 2 and 6.
Size: The anthers are less than 1 mm in length.
Color: The color of the anthers are yellow-orange, RHS 14 B.
Filament Color: The color of the filament is yellow-green, RHS 145 C.
Pollen Color: The color of the pollen is yellow-orange, RHS 17 C.
Pollen Amount: A scarce amount of pollen with a pollen fertility of 0%.
Pistil:
Number: The number of pistils is four.
Stigma:
Shape: The shape of stigma is round.
Color: The color of the stigma is yellow-green, RHS 145 A.
Style:
Shape: The shape of the style is thin and cylindrical.
Color: The color of style is yellow-green, RHS 144 A.
Ovary:
Color: The color of ovary is yellow-green, RHS 144 B.
Seeds:
Number: Between 50 and 60 potential seeds per ovary.
Width: The width of the seeds is less than 0.5 mm.
Length: The length of the seeds is less than 1 mm.
Shape: The shape of seeds is ellipsoidal.
Color: The color of the potential seeds is yellow-green, RHS 145 C.
Fruit (Ovary):
Shape: The shape of the fruit is cylindrical.
Width: The width of the fruit is about 1 mm.
Length: The length of the fruit is about 6 mm.
Color: The color of the fruit is yellow-green, RHS 145 A.

DISEASE/PEST RESISTANCE/SUSCEPTIBILITY: No information on disease or pest resistance or susceptibility is currently available.

EXAMPLE 10

Cultivar 'KJ 2004 1122'

The new *K. blossfeldiana*×*K. aromatica* interspecific hybrid 'KJ 2004 1122' was produced using a proprietary double-type selection of *K. blossfeldiana* designated 'KJ 2002 0501' (unpatented) as the female parent. The male parent was an unnamed, unpatented single-type flower with bell shape *K. aromatica* cultivar. The new *Kalanchoe* cultivar 'KJ 2004 1122' was discovered and selected as a single flowering plant within the progeny of the stated cross in a controlled environment in Hinnerup, Denmark.

The new interspecific hybrid is here described by a flowering seedling of 'KJ 2004 1122'.

Asexual reproduction of the new cultivar by vegetative terminal cuttings was first performed in November of 2005, in Hinnerup, Denmark, The following traits have been observed and are determined to be unique characteristics of the new *Kalanchoe* cultivar 'KJ 2004 1122' which in combination distinguish this *Kalanchoe* as a new and distinct cultivar:

1. a large number of petals per flower resulting in a double-type or multi-petalled trait;
2. the large size of petals resulting in a larger flower;
3. small, dissected leaves on young, as well as, mature leaves;
4. a unique color combination of orange colored petals; and
5. a large number of flowers per plant.

The new *Kalanchoe* cultivar 'KJ 2004 1122' has not been observed under all possible environmental conditions. The phenotype of the new cultivar may vary significantly with variations in environment such as temperature, light intensity, and day length without any change in the genotype of the plant. The following observations, measurements and values describe the new *Kalanchoe* cultivar 'KJ 2004 1122' as grown in Hinnerup, Denmark, under conditions which closely approximate those generally used in commercial practice.

Plants of 'KJ 2004 1122' differ from plants of the parental cultivars in the following characteristics:

| Trait | New Cultivar 'KJ 2004 1122' | Female Parent 'KJ 2002 0501' (unpatented) | Male Parent Unnamed, unpatented *K. aromatica* cultivar |
| --- | --- | --- | --- |
| Height of Cultivar | About 15 cm | About 30 cm | The species is creeping; therefore, the height is about 20 cm, but the length of the stems is about 30 cm. |
| Flower Type | Double-type | Double-type | Single-type with bell shape. Petals has a tendency of bending backwards. |
| Flower Diameter | 24 mm | 25 mm | 5 mm |
| Flower Number Per Plant | About 200 | About 250 | About 200 |
| Number of Corolla Lobes | About 10 petals per flower | Between 18 and 25 petals per flower | About 4 petals per flower |
| Corolla Coloration | Orange, RHS 29 C | Red, RHS 50 A | Yellow-green, RHS 145 C |
| Shape of Petal | Oval | Oval | Oval |
| Leaf | Orbicular | Elliptic | Oblong |
| Leaf Texture | Glabrous and shinning | Glabrous and shinning | Hairy |

Of the many commercial cultivars known to the present Inventors, the most similar in comparison to 'KJ 2004 1122' is parental cultivar 'KJ 2002 0501'. Comparing these two cultivars, the main distinctions are the form and the color of the flower, as described in the preceding table.

In the following description, color references are made to the Royal Horticultural Society Colour Chart (RHS), published 2001, except where general colors of ordinary significance are used. Color values were taken under daylight conditions at approximately 12:00 p.m. in a greenhouse in Hinnerup, Denmark.

The aforementioned photographs, together with the following observations, measurements and values describe the new *Kalanchoe* cultivar as grown in a greenhouse in Hinnerup, Denmark, under conditions which closely approximate those generally used in commercial practice. The age of the plant described is 20 weeks (from the time the cutting was planted in growth medium to when the picture was taken).

Parentage:
Male or pollen parent: Unnamed, unpatented *K. aromatica* cultivar
Female or seed parent: *K. blossfeldiana* cultivar 'KJ 2002 0501'(unpatented)
Classification:
Botanical: *K. blossfeldiana*×*K. aromatica* interspecific hybrid cultivar 'KJ 2004 1122'.
PROPAGATION: Vegetative terminal cuttings
Rooting Habit: The cultivar has numerous, branched, fine and fibrous roots.

Time to initiate roots: It takes between 1 and 2 weeks to initiate roots.

Time to produce a rooted cutting: It will take 3 weeks to produce a well rooted cutting. In winter time, it can take one more week.

PLANT: If the plants are grown according to the description above, it will perform as described below. Variation from this description should be expected over the course of the year, and if the physical growing conditions varies from the description.

Growth Habit: This cultivar is upright and uniform. The flowers are formed above the leaf canopy, but flowers will also appear between the leaves. The flowers are assembled in numerous compound inflorescences.

Growth rate: Ready for sale after about 9 weeks. Since we only have seen this variety as a seedling yet, this an estimation.

Branching habit and description: Freely branching. The seedling has 3 lateral branches develop.

Height at flowering: The height of the seedling is about 18 cm, from the bottom of the pot to the top of the plant, depending on growth conditions.

Spread/Diameter at flowering: The diameter at flowering is about 12 cm.

Stems:

Appearance: The seedling has one with numerous leaf pairs on the stem. The inflorescence on the top of the flower stem is branched, giving an inverted triangle with a rounded crown. Each inflorescence has between 25 and 100 flowers.

Aspect: The stem is strong and has a tendency to creep.

Length: The length of the stem is about 15 cm.

Texture: The texture of the stem is glabrous and shinning.

Color: The color of the part of the stem closest to the inflorescence is yellow-green, RHS 146 C. Going from the top of the stem to the part of the stem closest to the root, the color of the stem changes to a dark yellow-green color, RHS 146 A.

Foliage:

Arrangement: The arrangement of the foliage within this seedling varies. In general, the lower leaves, as well as, the leaves at the stem carrying flowers bend downward. This characteristic is visualized in FIG. 26.

Overall Shape of Leaf: The leaves are defined as orbicular.

Apex: The form of the apex is round.

Base: The form of the base is round.

Length: The length of the foliage varies from about 2 cm for an immature leaf to about 7 cm for a mature leaf.

Width: The width varies from about 1.8 cm for an immature leaf to about 7 cm for a mature leaf.

Margin: The margin of the foliage is crenate and has a deep serratium.

Texture: The foliage is glabrous and shinning on both the upper and lower surfaces.

Color of Upper Surface:
Mature leaf: The color of the mature leaf is dark yellow-green, RHS 146 A. As visualized in FIG. 25, mature leaves have grayed-red, RHS 178 A, color blotches at the tip and along the margin.
Immature leaf: The immature leaf has the same color as the mature leaf.

Color of Lower Surface:
Mature leaf: The color of the mature leaf is dark yellow-green, RHS 146 B.
Immature leaf: Same as upper surface.

Venation Color: There is no visual appearance of veins.

Petiole:
Length: The length of petiole varies between an immature and mature leaf. The length of an immature leaf varies between 0.5 and 0.7 cm. The length of a mature leaf varies between 2 and 2.5 cm.

Diameter: The diameter of petiole varies between an immature and mature leaf. The diameter of an immature leaf is 3 mm. The diameter of a mature leaf is 7 mm.

Color: The color of the petiole has the same variation as the color of rest of the leaf, and is primarily dark yellow-green in color, RHS 146 A.

Flower Description:

Flower type and habit: The flower type is a double-type with about 7 to 18 petals per flower. The average number of petals per flower is 10.

Natural flowering season: The flowering season is year round, when grown according to the description above. When planting outside the flowering season will be in the summer (April to October), depending on local climatic conditions.

Time to flower: The time from start of short day treatment to $1^{st}$ flower is approx 63 days, approximately 2 weeks longer in the winter time.

Flowering stem length: The length of the flowering stem of the seedling is between 15 cm.

Post-production longevity: 'KJ 2004 1122' maintain good leaf and flower substance for at least 3 weeks under interior environmental conditions.

Winter Hardiness/weather tolerance: 'KJ 2004 1122' withstands wind, rain and direct sunlight, and can cope with temperatures between 40 and 95 degrees F.

Fragrance: 'KJ 2004 1122' has no fragrance.

Flower size: The diameter of the flower is about 2.4 cm.

Overall shape: The shape is rose-like defined by at least 5 petals per flower.

Quantity: The flowering seedling has about 200 flowers.

Bud:
Rate of opening: From the time when the bud is showing color, the flower will open within 7 days.
Color: The bud is yellow-green, RHS 145 A.
Shape: The shape of the bud is ellipsoidal with a sharpened tip.
Length: The length of the bud is about 1.7 cm
Diameter: The diameter of the bud is about 6 mm at the top, about 4 mm at the base and about 2 mm at the tip.

Petal:
Quantity: Typically about 10 petals fused at the base.
Shape: The shape of the petal is oval.
Length: The length is 12 mm.
Width: The width is 8 mm.
Apex: The shape of apex is mucronate.
Margin: The shape of the margin can be described as entire.
Texture: The texture of the petals is soft, smooth and matte.

Color when opening:
Upper surface: The upper surface of the petal has a unique bright orange color, RHS 29 C, with a touch of more intense orange colors, RHS 29 A and 29 B.
Lower surface: A bright orange color, RHS 29 D, with a line from the tip to the base of orange, RHS 29 A in the middle and a touch of RHS 29 A and 29B from the line to the margin.

Color when fully open:
Upper surface: At maturity, the whole flower fades to a yellow-orange color, RHS 18 B, with a small line of RHS 29 D going from the tip to the base.

Lower surface: Very bright yellow orange color, RHS 18 C, with a line from the tip to the base of RHS 29 A in the middle and a touch of RHS 29 A and 29 B from the line to the margin.

Sepal:

Quantity: Typically 4 sepals fused at the base (stem).

Shape: The shape of sepal is lineal lanceolate.

Length: The length is about 7 mm.

Width: The width is about 2 mm.

Apex: The shape of the apex is acute.

Margin: The shape of the margin is entire.

Texture: The texture of the sepals is glabrous and shinning.

Color when opening:
   Upper and lower surfaces: Yellow-green, RHS 144 C.

Color when fully open:
   Upper and lower surfaces: Yellow-green, RHS 144 C.

Peduncle:

Length: Every flower has a peduncle with a length of 4 mm.

Color: The peduncle is yellow-green, RHS 144 C.

Texture: The peduncle is glabrous and shinning.

Reproductive Organs:

Stamen:

Number: The flower has between 4 and 10 stamens.

Color: The color of the stamens is grayed-yellow, RHS 163 C.

Anthers:

Number: The number of anthers is between 4 and 10.

Size: The anthers are less than 1 mm in length.

Color: The color of the anthers are yellow-orange, RHS 14 B.

Filament Color: The color of the filament is yellow-green, RHS 145 C.

Pollen Color: The color of the pollen is yellow-orange, RHS 17 C.

Pollen Amount: A scarce amount of pollen with a pollen fertility of 0%.

Pistil:

Number: The number of pistils is four.

Stigma:

Shape: The shape of stigma is round.

Color: The color of the stigma is yellow-green, RHS 145 A.

Style:

Shape: The shape of the style is thin and cylindrical.

Color: The color of style is yellow-green, RHS 144 A.

Ovary:

Color: The color of ovary is yellow-green, RHS 144 B.

Seeds:

Number: Between 50 and 60 potential seeds per ovary.

Width: The width of the seeds is less than 0.5 mm.

Length: The length of the seeds is less than 1 mm.

Shape: The shape of seeds is ellipsoidal.

Color: The color of the potential seeds is yellow-green, RHS 145 C.

Fruit (Ovary):

Shape: The shape of the fruit is cylindrical.

Width: The width of the fruit is about 1 mm.

Length: The length of the fruit is about 6 mm.

Color: The color of the fruit is yellow-green, RHS 145 A.

DISEASE/PEST RESISTANCE/SUSCEPTIBILITY: No information on disease or pest resistance or susceptibility is currently available.

EXAMPLE 11

Cultivar 'KJ 2005 0159'

The new double type *Kalanchoe* interspecific hybrid 'KJ 2005 0159' was produced using 1) a proprietary double-type selection of *K. blossfeldiana*×*K. laciniata* interspecific hybrid designated 'KJ 2003 0638' (unpatented) as the female parent, and 2) a single type *K. blossfeldiana*×*K. pubescens* 'KJ 5003 0253' (unpatented) as the male parent. The female parent is described in pending 1) U.S. Plant patent application Ser. No. 11/011,611, 2) European Union Community Variety Rights Application No. 2004/0546, and 3) Canadian Plant Breeder's Rights Application No. 05-4713, and is a fertile interspecific hybrid between *K. blossfeldiana* and *K. laciniata*. The male parent was a fertile hybrid between *K. blossfeldiana* and *K. pubescens*. The new *Kalanchoe* cultivar 'KJ 2005 0159' was discovered and selected as a single flowering plant within the progeny of the stated cross in a controlled environment in Hinnerup, Denmark.

The new interspecific hybrid is here described by a flowering seedling of 'KJ 2005 0159'.

Asexual reproduction of the new cultivar by vegetative terminal cuttings has not been performed to date.

The following traits have been observed and are determined to be unique characteristics of the new *Kalanchoe* cultivar 'KJ 2005 0159' which in combination distinguish this *Kalanchoe* as a new and distinct cultivar:

1. a large number of petals per flower resulting in a double-type or multi-petalled trait;
2. the medium size of petals resulting in a medium diameter flower;
3. small, dissected leaves on young, as well as, mature leaves;
4. the orange-red colored petals; and
5. a large number of flowers per plant.

The new *Kalanchoe* cultivar 'KJ 2005 0159' has not been observed under all possible environmental conditions. The phenotype of the new cultivar may vary significantly with variations in environment such as temperature, light intensity, and day length without any change in the genotype of the plant. The following observations, measurements and values describe the new *Kalanchoe* cultivar 'KJ 2005 0159' as grown in Hinnerup, Denmark, under conditions which closely approximate those generally used in commercial practice.

Plants of 'KJ 2005 0159' differ from plants of the female parental cultivar, 'KJ 2003 0638' in the following characteristics:

| Trait | New Cultivar 'KJ 2005 0159' | Female Parent 'KJ 2003 0638' (unpatented) |
|---|---|---|
| Height of Cultivar | About 26 cm | About 31 cm |
| Flower Type | Double-type | Double-type |
| Flower Diameter | 15 mm to 22 mm | 20-25 mm |
| Flower Number Per Plant | Around 100 | 250-300 |
| Number of Corolla Lobes | From 8 to 20 full or partial petals | Up to 17 full or partial petals |
| Corolla | The color is best described | From outer to center of |

-continued

| Trait | New Cultivar 'KJ 2005 0159' | Female Parent 'KJ 2003 0638' (unpatented) |
|---|---|---|
| Coloration | as red, RHS 41A | flower: First circle Yellow-orange, RHS 20D Next circle Yellow-orange, RHS 19B Center circle Yellow-orange, RHS 20D with a twist of red, RHS 39C Whole flower faints to light orange RHS 27C |
| Shape of Petal | The width of the petal is 6-8 mm. The length is 7-10 mm. The shape is ovate with cuspidate apex. | The width of the petal is 9 mm. The length is 6 mm. The shape is ovate with mucronate apex. |
| Leaf | The lower leaves are ovate and the leaves towards the inflorescence are hastate. Both leaves types have long petiole. The leaf apex as well as the base is round on both leaves types. | Hastate, dissected leaves with a long petiole and long lamina. The leaf apex is obtuse and the base is cunate. |
| Leaf Texture | The foliage is glabrous and shinning both above and below. | The foliage is glabrous and shinning both above and below. |

No cultivars of the male parental cultivar, 'KJ 5003 0253' are available to provide a detailed comparison to the new cultivar. Two distinctions are the flower-type and number of petals. 'KJ 2005 0159' is a double-type flower with between 8 to 20-full or partial petals per flower, whereas 'KJ 2003 0253' is a single-type flower with about 4 petals per flower.

Of the many commercial cultivars known to the present Inventors, the most similar in comparison to 'KJ 2005 0159' is parental cultivar 'KJ 2003 0638'. Comparing these two cultivars, the main distinctions are the form and the color of the flower, as described in the preceding table.

In the following description, color references are made to the Royal Horticultural Society Colour Chart (RHS), published 2001, except where general colors of ordinary significance are used. Color values were taken under daylight conditions at approximately 12:00 p.m. in a greenhouse in Hinnerup, Denmark.

The aforementioned photographs, together with the following observations, measurements and values describe the new *Kalanchoe* cultivar as grown in a greenhouse in Hinnerup, Denmark, under conditions which closely approximate those generally used in commercial practice. The age of the plant described is 15 weeks (from the time the cutting was planted in growth medium to when the picture was taken).

Parentage:
  Male or pollen parent: *K. blossfeldiana*×*K. pubescens* interspecific hybrid KJ 5003 0253' (unpatented)
  Female or seed parent: *K. blossfeldiana*×*K. laciniata* interspecific hybrid 'KJ 2003 0638' (unpatented)
Classification:
  Botanical: (*K. blossfeldiana*×*K. laciniata*)×(*K. blossfeldiana*×*K. pubescens*) interspecific hybrid cultivar 'KJ 2005 0159'.
  Propagation: Vegetative Terminal Cuttings
Rooting Habit: The cultivar has numerous, branched, fine and fibrous roots.

Time to initiate roots: It takes between 1 and 2 weeks to initiate roots.

Time to produce a rooted cutting: It will take 3 weeks to produce a well rooted cutting. In winter time, it can take one more week.

PLANT: If the plants are grown according to the description above, it will perform as described below. Variation from this description should be expected over the course of the year, and if the physical growing conditions varies from the description.

Growth Habit: This cultivar is upright and uniform. The flowers are formed above the leaf canopy, but flowers will also appear between the leaves. The flowers are assembled in numerous compound inflorescences.

Growth rate: No information currently available.

Branching habit and description: Freely branching. The seedling has 2 lateral branches develop.

Height at flowering: The height of the seedling is about 26 cm, from the bottom of the pot to the top of the plant, depending on growth conditions.

Spread/Diameter at flowering: The diameter at flowering is about 11 cm.

Stems:
  Appearance: The seedling has 2 stems with one or numerous leaf pairs on the stem. The inflorescence on the top of the flower stem is branched, giving an inverted triangle with a rounded crown. The inflorescence has about 75 flowers.
  Aspect: The stem is strong.
  Length: The length of the stem is about 13 cm.
  Texture: The texture of the stem is glabrous and shinning.
  Color: The color of the part of the stem closest to the inflorescence is yellow-green, RHS 146 A. Going from the top of the stem to the part of the stem closest to the root, the color of the stem turns to a lighter yellow-green color, RHS 146 B.

Foliage:
  Arrangement: The color of the foliage within this seedling varies. In general, the foliage is yellow-green in color, RHS 146 C. Closest to the inflorescence, the color of the leaves are darker green, and described as RHS 137 A.
  Overall Shape of Leaf: The leaves are defined as ovate and hastate leaves.
    Apex: The form of the apex is round.
    Base: The form of the base is round.
    Length: The length of the foliage varies from about 4 cm for an immature leaf to about 6 cm for a mature leaf.
    Width: The width varies from about 1.2 cm for an immature leaf to about 5.5 cm for a mature leaf.
    Margin: The ovate leaves have a crenate margin with medium deep serratium.
    Texture: The foliage is glabrous and shinning on both the upper and lower surfaces.
    Color of Upper Surface:
      Mature leaf: The upper surface of an ovate and mature leaf is dark yellow-green, RHS 146 A.
      Immature leaf: The upper surface of a hastate and immature leaf is green, RHS 137 A.
    Color of Lower Surface:
      Mature leaf: The lower surface can be described with a mix between green, RHS 137 C and RHS 138 A.
      Immature leaf: The lower surface can be described as yellow-green, RHS 146 A.
    Venation Color: There is no visual appearance of veins.
  Petiole:
    Length: The length of petiole varies between an immature and mature leaf. The length of an immature leaf is between 1 and 2 cm. The length of a mature leaf varies around 2 cm.

Diameter: The diameter of petiole varies between an immature and mature leaf. The diameter of an immature leaf is between 5 and 7 mm. The diameter of a mature leaf is about 4 mm.

Color: The color of the petiole has the same variation as the color of rest of the leaf, and is primarily yellow green, RHS 146 A.

Flower Description:

Flower type and habit: The flower type is a double-type with about 8 to 20 petals per flower. The average number of petals per flower is 12.

Natural flowering season: The flowering season is year round, when grown according to the description above. When planting outside the flowering season will be in the summer (April to October), depending on local climatic conditions.

Time to flower: No information currently available.

Flowering stem length: The length of the flowering stem of the seedling is about 17 cm.

Post-production longevity: No information currently available.

Winter Hardiness/weather tolerance: 'KJ 2004 0722' withstands wind, rain and direct sunlight, and can cope with temperatures between 40 and 95 degrees F.

Fragrance: 'KJ 2005 0159' has no fragrance.

Flower size: The diameter of the flower is between 15 and 22 mm.

Overall shape: The shape is rose-like defined by at least 5 petals per flower.

Quantity: The flowering seedling has about 100 flowers.

Bud:
Rate of opening: No information currently available.
Color: The color of the bud is yellow-green, RHS 145 B, with a weak touch of red, RHS 41 A, at the tip.
Shape: The shape of the bud is ellipsoidal with the smallest diameter toward the base.
Length: The length of the bud is about 15 mm
Diameter: The diameter of the bud is about 5 mm at the top and about 3 mm at the base.

Petal:
Quantity: Typically 8 to 20 petals fused at the base.
Shape: The shape of petal is ovate.
Length: The length is 7 and 10 mm.
Width: The width is 6 and 8 mm.
Apex: The shape of apex is cuspidate.
Margin: The shape of the margin can be described as entire.
Texture: The texture of the petals is soft, smooth and matte.
Color when opening:
  Upper surface: The upper surface of the petal has a soft red color, RHS 41 A.
  Lower surface: Bright orange color, RHS 27 A, with a thin stripe from the base and 2 mm towards the apex described as yellow-green, RHS 144 C.
Color when fully open:
  Upper surface: The color is same as when opening.
  Lower surface: The color is same as when opening.

Sepal:
Quantity: Typically 4 sepals fused at the base (stem).
Shape: The shape of sepal is lanceolate.
Length: The length is between 8 and 10 mm.
Width: The width is between 2 and 5 mm.
Apex: The shape of the apex is acute.
Margin: The shape of the margin is entire.
Texture: The texture of the sepals is glabrous and shinning.
Color when opening:
Upper and lower surfaces: Yellow-green, RHS 146 C.
Color when fully open:
Upper and lower surfaces: Yellow-green, RHS 146 C.

Peduncle:
Length: Every flower has a peduncle with a length between 4 mm and 1.2 mm.
Color: The peduncle is yellow-green, RHS 137 B.
Texture: The peduncle is glabrous and shinning.

Reproductive Organs:
Stamen:
Number: The flower has between 6 and 10 stamens.
Color: The color of the stamens is grayed-yellow, RHS 161 D.

Anthers:
Number: The number of anthers is between 4 and 10.
Size: The anthers are between 0.5 and 1 mm in length.
Color: The color of the anthers are yellow-orange, RHS 15 C.

Filament Color The color of the filament is yellow-green, RHS 145 C.

Pollen Color The color of the pollen is yellow-orange, RHS 17 C.

Pollen Amount: A moderate amount of pollen with a pollen fertility of about 50% depending on the time of year.

Pistil:
Number: The number of pistils is four.
Stigma:
Shape: The shape of stigma is round.
Color: The color of the stigma is yellow-green, RHS 145 D.
Style:
Shape: The shape of the style is thin and cylindrical.
Color: The color of style is yellow-green, RHS 145 B.
Ovary:
Color: The color of ovary is yellow-green, RHS 143 A.

Seeds:
Number: Between 30 and 60 potential seeds per ovary.
Width: The width of the seeds is between 0.5 and 0.8 mm.
Length: The length of the seeds is about 1 mm.
Shape: The shape of seeds is ellipsoidal.
Color: The color of the seeds is yellow-green, RHS 145 C.

Fruit (Ovary):
Shape: The shape of the fruit is cylindrical.
Width: The width of the fruit is about 1 mm.
Length: The length of the fruit is about 6 mm.
Color: The color of the fruit is yellow-green, RHS 143 B.

DISEASE/PEST RESISTANCE/SUSCEPTIBILITY: No information on disease or pest resistance or susceptibility is currently available.

The invention has been described with reference to various specific and preferred embodiments and techniques. However, it should be understood that many variations and modifications may be made while remaining within the spirit and scope of the invention. The relevant portions of the references cited herein are incorporated by reference.

What is claimed is:

1. A method for breeding a double-type *Kalanchoe* interspecific hybrid plant that produces one or more flowers with at least 5 full or partial petals per flower comprising the steps of:

a. crossing a double-type *K. blossfeldiana* double-type plant, either as the male or female parent, with a single-type *Kalanchoe* plant selected from the group consisting of *K. laciniata, K. rotundifolia, K. aromatica K. pubescens, K. grandiflora, K. citrine, K. ambolensis, K. faustii, K. schumacherii, K. pritwitzii, K. flammea, K. figueredoi, K. rauhii, K. obtuse, K. pumila, K. marmorata, K. porphyrocalux, K. jongmansii, K. pinnata, K. diagremontiana, K. gracilipes, K. campanulata, K.*

*latisepela, K. coccinea, K. fedtschenkoi, K. tubiflora, K. decumbens, K. manginii, K. orgyalis, K. crenata* and *K. tomentosa;* b. selecting progeny that produce one or more flowers with at least 5 full or partial petals per flower.

2. The method according to claim 1, wherein the double-type interspecific progeny plant is back-crossed with one of the parents.

3. A method for breeding a double-type *Kalanchoe* interspecific hybrid plant that produces one or more flowers with at least 5 full or partial petals per flower comprising the step of selfing a double-type *Kalanchoe* interspecific hybrid selected from the group consisting of *K. blossfeldiana×K. laciniata, K. blossfeldiana×K. rotundifolia, K. blossfeldiana×K. aromatica, K. blossfeldiana×K. pubescens, K. blossfeldiana×K. grandiflora, K. blossfeldiana×K. citrina, K. blossfeldiana×K. ambolensis, K. blossfeldiana×K. faustii, K. blossfeldiana×K. schumacherii, K. blossfeldiana×K. pritwitzii, K. blossfeldiana×K. flammea, K. blossfeldiana×K. figueredoi, K. blossfeldiana×K. rauhii, K. blossfeldiana×K. obtusa, K. blossfeldiana × K. pumila, K. blossfeldiana×K. marmorata, K. blossfeldiana×K. porphyrocalux, K. blossfeldiana×K. jongmansii, K. blossfeldiana×K. pinnata, K. blossfeldiana×K. diagremontiana, K. blossfeldiana×K. gracilipes, K. blossfeldiana×K. campanulata, K. blossfeldiana×K. latisepela, K. blossfeldiana×K. coccinea, K. blossfeldiana×K. fedtschenkoi, K. blossfeldiana×K. tubiflora, K. blossfeldiana×K. decumbens, K. blossfeldiana×K. manginii, K. blossfeldiana×K. orgyalis, K. blossfeldiana×K. crenata* and *K. blossfeldiana×K. tomentosa.*

4. A method for breeding a double-type *Kalanchoe* interspecific hybrid plant that produces one or more flowers with at least 5 full or partial petals per flower comprising the steps of:

a. crossing a double-type *Kalanchoe* interspecific hybrid selected from the group consisting of *K. blossfeldiana×K. laciniata, K. blossfeldiana×K. rotundifolia, K. blossfeldiana×K. aromatica, K. blossfeldiana×K. pubescens, K. blossfeldiana×K. grandiflora, K. blossfeldiana×K. citrina, K. blossfeldiana×K. ambolensis, K. blossfeldiana×K. faustii, K. blossfeldiana×K. schumacherii, K. blossfeldiana×K. pritwitzii, K. blossfeldiana×K. flammea, K. blossfeldiana×K. figueredoi, K. blossfeldiana×K. rauhii, K. blossfeldiana×K. obtusa, K. blossfeldiana×K. pumila, K. blossfeldiana×K. marmorata, K. blossfeldiana×K. porphyrocalux, K. blossfeldiana×K. jongmansii, K. blossfeldiana×K. pinnata, K. blossfeldiana×K. diagremontiana, K. blossfeldiana×K. gracilipes, K. blossfeldiana×K. campanulata, K. blossfeldiana×K. latisepela, K. blossfeldiana×K. coccinea, K. blossfeldiana×K. fedtschenkoi, K. blossfeldiana×K. tubiflora, K. blossfeldiana×K. decumbens, K. blossfeldiana×K. manginii, K. blossfeldiana×K. orgyalis, K. blossfeldiana×K. crenata* and *K. blossfeldiana×K. tomentosa,* as the male or female parent, with single or double-type *Kalanchoe* plant of the same or different species, or hybrids from crosses of the above mentioned interspecific hybrids (e.g. (*K. blossfeldiana×K. laciniata*) x (*K. blossfeldiana×K. pubescens*), or crosses between interspecific hybrids containing *K. blossfeldiana* and interspecific hybrids not containing *K. blossfeldiana* hybrids (e.g. (*K blossfeldiana×K. laciniata*)×(*K. grandiflora* x *K. pritwitzii*); and b. selecting a progeny plant that produces double-type flowers.

\* \* \* \* \*